US011339441B2

(12) United States Patent
Rose et al.

(10) Patent No.: US 11,339,441 B2
(45) Date of Patent: May 24, 2022

(54) PROFILING CHEMICALLY MODIFIED DNA/RNA UNITS FOR DISEASE AND CANCER DIAGNOSIS

(71) Applicant: The Research Foundation for The State University of New York, Albany, MA (US)

(72) Inventors: Rebecca Rose, Albany, NY (US); Daniele Fabris, Clifton Park, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 201 days.

(21) Appl. No.: 15/152,996

(22) Filed: May 12, 2016

(65) Prior Publication Data
US 2017/0044619 A1 Feb. 16, 2017

Related U.S. Application Data

(60) Provisional application No. 62/160,196, filed on May 12, 2015.

(51) Int. Cl.
*C12Q 1/68* (2018.01)
*C12Q 1/6886* (2018.01)
(Continued)

(52) U.S. Cl.
CPC ............ *C12Q 1/6886* (2013.01); *C12Q 1/68* (2013.01); *C12Q 1/6872* (2013.01); *C12Q 1/6883* (2013.01); *H01J 49/0036* (2013.01)

(58) Field of Classification Search
CPC ...... C12Q 1/68; C12Q 1/6872; C12Q 1/6883; C12Q 1/6886
See application file for complete search history.

(56) References Cited

U.S. PATENT DOCUMENTS

2010/0279305 A1* 11/2010 Kuersten .............. C12Q 1/6855
435/6.16
2017/0059572 A1* 3/2017 Kalluri ............. G01N 33/57488

OTHER PUBLICATIONS

Direct infusion analysis of nucleotide mixtures of very similar or identical elemental composition Ryan Quinn, Maria Basanta-Sanchez, Rebecca R. Rose, Daniele Fabris J. Mass Spectrom. 2013, 48, 703-712 (Year: 2013).*

(Continued)

*Primary Examiner* — Brian R Gordon
*Assistant Examiner* — Dwan A Gerido
(74) *Attorney, Agent, or Firm* — Michael Krenicky; Steven A. Wood, Jr.

(57) ABSTRACT

The present invention relates to high-throughput methods comprising direct infusion electrospray ionization mass spectrometry (ESI-MS), multistep tandem mass spectrometry ($MS^n$), consecutive reaction monitoring (CRM), ion mobility spectrometry mass spectrometry (IMS-MS), high-resolution MS, and IMS-MS, for genome-wide (whole cell or tissue) profiling of DNA and RNA nucleotides/nucleosides having a wide variety of variant structural modifications. In particular, these methods are contemplated for providing a specific profile of variant DNA and/or RNA chemically modified nucleic acids (i.e. structures) associated with specific medical conditions. Medical conditions may include, but are not limited to: cancer; including prostate, lung, uterus, larynx, ovary, breast, kidney, and many other types of cancers; specific stages of cancer; bacterial infections; viral infections; genetic and metabolic disorders; and any condition involving changes in DNA and/or RNA structural modifications.

20 Claims, 26 Drawing Sheets

Specification includes a Sequence Listing.

(51) Int. Cl.
    C12Q 1/6883    (2018.01)
    C12Q 1/6872    (2018.01)
    H01J 49/00     (2006.01)

(56) References Cited

OTHER PUBLICATIONS

Isolation of Total RNA from Whole Blood and from Cells Isolated from Whole Blood. Applied Biosystems (Year: 2004).*
Ajay, et al., "Accurate and Comprehensive Sequencing of Personal Genomes." *Genome Res*, 21(9):1498-1505 (2011).
Apruzzese and Vouros, "Analysis of DNA Adducts by Capillary Methods Coupled to Mass Spectrometry: A Perspective." *J Chromatogr A*, 794(1-2):97-108 (1998).
Banks, et al., "Ultrasonically Assisted Electrospray Ionization for Lc/Ms Determination of Nucleosides from a Transfer RNA Digest." *Analytical Chemistry*, 66(3):406-414 (1994).
Banoub, et al., "Structural Investigation of Bacterial Lipopolysaccharides by Mass Spectrometry and Tandem Mass Spectrometry." *Mass Spectrom Rev*, 29(4):606-650 (2010A).
Banoub, et al., "Structural Investigation of Bacterial Lipopolysaccharides by Mass Spectrometry and Tandem Mass Spectrometry." *Mass Spectrom Rev*, 29(4):606-650 (2010B).
Biemann and McCloskey, "Application of Mass Spectrometry to Structure Problems. VI. Nucleosides." *Journal of the American Chemical Society*, 84(10):2005-2007 (1962).
Bischoff, et al., "Introduction of 5'-Terminal Functional Groups into Synthetic Oligonucleotides for Selective Immobilization." *Anal Biochem*, 164(2):336-344 (1987).
Cantara, et al., "The Rna Modification Database, Rnamdb: 2011 Update." *Nucleic Acids Res*, 39(Database issue):D195-201 (2011).
Carell, et al., "Structure and Function of Noncanonical Nucleobases." *Angew Chem Int Ed Engl*, 51(29):7110-7131 (2012).
Castro-Perez, et al., "Localization of Fatty Acyl and Double Bond Positions in Phosphatidylcholines Using a Dual Stage Cid Fragmentation Coupled with Ion Mobility Mass Spectrometry." *Journal of the American Society for Mass Spectrometry*, 22(9):1552-1567 (2011).
Chan, et al., "A Quantitative Systems Approach Reveals Dynamic Control of tRNA Modifications During Cellular Stress." *PLoS Genet*, 6(12):e1001247 (2010).
Charette and Gray, "Pseudouridine in RNA: What, Where, How, and Why." *IUBMB Life*, 49(5):341-351 (2000).
Clemmer and Jarrold, "Ion Mobility Measurements and Their Applications to Clusters and Biomolecules." *Journal of Mass Spectrometry*, 32(6):577-592 (1997).
Collings, et al., "A Combined Linear Ion Trap Time-of-Flight System with Improved Performance and Ms(N) Capabilities." *Rapid Commun Mass Spectrom*, 15(19):1777-1795 (2001).
Copela, et al., "The La Protein Functions Redundantly with Trna Modification Enzymes to Ensure tRNA Structural Stability." RNA, 12(4):644-654 (2006).
Crain, et al., "Mass Spectrometric Techniques in Nucleic Acid Research." *Mass Spectrometry Reviews*, 9(5):505-554 (1990a).
Crain "Preparation and Enzymatic Hydrolysis of DNA and RNA for Mass Spectrometry." *Methods Enzymol*, 193:782-790 (1990b).
Damen, et al., "Electrospray Ionization Quadrupole Ion-Mobility Time-of-Flight Mass Spectrometry as a Tool to Distinguish the Lot-to-Lot Heterogeneity in N-Glycosylation Profile of the Therapeutic Monoclonal Antibody Trastuzumab." *J Am Soc Mass Spectrom*, 20(11):2021-2033 (2009).
Dunin-Horkawicz, et al., "Modomics: A Database of RNA Modification Pathways." *Nucleic Acids Res*, 34(Database issue):D145-149 (2006).
Dwivedi, et al., "Gas-Phase Chiral Separations by Ion Mobility Spectrometry." *Anal Chem*, 78(24):8200-8206 (2006).
Esmans, et al., "Liquid Chromatography—Mass Spectrometry in Nucleoside, Nucleotide and Modified Nucleotide Characterization." *Journal of Chromatography A*, 794(1):109-127 (1998).

Ferre-D'Amare, "RNA-Modifying Enzymes." *Curr Opin Struct Biol*, 13(1):49-55 (2003).
Frommer, et al., "A Genomic Sequencing Protocol That Yields a Positive Display of 5-Methylcytosine Residues in Individual DNA Strands." *Proc Natl Acad Sci U S A*, 89(5):1827-1831 (1992).
Giles, et al., "Applications of a Travelling Wave-Based Radio-Frequency-Only Stacked Ring Ion Guide." *Rapid Commun Mass Spectrom*, 18(20):2401-2414 (2004).
Helm "Post-Transcriptional Nucleotide Modification and Alternative Folding of RNA." *Nucleic Acids Res*, 34(2):721-733 (2006).
Herman, et al., "Methylation-Specific PCR: A Novel PCR Assay for Methylation Status of cpg Islands." *Proceedings of the National Academy of Sciences of the United States of America*, 93(18):9821-9826 (1996).
Holmberg, et al., "The Biotin-Streptavidin Interaction Can Be Reversibly Broken Using Water at Elevated Temperatures." *Electrophoresis*, 26(3):501-510 (2005).
Icho and Wickner "The Double-Stranded RNA Genome of Yeast Virus L-a Encodes Its Own Putative Rna Polymerase by Fusing Two Open Reading Frames." *J Biol Chem*, 264(12):6716-6723 (1989).
Issa, et al., "Methylation of the Oestrogen Receptor Cpg Island Links Ageing and Neoplasia in Human Colon." *Nat Genet*, 7(4):536-540 (1994).
Johansson and Bystrom "Dual Function of the Trna(M(5)U54)Methyltransferase in tRNA Maturation." *RNA*, 8(3):324-335 (2002).
Koboldt, et al., "The Next-Generation Sequencing Revolution and Its Impact on Genomics." *Cell*, 155(1):27-38 (2013).
Kowalak, et al., "The Role of Posttranscriptional Modification in Stabilization of Transfer RNA from Hyperthermophiles." *Biochemistry*, 33(25):7869-7876 (1994).
Lapthorn, et al., "Ion Mobility Spectrometry-Mass Spectrometry (IMS-MS) of Small Molecules: Separating and Assigning Structures to Ions." *Mass Spectrom Rev*, 32(1):43-71 (pp. 1-35) (2013A).
Lapthorn, et al., "Ion Mobility Spectrometry-Mass Spectrometry (IMS-MS) of Small Molecules: Separating and Assigning Structures to Ions." *Mass Spectrom Rev*, 32(1):43-71 (pp. 35-45) (2013B).
Li, et al., "Methylation Protects miRNAs and siRNAs from a 3'-End Uridylation Activity in *Arabidopsis*." *Curr Biol*, 15(16):1501-1507 (2005).
Limbach, et al., "Summary: The Modified Nucleosides of RNA." *Nucleic Acids Res*, 22(12):2183-2196 (1994).
Machnicka, et al., "Modomics: A Database of RNA Modification Pathways—2013 Update." *Nucleic Acids Res*, 41(Database issue):D262-267 (2013).
Nordhoff, et al., "Mass Spectrometry of Nucleic Acids." *Mass Spectrom Rev*, 15(2):67-138 (1996).
Ofengand, "Ribosomal Rna Pseudouridines and Pseudouridine Synthases." *FEBS Lett*, 514(1):17-25 (2002).
Quinn, et al., "Direct Infusion Analysis of Nucleotide Mixtures of Very Similar or Identical Elemental Composition." *J Mass Spectrom*, 48(6):703-712 (2013).
Reyes-Darias, et al., "HIV RNA Dimerisation Interference by Antisense Oligonucleotides Targeted to the 5' Utr Structural Elements." *Virus Res*, 169(1):63-71 (2012).
Rose, et al., "Comprehensive ribonucleotide modification maps as possible tracking tools for the multistage processes involved in cell transformation from normalcy to malignancy." Poster Title only. WP 374. 62nd ASMS Conference on Mass Spectrometry and Allied Topics. Baltimore, Maryland. Jun. 15-19, 2014.
Rylova, et al., "The CLN3 Gene is a Novel Molecular Target for Cancer Drug Discovery." *Cancer Res*, 62(3):801-808 (2002).
Singer-Sam, et al., "Use of a HpaII-Polymerase Chain Reaction Assay to Study DNA Methylation in the Pgk-1 Cpg Island of Mouse Embryos at the Time of X-Chromosome Inactivation." *Mol Cell Biol*, 10(9):4987-4989 (1990).
Smith, et al., "METLIN: A Metabolite Mass Spectral Database." *Ther Drug Monit*, 27(6):747-751 (2005).
Solouki, et al., "High-Resolution Multistage MS, MS2, and MS3 Matrix-Assisted Laser Desorption/Ionization FT-ICR Mass Spectra of Peptides from a Single Laser Shot." *Anal Chem*, 68(21):3718-3725 (1996).

(56) References Cited

OTHER PUBLICATIONS

Su, et al., "Quantitative Analysis of Ribonucleoside Modifications in tRNA by Hplc-Coupled Mass Spectrometry." *Nat Protoc*, 9(4):828-841 (2014).
Tomer, et al., "Consecutive Reaction Monitoring in a Four-Sector Mass Spectrometer: Ms4 and One Step Beyond." *Anal Chem*, 60(20):2232-2236 (1988).
Verbeck, et al., "A Fundamental Introduction to Ion Mobility Mass Spectrometry Applied to the Analysis of Biomolecules." *J Biomol Tech*, 13(2):56-61 (2002).
Von Helden, et al., "Conformation of Macromolecules in the Gas Phase: Use of Matrix-Assisted Laser Desorption Methods in Ion Chromatography." *Science*, 267(5203):1483-1485 (1995).

\* cited by examiner

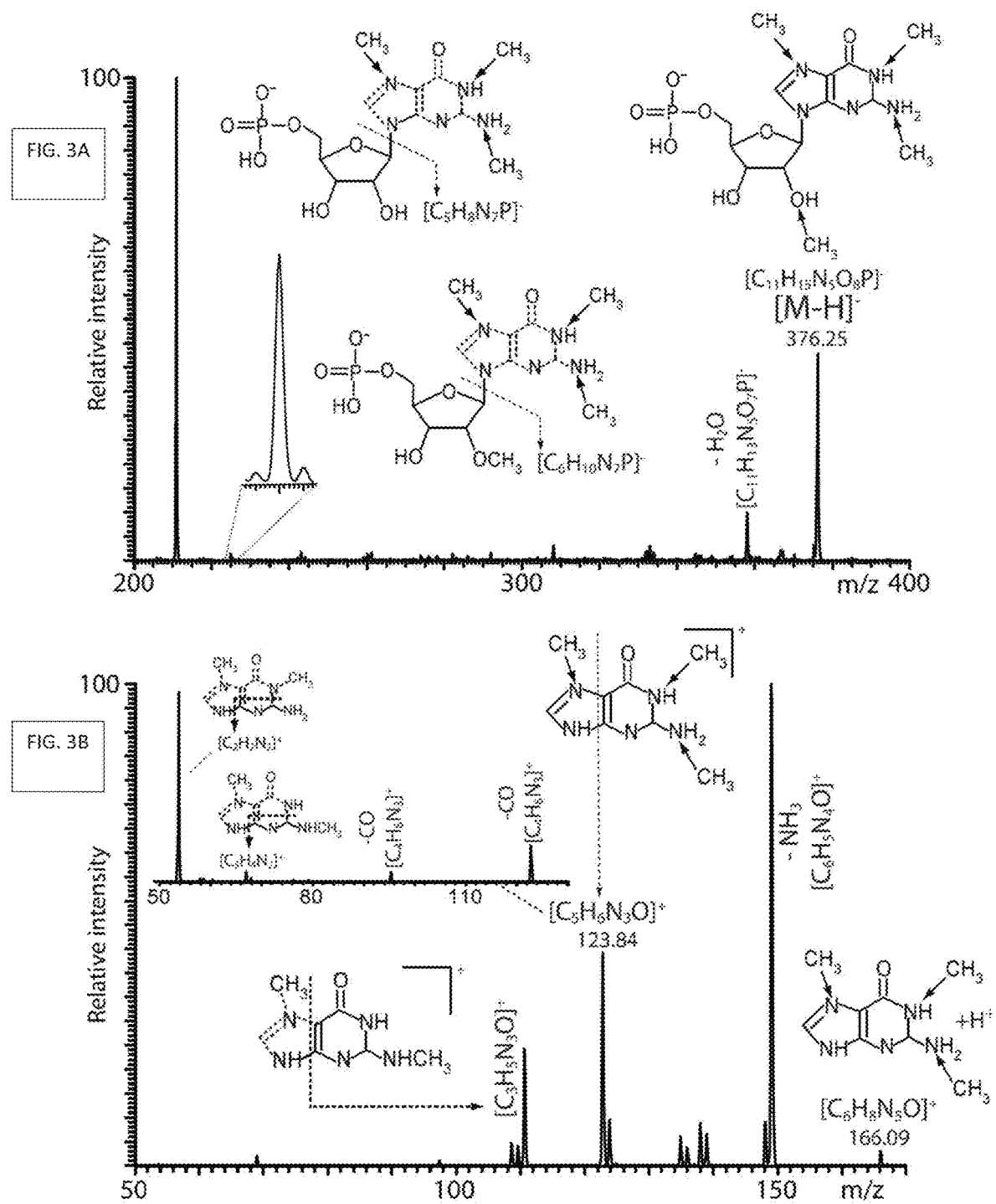

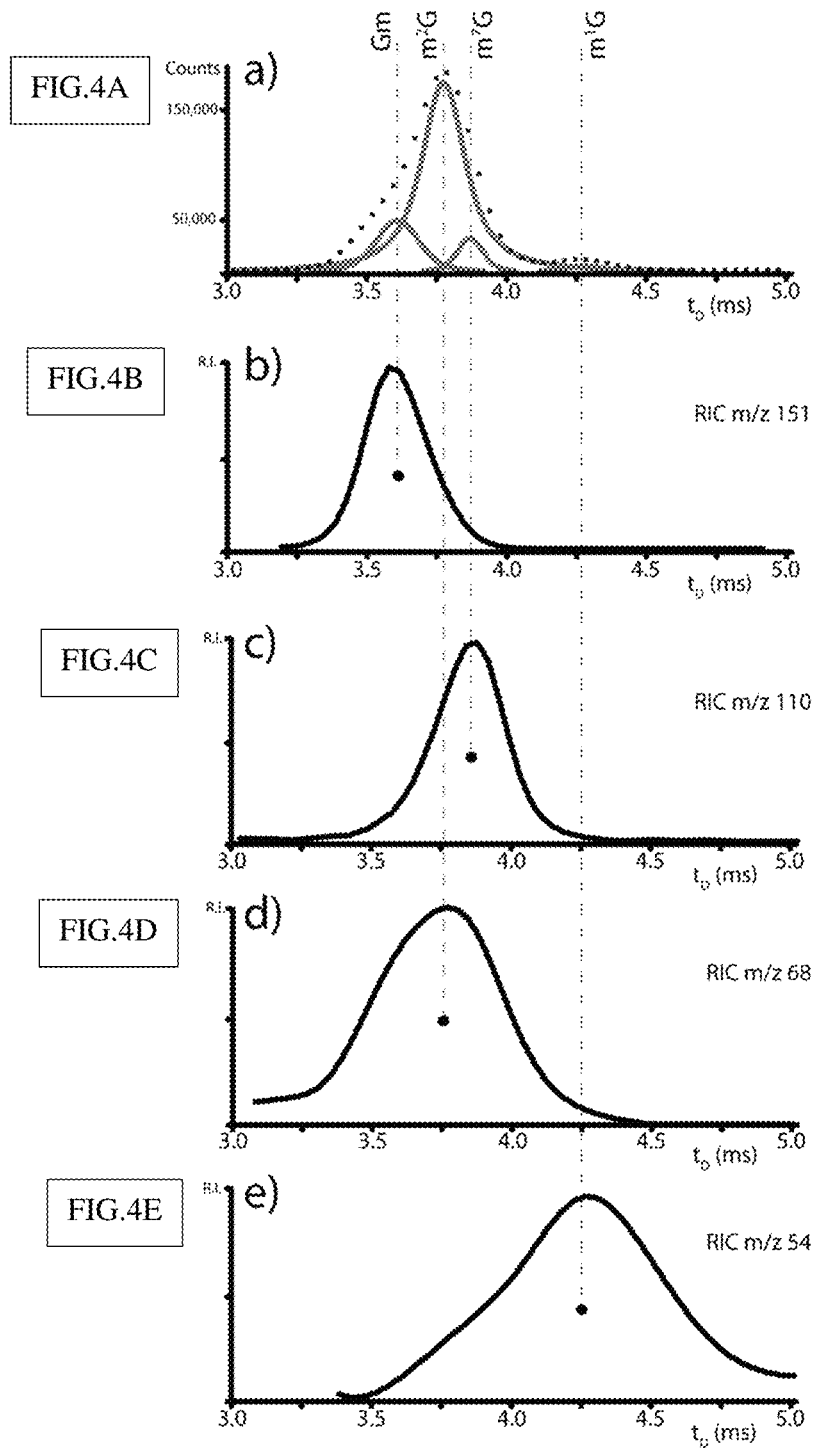

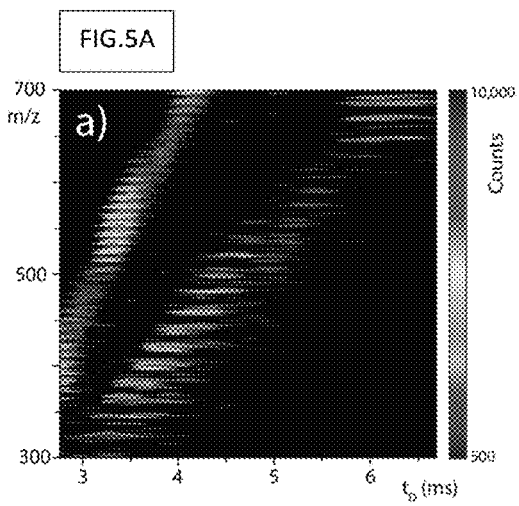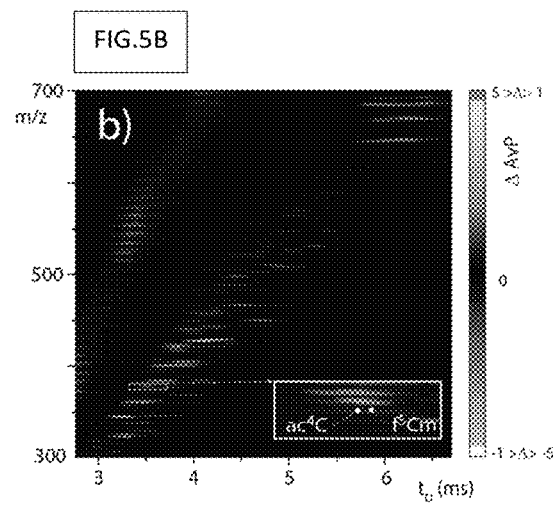
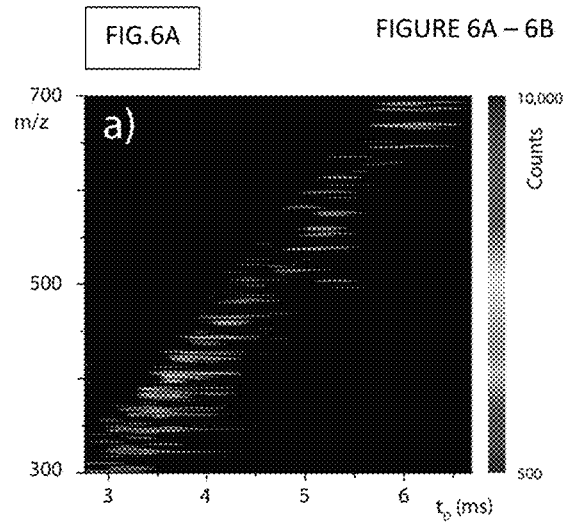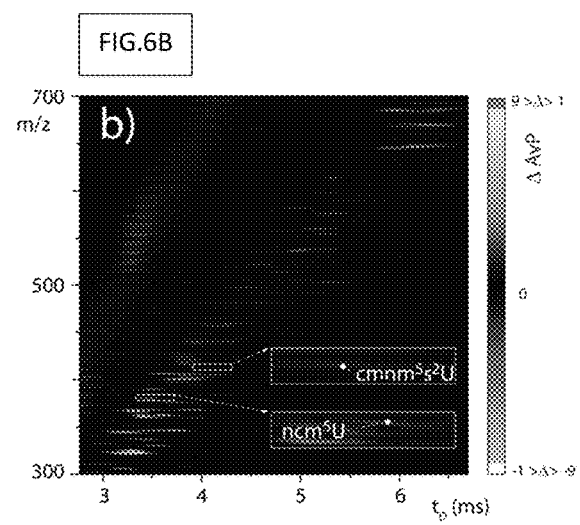
FIGURE 6A – 6B

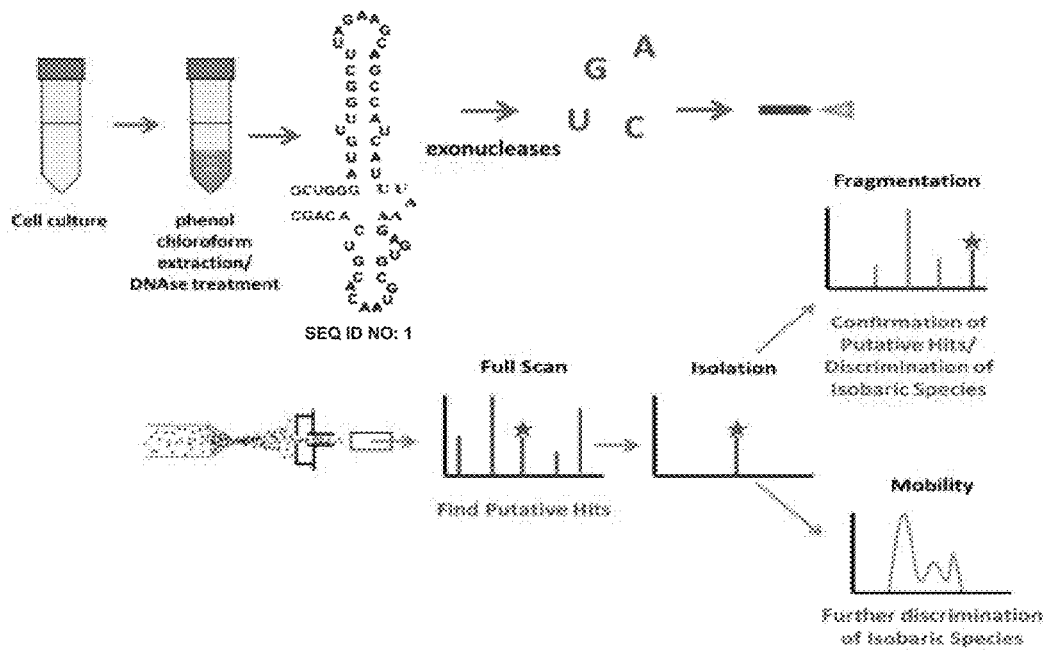
Figure 9A
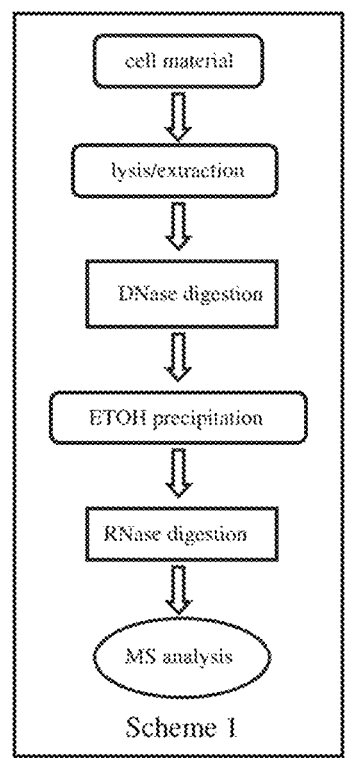
Scheme 1

FIGURE 9B
Mass Spectrometry:

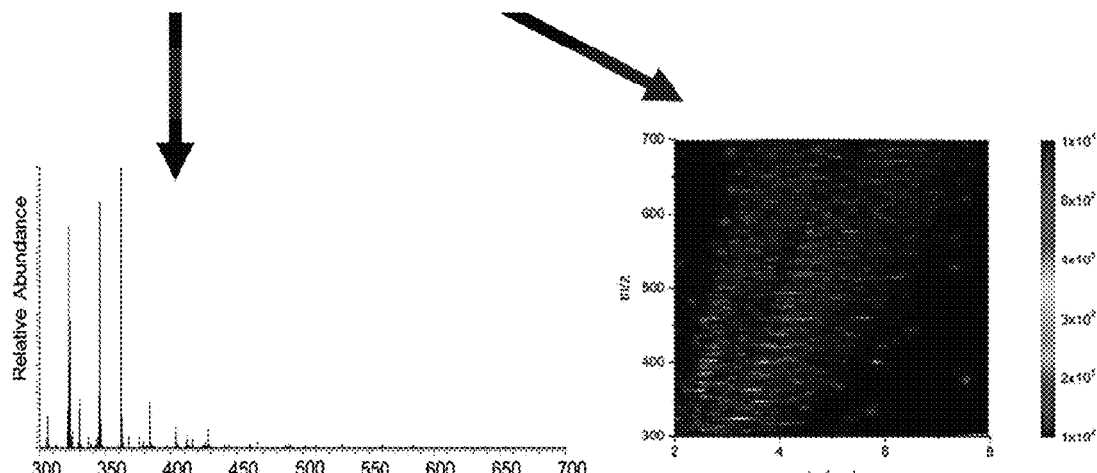

Representative ESI-MS spectrum of total RNA extract after exonuclease digestion

Representative heat map of RNA extract after exonuclease digestion shows overall complexity

The RNA Institute

METLIN

The RNA Modification Database

Modomics
a database of RNA modification pathways

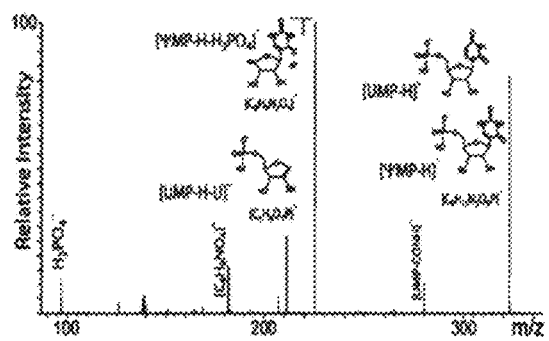

Tandem MS used to discriminate UMP and YMP by unique fragments

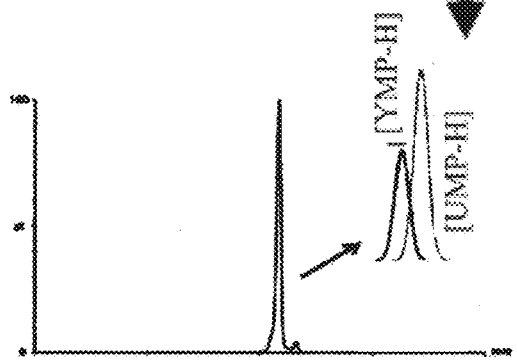

IMS-MS shows two distinct mobility profiles for UMP and YMP

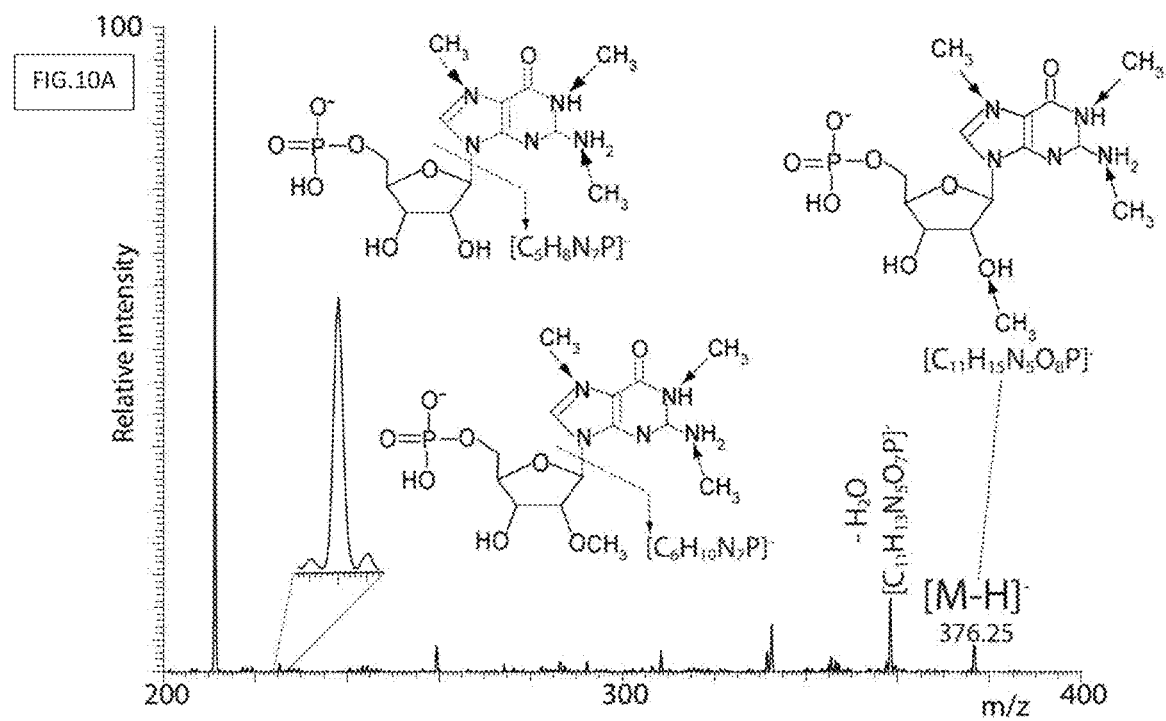
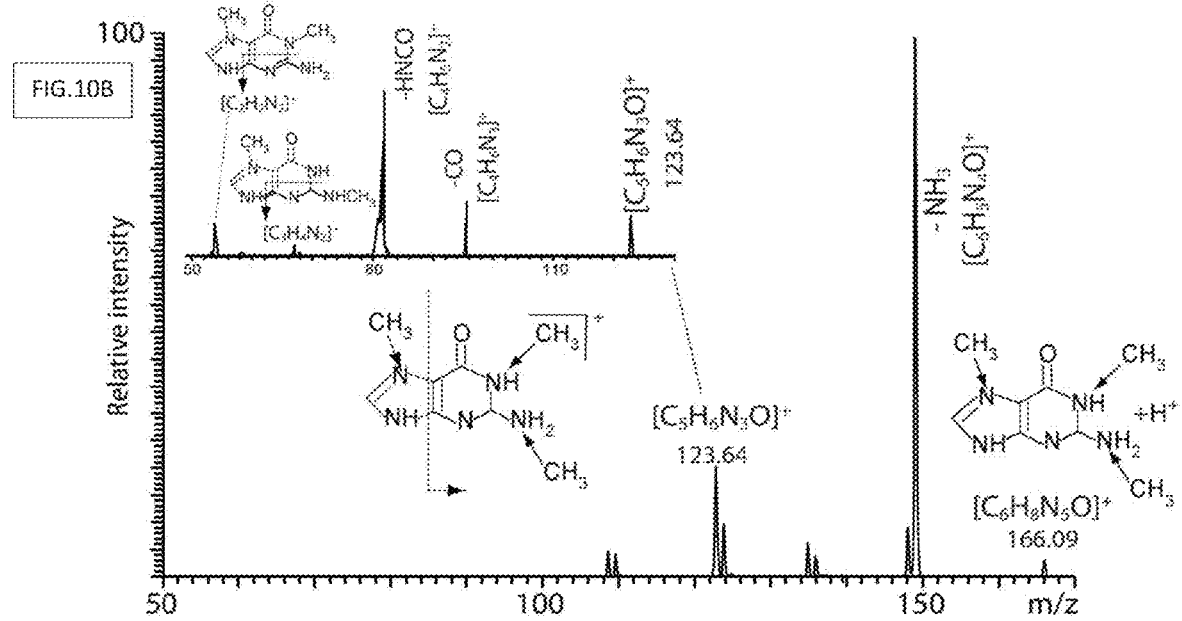

IMS-MS shows two distinct mobility profiles for UMP and YMP

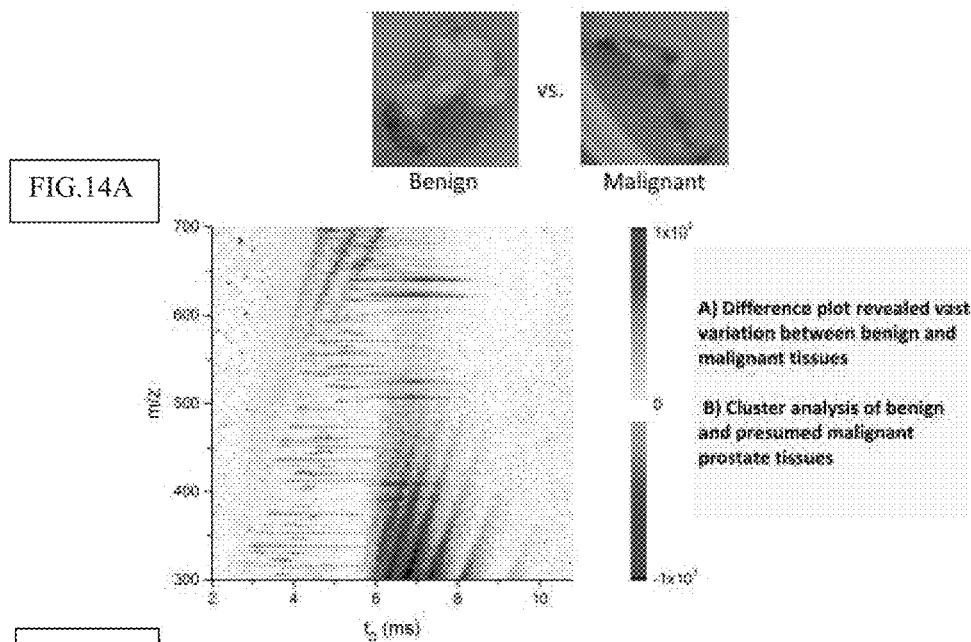
FIG.14A
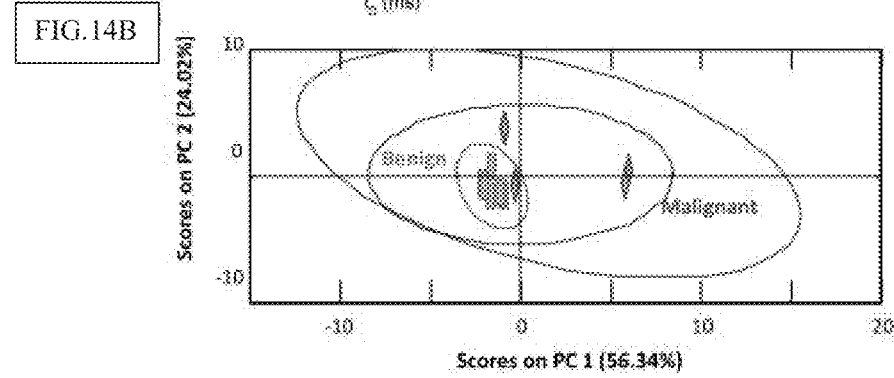
FIG.14B
FIG.14C
Benign        Malignant
FIG.14D
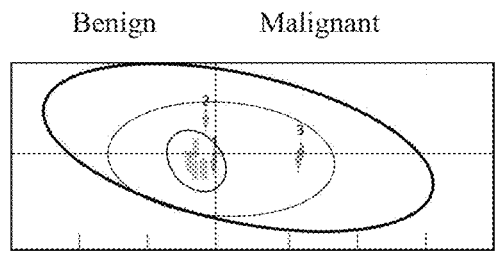
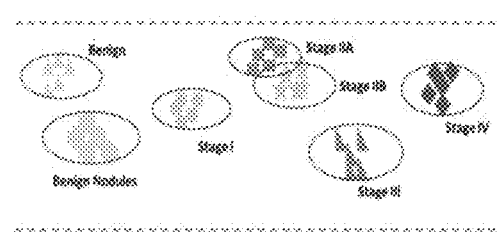

Captured material
SEQ ID NO: 1

*Analysis:*

*Analysis:*
- Gel Electrophoresis
- Mass Spectrometry

12% PAGE gel: Beads with probe vs Blank Beads

0.8% denaturing agarose gel: Total RNA used in Capture

0.8% denaturing agarose gel: Capture

- RNA was present in the Flowthrough and First Elution, but not in the washes.

Fig. 29

| Targeted Profiling | | | |
|---|---|---|---|
| Monoisotopic mass (Da) | Modification | Total RNA | mRNA |
| 323.052 | C | | |
| 324.036 | U, Y | | |
| 326.052 | D | | |
| 337.068 | $m^3C$, $m^5C$, Cm, $m^4C$ | | |
| 338.052 | Um, $m^2U$, $m^1Y$, Ym, $m^3U$, $m^3Y$ | | |
| 339.929 | $s^2C$ | | |
| 340.013 | $s^2U$, $s^4U$ | | |
| 340.031 | $ho^5U$ | | |
| 340.067 | $m^3D$ | | |
| 347.063 | A | | |
| 348.047 | I | | |
| 351.047 | $f^5C$ | | |
| 352.031 | $f^5U$ | | |
| 352.067 | $m^2Um$, $m^5Um$ | | |
| 353.062 | $hm^5C$, $nm^5U$ | | |
| 354.029 | $ni5s2U$, $s2Um$ | | |
| 354.046 | $mo^5U$ | | |
| 357.084 | Qbase | | |
| 361.079 | $m^1A$, $m^2A$, $m^6A$, Am, $m^8A$ | | |
| 362.063 | $m^1I$, Im | | |
| 363.058 | G | | |
| 364.042 | X | | |
| 365.062 | $ac^4C$, $f^5Cm$ | | |
| 365.099 | $m^4_2Cm$ | | |
| 366.046 | $f^5Um$ | | |
| 367.078 | $mnm^5U$ | | |
| 368.008 | $f^5s^2U$ | | |
| 369.040 | $nm^5s^2U$ | | |
| 375.094 | $m^6Am$ | | |
| 376.078 | $m^1Im$ | | |
| 377.074 | $m^1G$, $m^2G$, Gm | | |
| 379.078 | $ac^4Cm$ | | |
| 381.057 | $ncm^5U$ | | |
| 382.041 | $cm^5U$ | | |
| 383.055 | $mnm^5s^2U$ | | |
| 387.958 | $preQ_0$ | | |
| 389.074 | $ac^6A$ | | |
| 389.110 | $m^6_2Am$ | | |
| 391.089 | $m^1Gm$, $m^2_2G$, $m^2Gm$, $preQ_1$, $m^2_2G$ | | |
| 395.073 | $ncm^5Um$ | | |
| 396.057 | $mcm^5U$ | | |
| 398.036 | $cmo^5U$, $chm^5U$ | | |
| 401.074 | $imG$-14 | | |
| 404.085 | G+ | | |
| 405.105 | $m^2_2Gm$, $m^2_2{,}^7G$, $m^2_2Gm$ | | |
| 407.066 | $ms^2m^6A$ | | |
| 410.073 | $mcm^5Um$ | | |
| 411.068 | $cmnm^5U$ | | |
| 412.034 | $mcm^5s^2U$ | | |
| 415.089 | $imG^2$ | | |
| 415.126 | $i^6A$ | | |
| 495.869 | $f^5se^2U$ | | |
| 496.901 | $nm^5se^2U$ | | |
| 510.916 | $mnm^5se^2U$ | | |
| 554.906 | $cmnm^5se^2U$ | | |
| 559.072 | Ar(p) | | |
| 575.067 | Gr(p) | | |
| 588.158 | yW | | |
| 604.153 | OHyW | | |
| 618.169 | gluQ | | |
| 620.148 | $o^2yW$ | | |
| 651.179 | galQ, manQ | | |

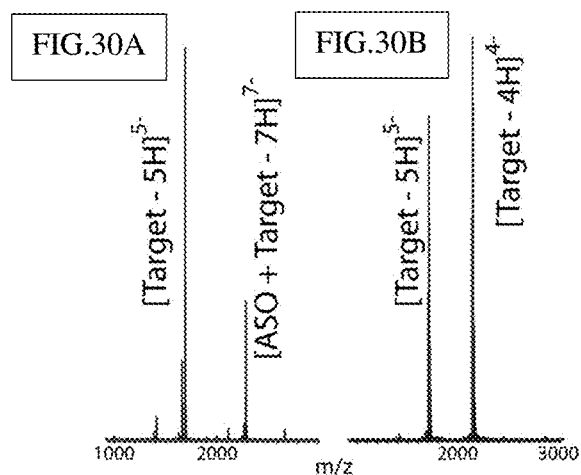
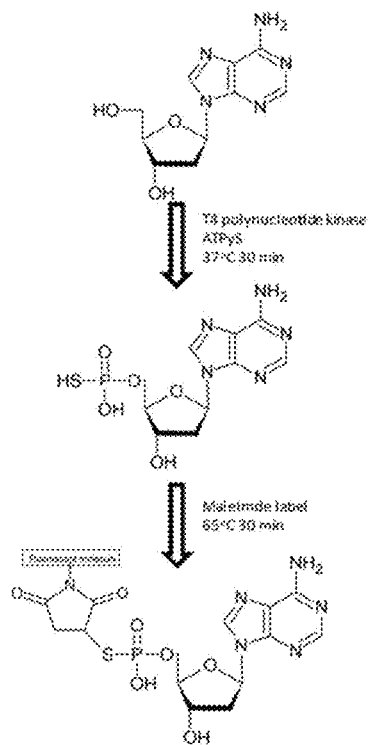
FIGURE 31

US 11,339,441 B2

PROFILING CHEMICALLY MODIFIED DNA/RNA UNITS FOR DISEASE AND CANCER DIAGNOSIS

GOVERNMENT INTERESTS

This invention was made with government support under Grant No. GM064328 awarded by the National Institutes of Health. The government has certain rights in the invention.

REFERENCE TO A SEQUENCE LISTING

This application contains a Sequence Listing in computer readable form. The contents of the electronic sequence listing (SEQUENCELISTING ST25.txt; size 2787 byte; and Date of Creation: Feb. 17, 2022) is herein incorporated by reference in its entirety.

FIELD OF THE INVENTION

The present invention relates to high-throughput methods comprising direct infusion electrospray ionization mass spectrometry (ESI-MS), multistep tandem mass spectrometry (MS"), consecutive reaction monitoring (CRM), ion mobility spectrometry mass spectrometry (IMS-MS), high-resolution MS, and IMS-MS, for genome-wide (whole cell or tissue) profiling of DNA and RNA nucleotides/nucleosides having a wide variety of variant structural modifications. In particular, these methods are contemplated for providing a specific profile of variant DNA and/or RNA chemically modified nucleic acids (i.e. structures) associated with specific medical conditions. Medical conditions may include, but are not limited to: cancer; including prostate, lung, uterus, larynx, ovary, breast, kidney, and many other types of cancers; specific stages of cancer; bacterial infections; viral infections; genetic and metabolic disorders; and any condition involving changes in DNA and/or RNA structural modifications.

BACKGROUND

DNA and RNA molecules can have numerous types of individual chemical structures. For example, over one hundred ribonucleotide post-transcriptional modifications (PTMs) and corresponding metabolic pathways are currently described in the RNA Modifications (Limbach et al., 1994; Cantara et al., 2011) and MODOMICS (Dunin-Horkawicz et al., 2006; Machnicka et al., 2012) databases. Post-transcriptional modifications (PTMs) are introduced by the activity of specialized enzymes (Ferré-D'Amaré, 2003). However, with the exception of a handful of PTMs involved in molecular recognition and stabilization of RNA structure (Kowalak et al., 1994; Ofengand, 2002; Helm, 2006), their biological function is unknown. As one example of a known function, an individual RNA molecule may be chemically altered by methylation of the 3' nucleotide, which has been discovered to protect miRNAs from uridylation, a prelude to exonucleolytic degradation (Li et al., 2005).

In order to identify a nucleic acid having a specific modification, each modification has a targeted analytical approach, for example based on bisulfite chemistry (Frommer et al., 1992; Herman et al., 1996) or specific restriction enzymes (Singer-Sam et al., 1990; Issa et al., 1994), which enable the detection of methylation sites by high-throughput sequencing techniques (Ajay et al., 2011; Koboldt et al., 2013). There are no high-throughput approaches for the majority of other PTMs. For this reason, their functional elucidation has been severely hampered by the inability to detect, locate, and track their levels as a function of predetermined experimental factors.

The appearance and/or disappearance of certain types of nucleic acid structures are found associated with specific medical conditions. However, current analytical methods rarely if ever identify small groups or patterns (i.e. profiles) of modified nucleic acid structures associated with a specific disease, stage of a disease or infection. Further, the results of profiling variant nucleic acids within a cell are typically too ambiguous for use in providing a diagnosis for medical use.

Therefore, a more accurate method of identifying and associating patterns of nucleic acids having variant chemical structural modifications with infections and disease would be of use.

SUMMARY OF THE INVENTION

The present invention relates to high-throughput methods comprising direct infusion electrospray ionization mass spectrometry (ESI-MS), multistep tandem mass spectrometry (MS"), consecutive reaction monitoring (CRM), ion mobility spectrometry mass spectrometry (IMS-MS), high-resolution MS, and IMS-MS, for genome-wide (whole cell or tissue) profiling of DNA and RNA nucleotides/nucleosides having a wide variety of variant structural modifications. In particular, these methods are contemplated for providing a specific profile of variant DNA and/or RNA chemically modified nucleic acids (i.e. structures) associated with specific medical conditions. Medical conditions may include, but are not limited to: cancer; including prostate, lung, uterus, larynx, ovary, breast, kidney, and many other types of cancers; specific stages of cancer; bacterial infections; viral infections; genetic and metabolic disorders; and any condition involving changes in DNA and/or RNA structural modifications.

Accordingly, in some embodiments, the present invention provides a method for identifying a profile of nucleic acid structures in a cell, comprising: (a) providing, (i) a mononucleotide mixture from a cell, said cell comprising at least two or more individual nucleic acids having a molecular mass, and (ii) a mass spectrometer; (b) determining molecular masses of said mononucleotides with said mass spectrometer by measuring molecular masses of one or more of said mononucleotide; (c) identifying the presence of a particular nucleic acid structure; and (d) repeating steps b-c (as necessary) so as to identify a profile of modified nucleotide structures in said cell. In one embodiment, the method further provides (iii) a source of reference structural data for mononucleotides having variant structures. In one embodiment, the method further comprises a step in between step (b) and (c), comparing one or more of said molecular masses with said source of reference structural data for mononucleotides having variant structures. In one embodiment, said mononucleotide is a ribonucleotide (RNA). In one embodiment, said mononucleotide is a ribonucleotide (RNA). In one embodiment, said ribonucleotide structure is a previously unknown structure. In one embodiment, said ribonucleotide structure has a previously unknown molecular mass. In one embodiment, said profile includes a previously unknown modified RNA structure. In one embodiment, said profile includes at least one unique modified RNA structure characteristic of said cell. In one embodiment, said mononucleotide is a deoxyribonucleotide (DNA). In one embodiment, said deoxyribonucleotide structure is a previously unknown structure. In one embodiment, said deoxyribonucleotide structure has a previously unknown molecular mass. In one embodiment, said profile includes a previously unknown modified DNA structure. In one embodiment, said profile includes at least one unique modified DNA structure characteristic of said cell. In one embodiment, said cell is a mammalian cell. In one embodiment, said cell is part of a tissue. In one embodiment, said cell is any type of cell, such as a prostate cell, or organism, such as a yeast or bacteria cell. In one embodiment, said cell is selected from the group consisting of a single cell microorganism, a control cell, a healthy cell, a cancer cell, an infected cell and a stressed cell. In one embodiment, said cancer includes but is not limited to prostate, lung, uterus, larynx, ovary, breast, kidney, and many other types of cancers. In one embodiment, said profile is used to identify said cell. In one embodiment, said mass spectrometer comprises ion mobility spectrometry-mass spectrometry (IMS-MS). In one embodiment, said mass spectrometer further comprises high-resolution mass spectrometry. In one embodiment, said mass spectrometry is a direct infusion electrospray ionization (ESI) mass spectrometer in nanoflow ESI mode. In one embodiment, said method further comprises consecutive reaction monitoring (CRM). In one embodiment, said mass spectrometer comprises $MS^n$ analyses. In one embodiment, said mass spectrometer comprises tandem mass spectrometry (MS/MS). In one embodiment, said method further comprises high-resolution determinations. In one embodiment, a heat-map plot is derived from said mass spectrometer then used to identify an isobaric modified nucleic acid for including in said profile.

In one embodiment, the invention provides a method for identifying a profile of ribonucleotide (RNA) nucleic acid structures in a biopsy tissue, comprising: (a) providing, (i) a mixture of individual ribonucleotides from a biopsy tissue, said biopsy tissue comprising at least two or more individual ribonucleic acids having a molecular mass; and (ii) a mass spectrometer; (b) determining molecular masses of said individual ribonucleotides with said mass spectrometer; (c) identifying the presence of a particular ribonucleic acid structure and modification thereof then including said structure as part of a profile of ribonucleic acids structures in said biopsy tissue. In one embodiment, the method further provides (iii) a source of reference structural data for ribonucleotides having variant structures. In one embodiment, the method further comprises a step in between step (b) and (c), comparing one or more of said molecular masses with said source of reference structural data for individual ribonucleic acids having variant structures. In one embodiment, said ribonucleotide structure is a previously unknown structure. In one embodiment, said ribonucleotide structure has a previously unknown molecular mass. In one embodiment, said profile includes a previously unknown modified RNA structure. In one embodiment, said biopsy tissue is from an organ. Organs include but are not limited to blood, skin, reproductive, prostate lung, uterus, larynx, ovary, breast, kidney, etc. Thus, in one embodiment, said organ is selected from the group consisting of blood, skin, reproductive, prostate, lung, uterus, larynx, ovary, breast, and kidney. In one embodiment, said profile of modified nucleotide structures in said tissue identifies a medical state selected from the group consisting of, a healthy tissue, a benign cancer tissue, a malignant cancer tissue, a staged cancer tissue, an infected tissue, and a stressed tissue. In one embodiment, said cancer includes but is not limited to prostate, lung, uterus, larynx, ovary, breast, kidney, and many other types of cancers. In one embodiment, a first heat-map plot is derived from said mass spectrometer for providing a first profile of said tissue. In one embodiment, said first profile of said first tissue is compared to a second profile derived from a second tissue sample of a second mixture of individual ribonucleotides for identifying said tissue selected from the group consisting of a healthy tissue, a benign cancer tissue, a malignant cancer tissue, an infected tissue, and a stressed tissue. In one embodiment, said mass spectrometer comprises ion mobility spectrometry-mass spectrometry (IMS-MS). In one embodiment, said mass spectrometer further comprises high-resolution mass spectrometry. In one embodiment, said mass spectrometry is a direct infusion electrospray ionization (ESI) mass spectrometer in nanoflow ESI mode. In one embodiment, said method further comprises consecutive reaction monitoring (CRM). In one embodiment, said mass spectrometer comprises $MS^n$ analyses. In one embodiment, said mass spectrometer comprises tandem mass spectrometry (MS/MS). In one embodiment, said method further comprises high-resolution determinations. In one embodiment, a heat-map plot is derived from said mass spectrometer then used to identify an isobaric modified nucleic acid for including in said profile. In one embodiment, a first heat-map plot is derived from said mass spectrometer for providing a first cluster map of said tissue. In one embodiment, said first cluster map of a said first tissue is compared to a second cluster map derived from a second tissue sample of a second mixture of individual ribonucleotides for identifying said tissue selected from the group consisting of a healthy tissue, a benign cancer tissue, a staged cancer tissue, a malignant cancer tissue, an infected tissue, and a stressed tissue.

In one embodiment, the invention provides a method for identifying a profile of deoxyribonucleotide (DNA) nucleic acid structures in a biopsy tissue, comprising: (a) providing, (i) a mixture of individual deoxyribonucleotides from a biopsy tissue, said biopsy tissue comprising at least two or more individual deoxyribonucleic acids having a molecular mass; and (ii) a mass spectrometer; (b) determining molecular masses of said individual deoxyribonucleotides with said mass spectrometer; (c) identifying the presence of a particular deoxyribonucleic acid structure and modification thereof then including said structure as part of a profile of deoxyribonucleic acids structures in said biopsy tissue. In one embodiment, the method further provides (iii) a source of reference structural data for deoxyribonucleotides having variant structures. In one embodiment, the method further comprises a step in between step (b) and (c), comparing one or more of said molecular masses with said source of reference structural data for individual deoxyribonucleic acids having variant structures. In one embodiment, said deoxyribonucleotide structure is a previously unknown structure. In one embodiment, said deoxyribonucleotide structure has a previously unknown molecular mass. In one embodiment, said profile includes a previously unknown modified DNA structure. In one embodiment, said biopsy tissue is from an organ. Organs include but are not limited to blood, skin, reproductive, prostate lung, uterus, larynx, ovary, breast, kidney, etc. Thus, in one embodiment, said organ is selected from the group consisting of blood, skin, reproductive, prostate, lung, uterus, larynx, ovary, breast, and kidney. In one embodiment, said profile of modified nucleotide structures in said tissue identifies a medical state selected from the group consisting of, a healthy tissue, a benign cancer tissue, a malignant cancer tissue, a staged cancer tissue, an infected tissue, and a stressed tissue. In one embodiment, said cancer includes but is not limited to prostate, lung, uterus, larynx, ovary, breast, kidney, and many other types of cancers. In one embodiment, said mass spectrometer comprises ion mobility spectrometry-mass spectrometry (IMS-MS). In one embodiment, said mass spectrometer further comprises high-resolution mass spectrometry. In one embodiment, said mass spectrometry is a direct infusion electrospray ionization (ESI) mass spectrometer in nanoflow ESI mode. In one embodiment, said method further comprises consecutive reaction monitoring (CRM). In one embodiment, said mass spectrometer comprises MS" analyses. In one embodiment, said mass spectrometer comprises tandem mass spectrometry (MS/MS). In one embodiment, said method further comprises high-resolution determinations. In one embodiment, a heat-map plot is derived from said mass spectrometer then used to identify an isobaric modified nucleic acid for including in said profile. In one embodiment, a first heat-map plot is derived from said mass spectrometer for providing a first profile of said tissue. In one embodiment, said first profile of said first tissue is compared to a second profile derived from a second tissue sample of a second mixture of individual deoxyribonucleotides for identifying said tissue selected from the group consisting of a healthy tissue, a benign cancer tissue, a malignant cancer tissue, an infected tissue, and a stressed tissue. In one embodiment, a first heat-map plot is derived from said mass spectrometer for providing a first cluster map of said tissue. In one embodiment, said first cluster map of a said first tissue is compared to a second cluster map derived from a second tissue sample of a second mixture of individual deoxyribonucleotides for identifying said tissue selected from the group consisting of a healthy tissue, a benign cancer tissue, a staged cancer tissue, a malignant cancer tissue, an infected tissue, and a stressed tissue.

In one embodiment, the invention provides a method for identifying a profile of ribonucleotide (RNA) nucleic acid structures in a prostate biopsy tissue, comprising: (a) providing, (i) a mixture of individual ribonucleotides from a prostate biopsy tissue, said biopsy tissue comprising at least two or more individual ribonucleic acids having a molecular mass; and (ii) a mass spectrometer; (b) determining molecular masses of said individual ribonucleotides with said mass spectrometer; (c) identifying the presence of a particular ribonucleic acid structure and modification thereof then including said structure as part of a profile of ribonucleic acids structures in said prostate biopsy tissue. In one embodiment, the method further provides (iii) a source of reference structural data for ribonucleotides having variant structures. In one embodiment, the method further comprises a step in between step (b) and (c), comparing one or more of said molecular masses with said source of reference structural data for individual ribonucleic acids having variant structures. In one embodiment, said ribonucleotide structure is a previously unknown structure. In one embodiment, said ribonucleotide structure has a previously unknown molecular mass. In one embodiment, said profile includes a previously unknown modified RNA structure. In one embodiment, said profile of modified nucleotide structures in said tissue identifies a medical state selected from the group consisting of, a healthy prostate tissue, a benign cancer prostate tissue, a malignant cancer prostate tissue, and a staged cancer prostate tissue. In one embodiment, said mass spectrometer comprises ion mobility spectrometry-mass spectrometry (IMS-MS). In one embodiment, said mass spectrometer further comprises high-resolution mass spectrometry. In one embodiment, said mass spectrometry is a direct infusion electrospray ionization (ESI) mass spectrometer in nanoflow ESI mode. In one embodiment, said method further comprises consecutive reaction monitoring (CRM). In one embodiment, said mass spectrometer comprises MS" analyses. In one embodiment, said mass spectrometer comprises tandem mass spectrometry (MS/MS). In one embodiment, said method further comprises high-resolution determinations. In one embodiment, a heat-map plot is derived from said mass spectrometer then used to identify an isobaric modified nucleic acid for including in said profile. In one embodiment, a first heat-map plot is derived from said mass spectrometer for providing a first profile of said tissue. In one embodiment, said first profile of said first tissue is compared to a second profile derived from a second tissue sample of a second mixture of individual ribonucleotides for identifying said tissue selected from the group consisting of a healthy tissue, a benign cancer prostate tissue, a staged prostate cancer prostate tissue, and a malignant cancer prostate tissue. In one embodiment, a first heat-map plot is derived from said mass spectrometer for providing a first cluster map of said prostate tissue. In one embodiment, said first cluster map of a said first prostate tissue is compared to a second cluster map derived from a second prostate tissue sample of a second mixture of individual ribonucleotides for identifying said prostate tissue selected from the group consisting of a healthy prostate tissue, a benign cancer prostate tissue, a staged cancer prostate tissue, and a malignant cancer prostate tissue.

In one embodiment, the invention provides a method for identifying ribonucleotide (RNA) structures in a biopsy tissue, comprising: (a) providing, (i) a mixture of individual ribonucleotides from a biopsy tissue, said tissue comprising at least two or more individual ribonucleic acids having a molecular mass; (ii) a mass spectrometer; and (b) determining molecular masses of said ribonucleotides with said mass spectrometer by measuring molecular masses of one or more of said ribonucleotides; and (c) identifying the presence of a particular ribonucleic acid structure and modification thereof then including said structure as part of a profile of ribonucleic acids structures in said biopsy tissue. In one embodiment, the method further provides (iii) a source of reference structural data for ribonucleotides having variant structures. In one embodiment, the method further comprises a step in between step (b) and step (c), comparing one or more of said molecular masses with said source of reference structural data for individual ribonucleic acids having variant structures. In one embodiment, said ribonucleotide structure is a previously unknown structure. In one embodiment, said ribonucleotide structure has a previously unknown molecular mass. In one embodiment, said profile includes a previously unknown modified RNA structure. In one embodiment, said profile of modified nucleotide structures in said biopsy tissue associates with a medical stage including but not limited to a healthy tissue, a benign cancer tissue, a staged cancer tissue, and a malignant cancer tissue. In one embodiment, said profile of modified nucleotide structures is selected from the group consisting of a healthy tissue, a benign cancer tissue, a staged cancer tissue, and a malignant cancer tissue. In one embodiment, said mass spectrometer comprises ion mobility spectrometry-mass spectrometry (IMS-MS). In one embodiment, said mass spectrometer further comprises high-resolution mass spectrometry. In one embodiment, said mass spectrometry is a direct infusion electrospray ionization (ESI) mass spectrometer in nanoflow ESI mode. In one embodiment, said method further comprises consecutive reaction monitoring (CRM). In one embodiment, said mass spectrometer comprises MS" analyses. In one embodiment, said mass spectrometer comprises tandem mass spectrometry (MS/MS). In one embodiment, said method further comprises high-resolution determinations. In one embodiment, a heat-map plot is derived from said mass spectrometer then used to identify an isobaric modified nucleic acid for including in said profile. In one embodiment, the method further provides a first heat-map plot derived from said mass spectrometer for providing a first cluster map of said tissue. In one embodiment, said first cluster map is compared to a second cluster map derived from a second biopsy sample of a second mixture of individual ribonucleotides providing a second heat-map for identifying a medical stage selected from the group consisting of a healthy tissue, a benign cancer tissue, a staged cancer tissue, and a malignant cancer tissue. In one embodiment, said cancer includes but is not limited to prostate, lung, uterus, larynx, ovary, breast, kidney, and many other types of cancers. In one embodiment, said cancer is selected from the group consisting of prostate, lung, uterus, larynx, ovary, breast, and kidney.

In one embodiment, the invention provides a method for identifying deoxyribonucleotide (DNA) structures in a biopsy tissue, comprising: (a) providing, (i) a mixture of individual deoxyribonucleotides from a biopsy tissue, said tissue comprising at least two or more individual deoxyribonucleic acids having a molecular mass; (ii) a mass spectrometer; and (b) determining molecular masses of said deoxyribonucleotides with said mass spectrometer by measuring molecular masses of one or more of said deoxyribonucleotides; and (c) identifying the presence of a particular deoxyribonucleic acid structure and modification thereof then including said structure as part of a profile of deoxyribonucleic acids structures in said biopsy tissue. In one embodiment, the method further provides (iii) a source of reference structural data for deoxyribonucleotides having variant structures. In one embodiment, the method further comprises a step in between step (b) and step (c), comparing one or more of said molecular masses with said source of reference structural data for individual deoxyribonucleic acids having variant structures. In one embodiment, said deoxyribonucleotide structure is a previously unknown structure. In one embodiment, said deoxyribonucleotide structure has a previously unknown molecular mass. In one embodiment, said profile includes a previously unknown modified RNA structure. In one embodiment, said profile of modified deoxyribonucleotide structures in said biopsy tissue associates with a medical stage including but not limited to a healthy tissue, a benign cancer tissue, a staged cancer tissue, and a malignant cancer tissue. In one embodiment, said profile of modified nucleotide structures is selected from the group consisting of a healthy tissue, a benign cancer tissue, a staged cancer tissue, and a malignant cancer tissue. In one embodiment, said mass spectrometer comprises ion mobility spectrometry-mass spectrometry (IMS-MS). In one embodiment, said mass spectrometer further comprises high-resolution mass spectrometry. In one embodiment, said mass spectrometry is a direct infusion electrospray ionization (ESI) mass spectrometer in nanoflow ESI mode. In one embodiment, said method further comprises consecutive reaction monitoring (CRM). In one embodiment, said mass spectrometer comprises $MS^n$ analyses. In one embodiment, said mass spectrometer comprises tandem mass spectrometry (MS/MS). In one embodiment, said method further comprises high-resolution determinations. In one embodiment, a heat-map plot is derived from said mass spectrometer then used to identify an isobaric modified nucleic acid for including in said profile. In one embodiment, the method further provides a first heat-map plot derived from said mass spectrometer for providing a first cluster map of said tissue. In one embodiment, said first cluster map is compared to a second cluster map derived from a second biopsy sample of a second mixture of individual deoxyribonucleotides providing a second heat-map for identifying a medical stage selected from the group consisting of a healthy tissue, a benign cancer tissue, a staged cancer tissue, and a malignant cancer tissue. In one embodiment, said cancer includes but is not limited to prostate, lung, uterus, larynx, ovary, breast, kidney, and many other types of cancers. In one embodiment, said cancer is selected from the group consisting of prostate, lung, uterus, larynx, ovary, breast, and kidney. In one embodiment, said cancer is prostate cancer.

In one embodiment, the invention provides a method for identifying ribonucleotide (RNA) structures in a prostate biopsy tissue, comprising: (a) providing, (i) a mixture of individual ribonucleotides from a prostate biopsy tissue, said tissue comprising at least two or more individual ribonucleic acids having a molecular mass; (ii) a mass spectrometer; and (b) determining molecular masses of said ribonucleotides with said mass spectrometer by measuring molecular masses of one or more of said ribonucleotides; and (c) identifying the presence of a particular ribonucleic acid structure and modification thereof then including said structure as part of a profile of ribonucleic acids structures in said prostate biopsy tissue. In one embodiment, the method further provides (iii) a source of reference structural data for ribonucleotides having variant structures. In one embodiment, the method further comprises a step in between step (b) and step (c), comparing one or more of said molecular masses with said source of reference structural data for individual ribonucleic acids having variant structures. In one embodiment, said ribonucleotide structure is a previously unknown structure. In one embodiment, said ribonucleotide structure has a previously unknown molecular mass. In one embodiment, said profile includes a previously unknown modified RNA structure. In one embodiment, said profile of modified nucleotide structures in said prostate biopsy tissue associates with a medical stage selected from the group consisting of a healthy prostate tissue, a benign prostate cancer tissue, a staged prostate cancer tissue, and a malignant prostate cancer tissue. In one embodiment, said mass spectrometer comprises ion mobility spectrometry-mass spectrometry (IMS-MS). In one embodiment, said mass spectrometer further comprises high-resolution mass spectrometry. In one embodiment, said mass spectrometry is a direct infusion electrospray ionization (ESI) mass spectrometer in nanoflow ESI mode. In one embodiment, said method further comprises consecutive reaction monitoring (CRM). In one embodiment, said mass spectrometer comprises $MS^n$ analyses. In one embodiment, said mass spectrometer comprises tandem mass spectrometry (MS/MS). In one embodiment, said method further comprises high-resolution determinations. In one embodiment, a heat-map plot is derived from said mass spectrometer then used to identify an isobaric modified nucleic acid for including in said profile. In one embodiment, the method further provides a first heat-map plot derived from said mass spectrometer for providing a first cluster map of said tissue. In one embodiment, said first cluster map is compared to a second cluster map derived from a second prostate biopsy sample of a second mixture of individual ribonucleotides providing a second heat-map for identifying a medical stage selected from the group consisting of a healthy prostate tissue, a benign prostate cancer tissue, a staged prostate cancer tissue, and a malignant prostate cancer tissue.

Definitions

To facilitate an understanding of the present invention, a number of terms and phrases are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration.

As used herein, the term "epitranscriptomic" refers to the entire complement of RNAs synthesized in an organism or tissue or cell, including protein-coding, non-protein-coding, alternatively spliced, alternatively polyadenylated, alternatively initiated, sense, antisense, RNA-edited transcripts, RNA nucleotides as part of transcribed RNA molecules and RNA nucleotides isolated from RNA strands. Such RNA molecules may have a modification corresponding to at least one of the 110 RNA+ known modifications, such as methyl-6-adenosine ($m^6A$), and may include at least one new (i.e. previously unknown) modification. Epigenetics refers to relevant changes to the genome that do not involve a change in the nucleotide sequence. Epitranscriptomics refers to changes to the transcriptome that do not involve a change in the ribonucleotide sequence. An epitranscriptome, therefore, is defined as the ensemble of such changes.

Modified nucleic acids may include (but are not limited to) one or more of: (i) alteration, e.g., replacement, of one or both of the non-linking phosphate oxygens and/or of one or more of the linking phosphate oxygens in the phosphodiester backbone linkage. (ii) alteration, e.g., replacement, of a constituent of the ribose sugar (for RNA), e.g., of the 2' hydroxyl on the ribose sugar; (iii) wholesale replacement of the phosphate moiety with "dephospho" linkers; (iv) modification or replacement of a naturally occurring base with a non-natural base; (v) modification or replacement (substitution) of a naturally occurring base with either a larger or a smaller ring systems; (vi) chemical modification of at least one functional group present on the nucleobase ring system; (vii) substitution or addition of at least one functional group to at least one position of the nucleobase ring system; (viii) replacement or modification of the ribose-phosphate backbone; (ix) modification of the 3' end or 5' end of the oligonucleotide, e.g., removal, modification or replacement of a terminal phosphate group or conjugation of a moiety, e.g., a fluorescently labeled moiety, to either the 3" or 5' end of oligonucleotide; and (x) modification of the sugar (e.g., additional membered rings, as in linked nucleic acids (LNA).

As used herein, the term "deoxyribonucleic acid" or "DNA" in reference to a nucleic acid refers to a molecule comprising three parts: a phosphate group, a sugar group (deoxyribose) and one of at least four types of nitrogen bases: adenine (A), thymine (T), guanine (G) and cytosine (C).

As used herein, the term "variant DNA" in reference to a deoxyribonucleic acid refers to a DNA molecule or DNA structure having at least one chemical modification, as one example, a 5-methylcytosine ($m^5C$) modified DNA structure.

As used herein, the term "modified DNA" may refer to a modification after the nucleic acid chain is polymerized, such as for example a 5-methylcytosine ($m^5C$) modified DNA structure, in which the nucleobase of a specific nucleotide in the biopolymer is modified.

As used herein, the term "ribonucleic acid" or "RNA" in reference to a nucleic acid refers to a molecule comprising at least three parts: a phosphate group, a ribose sugar group and one of at least four types of basic nitrogen bases or nucleosides: adenine (A), cytosine (C), guanine (G), and uracil (U). RNA includes any type of RNA, including but not limited to tRNA, mRNA, rRNA, tmRNA, snRNA, chromosomal RNA, non-coding RNA, and post-transcriptional RNA (PTM).

As used herein, the term "RNA modification" in reference to a ribonucleotide includes but is not limited to modifications to include a hypoxanthine and/or xanthine, two of the many bases created through mutagen presence, both of them through deamination (replacement of the amine-group with a carbonyl-group). Hypoxanthine is also produced from adenine, xanthine is also produced from guanine. In a similar manner, deamination of cytosine results in uracil. Additional nucleosides found in RNAs include but are not limited to pseudouridine ($\Psi$), dihydrouridine (D), inosine (I), and 7-methylguanosine ($m^7G$). There are over 110 known natural RNA modifications.

As used herein, the term "PTM" or "post-transcriptional modifications" in reference to a nucleotide, refers to a modification of an RNA nucleotide after transcription (i.e., after a DNA template is "copied" into a complementary RNA sequence). Currently, there are at least 110 known natural modifications.

As used herein, the term "variant structural modifications" in reference to a nucleic acid molecule refers to any structure that is different from another structure.

As used herein, the term "nucleotide" or "nucleotide residue" refers to an organic molecule that serves as a monomer, or subunit, of nucleic acids such as DNA and RNA. A nucleotide comprises a nucleobase, a five-carbon sugar, and one or more phosphate groups.

As used herein, the term "nucleobase" or "nitrogenous base" refers to a heterocyclic base containing nitrogen that forms the base part of nucleotide molecules.

As used herein, the term "ribose" in reference to a sugar is an organic compound with the formula $C_5H_{10}O_5$.

As used herein, the term "nucleoside" refers to a nucleotide without a phosphate group. In other words, a nucleoside comprises a nucleobase and a 5-carbon sugar (either ribose or deoxyribose) such that the base is bound to either ribose or deoxyribose via a beta-glycosidic linkage. Examples of nucleosides include cytidine, uridine, adenosine, guanosine, thymidine and inosine.

As used herein, the term "purine-bases" refer to base structures including two fused rings, such as adenine, guanine, and many other known variants.

As used herein, the term "pyrimidine-bases" refer to base structures including a single five-member ring, such as cytosine, uracil, thymine, and many other known variants.

As used herein, the term "mononucleotide" refers to individual nucleotide bases, i.e. individual nucleotides.

As used herein, the term "oligonucleotide" refers to a short, single-stranded DNA or RNA molecule, as one example, ranging from 2-200 nucleotide residues. Oligonucleotides readily bind, in a sequence-specific manner, to their respective complementary oligonucleotides, DNA, or RNA to form duplexes. Oligonucleotides composed of 2'-deoxyribonucleotides (oligodeoxyribonucleotides) are fragments of DNA and are often used in the polymerase chain reaction, a procedure that can greatly amplify almost any small amount of DNA. For PCR, the oligonucleotide is referred to as a primer allowing DNA polymerase to extend the oligonucleotide and replicate the complementary strand.

As used herein, the term "antisense probe" or "antisense oligonucleotide" refers to a single strand of DNA or RNA that is complementary to a chosen sequence. Antisense DNA can be used to target a specific, complementary (coding or non-coding) RNA.

As used herein, the term "complementary" or "complementary base pairs" in reference to a DNA or RNA sequence refers to pairing of hydrogen bonded nucleotides, such as pairings of A-U, G-C, or G-U in RNA strands; G:C and A:T in DNA strands.

As used herein, the term "profiling of nucleotides" in reference to genomic (whole cell or tissue) profiling, refers to the complement of nucleotide structures isolated from a sample, such as variant DNA and/or RNA chemically modified nucleic acids (i.e. structures) associated with medical conditions.

As used herein, the term "genome-wide" or "whole cell" or "whole tissue" refers to profiling of DNA and RNA nucleotides/nucleosides present in the total complement of nucleic acids in the cell or tissue, which may display a wide variety of variant structural modifications.

As used herein, the term "mass spectrometry" in reference to a method, refers to an analytical technique that can provide both qualitative (structure) and quantitative (molecular mass or concentration) information on analyte molecules after their conversion to ions. The molecules of interest are first introduced into the ionization source of the mass spectrometer, where they are first ionized to acquire positive or negative charges. Ions are separated based on their mass (m) to charge (z) ration (m/z) in the mass analyzer according to a variety of physical principles, and then detected. After the ions make contact with the detector or produce an image current, useable signals are generated and recorded by a computer system. The computer displays the signals graphically as a mass spectrum showing the relative abundance of the signals according to their m/z ratio. These operations can be accomplished on any type of mass spectrometer, including but not limited to ion trap, orbitrap, triple-quadruple, time-of-flight, hybrid quadrupole-time-of-flight, Fourier transform ion cyclotron resonance (FT ICR), and ion mobility spectrometer mass spectrometers.

As used herein, the term "mass spectrometer" in reference to an instrument refers to a laboratory instrument capable of providing mass spectrometric information, such as that described herein.

As used herein, the term "mass spectrum" refers to a graphical display of the relative abundance of ion signals against their respective m/z ratios. Typically the highest signal is taken as 100% abundance and the remaining signals are expressed as a percentage of 100%.

As used herein, the term "electrospray ionization" or "ESI" refers to the use of an electric field to achieve the transfer of ions from solution into the gaseous phase before they are subjected to mass spectrometric analysis. Ionic species in solution can thus be analyzed by ESI-MS with increased sensitivity. Neutral compounds can also be converted to ionic form in solution or in gaseous phase by protonation, cationization (e.g. metal cationization), or deprotonation for negative ion mode analysis, and hence can be studied by ESI-MS.

As used herein, the term "electrospray ionization mass spectrometry" or "ESI-MS" or "direct infusion electrospray ionization mass spectrometry" refers to a transfer of ionic species from solution into the gas phase by ESI involving at least three steps: (1) dispersal of a fine spray of charge droplets, followed by (2) solvent evaporation and (3) ion ejection from the highly charged droplets into a tube, which is maintained at a high voltage (e.g. 2.5-6.0 kV) relative to the wall of the surrounding chamber. Thus a mist of highly charged droplets with the same polarity as the capillary voltage is generated. The application of a nebulizing gas (e.g. nitrogen), which shears around the eluted sample solution, enables a higher sample flow rate. The charged droplets, generated at the exit of the electrospray tip, pass down a pressure gradient and potential gradient toward the analyzer region of the mass spectrometer. With the aid of an elevated ESI-source temperature and/or another stream of nitrogen drying gas, the charged droplets are continuously reduced in size by evaporation of the solvent, leading to an increase of surface charge density and a decrease of the droplet radius. Finally, the electric field strength within the charged droplet reaches a critical point at which it is kinetically and energetically possible for ions at the surface of the droplets to be ejected into the gaseous phase. The emitted ions are sampled by a sampling skimmer cone and are then accelerated into the mass analyzer for subsequent analysis of molecular mass and measurement of ion intensity. Electrospray ionization mass spectrometry is considered a "desorption ionization" method.

As used herein, the term "direct infusion" refers to the practice of introducing sample solution into the ESI ion source without utilizing a chromatographic (LC) or electrophoretic (CE) system. In this case, liquid samples are introduced into an electrospray emitter through the use of a syringe pump that maintains the flow of solution toward the tip, where the electrospray process takes place. Alternatively, samples are loaded directly into the emitter and the solution flow is maintained by capillary action through consumption of sample at the tip, with no use of additional back pressure. Alternatively, sample introduction can be accomplished also by coupling ESI-MS with liquid chromatography (LC-MS) or capillary electrophoresis (CE-MS), which facilitate the analysis of very complex mixtures.

As used herein, the term "front end techniques" or "coupling techniques" refers to a combination of analytical instruments, such as High Performance Liquid Chromatography/Mass Spectrometry (LC-MS); Capillary Electrophoresis/Mass Spectrometry (CE-MS); etc.

As used herein, the term "liquid chromatography electrospray ionization tandem mass spectrometry" or "LC-ESI MS/MS" refers to a combination of the separation capabilities of liquid chromatography with the desorption ability of electrospray ionization, mass analysis capability, and specificity of tandem mass spectroscopy.

As used herein, the term "mass analyzer' refers to any type of MS component capable of differentiating the various analytes according to their m/z ratio. This term includes but not limited to ion trap, orbitrap, triple-quadruple, time-of-flight, hybrid quadrupole-time-of-flight, Fourier transform ion cyclotron resonance, and ion mobility spectrometer mass spectrometers. In mass analyzers, a specific physical quantity is progressively varied to destabilize ion trajectories in such a way as to make them reach the detector at a different point during the scan, so that they can be appropriately differentiated.

As used herein, the term "MS/MS" or "MS" or "tandem mass spectrometry" or "$MS^2$" in reference to MS refers to an experiment in which an analyte ion of interest is mass selected in a certain region of the instrument, whereas the remaining ions are ejected or otherwise eliminated. The selected ion is subsequently activated by different types of processes, including but not limited to collision induced dissociation (CID), higher-energy collisionally induced dissociation (HCD), electron transfer dissociation (ETD), electron capture dissociation (ECD), infrared multiphoton dissociation (IRMPD), and many others. As a results of activation by any of these processes, the ion of interest undergoes dissociation into fragments that are intimately related to the initial molecular structure. The fragment ions can be monitored by the mass analyzer to obtain structural information on the initial molecular ion and to complete its structural characterization. In a typical example pertinent to triple-quadrupole instruments, the Q1 element of the instrument can be set to select one specific m/z ratio by filtering out any other molecular ions with different m/z ratios. This separation step takes places directly inside the MS instrument, thus eliminating complicated and time-consuming sample purification procedures prior to MS analysis. The selected precursor ion can be then activated in the Q2 element of the triple quad instrument by collision with an inert gas that is purposely introduced to accomplish CID. After that, the ensuing product ions can be detected in the Q3 element of the triple quad instrument. Alternatively, when an ion trap instrument is utilized, the steps of ion selection, dissociation activation, and fragment detection are achieved in the same element of the mass spectrometer at subsequent times of the experiments. In this way, a given product ion generated by the first cycle of selection/activation/detection can be kept inside the trap and utilized as precursor ion for an additional cycle, and so on. In this way, subsequent rounds of CID reactions can be sequentially performed in what is denoted as $MS^n$ (in which n is the number of CID reactions). This process can help differentiate molecules with similar structures. However, ion trap analyzers cannot provide precursor scan and neutral loss modes of data acquisition. For quantification, ion trap analyzers are typically ~10 times less sensitive when compared with triple quad systems operated in multiple reactions monitoring (MRM) mode. Alternatively, multiple fragmentation techniques can be employed to obtain the same type of information.

As used herein, the terms "consecutive reaction monitoring" or "CRM", and "multiple reactions monitoring" or "MRM" refer to the application of sequential selection/activation/detection cycles in which the product ion from the first stage of dissociation becomes the precursor ion for the second stage, and so on. The difference between CRM/MRM and $MS^n$ is that the latter enables the acquisition of full fragmentation spectra, whereas the former enable the targeted detection of the desired fragments from a specific precursor ion.

As used herein, the terms "ESI-tandem-MS", "ESI-MS/MS", and "ESI-MS$^n$" refer to tandem MS of ions produced by electrospray ionization.

As used herein, the terms "ion mobility spectrometry mass spectrometry", "ion-mobility separation-mass spectrometry" and "IMS-MS" refer to techniques in which analytes are not differentiated according to their m/z ratios, but rather to the overall size/shape possessed by their molecular structure. Ions are injected in a region of the mass spectrometer, which is flooded with a low pressure of inert gas. As the ions are driven through this region by a modest electric field, they encounter molecules of inert gas with a probability that is a function of their size/shape. Larger/extended ions have a greater encounter probability than smaller/compact ones and, thus, will experience greater delay in traversing this region of the mass spectrometer. Therefore, the time of arrival to the detector is a unique characteristic of a given size/shape and can be used to uniquely identify the corresponding ion.

As used herein, the term "medical condition" or "medical state" or "medical stage" refers to a variety of disease stages, including cancer, such as prostate cancer, breast cancer, etc.; specific stages of cancer; bacterial infections; viral infections; genetic and metabolic disorders; and includes healthy cells and tissues.

As used herein, the term "subject diagnosed with a cancer" refers to a subject who has been tested and found to have cancerous cells. The cancer can be diagnosed by using any suitable method, including but not limited to, biopsy, x-ray, blood test, and the diagnostic methods of the present invention.

As used herein, the term "sample" includes, but is not limited to a total nucleic acid sample, i.e. a mixture of nucleic acids isolated from a cell, a tissue, a fluid, and from a single cell organism. In the simplest embodiment, such a nucleic acid sample is the total RNA isolated from a biological sample. The nucleic acid (either DNA or RNA) may be isolated from the sample according to any of a number of methods well known to those of skill in the art and as described herein.

As used herein, the terms "biopsy tissue" or "patient sample" or "tumor sample" or "cancer sample" refer to a sample of cells or tissue that is removed from a subject for the purpose of determining if the sample contains cancerous tissue. In one embodiment, a biopsy tissue or a sample of cells is obtained when a subject is suspected of having cancer. The biopsy tissue or fluid is then examined for the presence or absence of cancer, stage of cancer or is "healthy", i.e. no indication of cancer.

As used herein, the term "biological sample" refers to a sample obtained from an organism or from components (e.g., cells, cellular compartments, organelles, etc.) of an organism. The sample may be of any biological tissue or fluid. Frequently the sample will be a "clinical sample" that is a sample derived from a patient. Such samples include, but are not limited to, blood, blood cells (e.g., white cells), cultured cells, tissue or fine needle biopsy samples, pleural or any other type of fluid, or cells therefrom, bacteria, etc. Biological samples may also include sections of tissues such as frozen sections taken for histological purposes.

BRIEF DESCRIPTION OF THE DRAWINGS

FIG. 3A-3B. Shows exemplary $MS^n$ data for *S. cerevisiae* RNA structural modification analysis: a) Anionic $MS^2$ spectrum of methyl-G from *S. cerevisiae* total RNA digest, which was obtained by activating the m/z 376 species observed in FIG. 1; b) Cationic $MS^3$ spectrum obtained by activating m/z 378→166→. The inset displays the $MS^4$ spectrum obtained by activating m/z 378→166→124→. Solid arrows indicate possible methylated positions; dashed arrows suggest putative cleavages.

FIG. 4A-4E. Shows exemplary IMS-MS data for *S. cerevisiae* RNA structural analysis: 4a) IMS-MS profile of m/z 378 obtained after isolation in the mass-selective quadrupole and separation in the ion mobility element. The dotted line represents the actual profile, while solid lines are individual components provided by Gaussian fitting (see Examples for details). Panels 4b-4d are reconstructed ion chromatograms (RICs) of unique fragments from individual methyl-G isomers: 4b) RIC of m/z 151 unique for Gm; 4c) m/z 110 for $m^7G$; 4d) m/z 68 for $m^2G$; and 4e) m/z 54 for $m^1G$.

FIG. 5A-5B. Shows exemplary IMS-MS data for *S. cerevisiae* RNA structural analysis: 5a) Anionic IMS-MS heat-map obtained from *S. cerevisiae* grown in synthetic complete (SC) medium. 5b) Differential plot obtained by subtracting the plot in panel 5a) from the one provided by *S. cerevisiae* grown YPD medium (FIG. 2).

FIG. 6A-6B. Shows exemplary IMS-MS data for *E. coli* RNA structural analysis: 6a) Anionic IMS-MS heat map obtained from *E. coli* grown in SC medium. 6b) Difference plot obtained by subtracting the plot in panel 6a) from the one provided by *S. cerevisiae* grown in the same medium (FIG. 4a).

FIG. 9A-9B: Shows exemplary methods of determinations based on automated ion mobility analysis and time aligned parallel (TAP) fragmentation. 9A. Data interpretation using exemplary Waters Driftscope software. Exemplary Scheme 1 is one embodiment of an experimental workflow (see Examples for details). 9B. Shows an exemplary schematic of ESI and the instrument used. Further it shows two representative global profiles views followed by database searching and then confirmation of putative hits by either fragmentation or IMS-MS.

FIG. 10A-10B: Shows an exemplary MS$^n$ analysis of methyl-G from *E. coli* total RNA digest. 10A) MS/MS spectrum of methyl-G from *E. coli* total RNA digest. 10B) MS$^3$ spectrum obtained by activating m/z 376.09→166.09→. Inset: MS$^4$ spectrum obtained by activating m/z 376.09→166.09→123.84.

FIG. 14A-14D: Shows exemplary results comparing benign vs. malignant tissues. 14A. Shows an exemplary difference plot revealing vast variation between benign and malignant tissues. 14B. Shows a hypothetical Principal Component (Cluster) Analysis from 6 patients showing different clustering of benign and malignant prostate tissues. Green indicates benign and red indicates presumed malignancy; 1=benign nodule, 2=Stage I or II, 3=Stage III or IV.

FIG. 21A-21C. Shows an exemplary analysis of viral RNA modifications. 21A. *E. coli* strain expressing HIV-1 5'-UTR. Different modifications are present in *E. coli* total RNA with and without 5'-UTR plasmid. The expressed 5'-UTR purified from the transformed strain contained a unique modification that was absent in wild type. 21B. Poliovirus in infected HeLa cells. 21C. L-A virus-like particles (VLP's) in infected w303 yeast cells. Total RNA extracted from uninfected hosts and infected cells showed distinct modifications patterns. Captured material contained unique modifications that differed from those detected in the corresponding total lysates. Affinity capture increased the ability to observe low-abundance modifications in viral RNA.

FIG. 29. Shows exemplary results of targeted profiling of structural modifications targeted in total RNA and mRNA. PTMs that are present in both total RNA and isolated mRNA. Red represents PTMs that are present in total RNA not mRNA. White represents an absence of a PTM.

FIG. 30A-30B: Shows exemplary elution results (30a) Elution from the magnetic beads coupled by biotin-streptavidin interactions. (30b) Elution from the magnetic beads coupled by direct formation of disulfide bonds.

FIG. 31: Shows an exemplary reaction mechanism for labeling an oligonucleotide with a fluorescent molecule.

DESCRIPTION OF THE INVENTION

Figure 1:
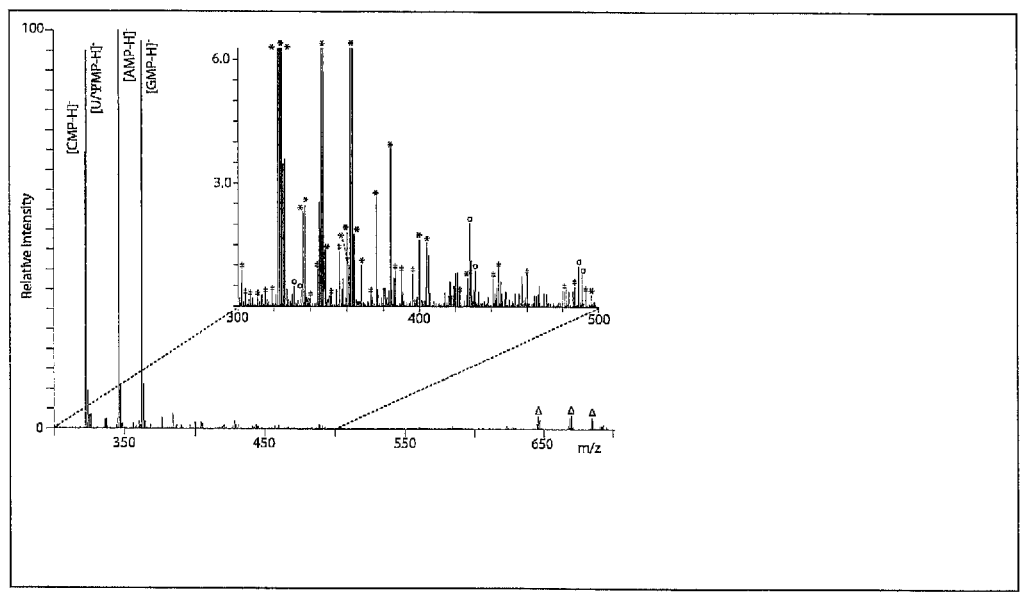
FIG. 1. Shows an exemplary representative ESI-MS spectrum of total RNA digest obtained from *S. cerevisiae* grown in YPD medium. The enlargement shows the region containing the majority of the PTMs. Signals marked with * are hits from our custom modifications registry; Δ proton-bound dimers of the most abundant species in the spectrum ǂ METLIN hits; o species detected also in the blank.

The present invention relates to high-throughput methods comprising direct infusion electrospray ionization mass spectrometry (ESI-MS), multistep tandem mass spectrometry ($MS^n$), consecutive reaction monitoring (CRM), ion mobility spectrometry mass spectrometry (IMS-MS), high-resolution MS, and IMS-MS, for genome-wide (whole cell or tissue) profiling of DNA and RNA nucleotides/nucleosides having a wide variety of variant structural modifications. In particular, these methods are contemplated for providing a specific profile of variant DNA and/or RNA chemically modified nucleic acids (i.e. structures) associated with specific medical conditions. Medical conditions may include, but are not limited to: cancer; including prostate, lung, uterus, larynx, ovary, breast, kidney, and many other types of cancers; specific stages of cancer; bacterial infections; viral infections; genetic and metabolic disorders; and any condition involving changes in DNA and/or RNA structural modifications.

The technology involves extraction of the total nucleic acids content from target cells/tissues, bodily fluids, or any other pertinent source of biological material; separation of DNA from RNA; digestion of either fraction into mono-nucleotide/nucleoside components; analysis; identification of modified variant components and quantification of their expression levels. The diagnosis is determined by comparing the global modification profiles (i.e., the patterns represented by the combination of both identity and relative abundance of the observed species), to that obtained from healthy or diseased cells/tissues. The diagnosis is not based on one individual species that may be linked to the condition of interest. It relies instead on the detection of multiple modifications (including patterns) and/or the mutual variations of their expression levels.

The application of this technology is contemplated to involve two or more separate steps. The initial setup phase will involve the utilization of mass spectrometry and ion mobility spectrometry analysis, followed by database-aided interpretation, to identify the panel of variants of canonical mono-nucleotide/nucleoside components that are linked to the condition of interest. Once the panel is established, the deployment phase will utilize standard immunoassay techniques (e.g., simple strips or microarray, platforms based on ELISA and similar methods) to perform detection in the field, such as in diagnostic labs, hospitals, pharmacies, physician practices, etc.

I. Advantages of the Technology (Relative to Existing Technology) are Described Below.

A) Other technologies are not capable of providing comprehensive profiles of variant DNA and/or RNA components, in contrast to the profiles shown herein. Thus established approaches for the analysis/detection of nucleic acids are blind to the vast majority of chemical modifications of RNA that are present in a cell or tissue. Unlike the methods of the present inventions, combined mass spectrometry and immunoassays have not been used to identify/quantify nucleic acid variants at whole-cell levels, or at the level of cell sub-compartments and organelles.

B) The technology developed and described herein, enables one to link panels of chemical DNA and/or RNA modifications to specific cellular malfunctions, without the need to identify them as either a cause or effect of the cell state of interest.

C) The methods of the present inventions offer greater diagnostic accuracy by linking mutual fluctuations of expression levels to the state of interest, rather than just the appearance/disappearance of individual markers.

D) To the best of the knowledge of the inventors, alternative approaches based on mass spectrometry and immunoassays have not been employed to observe panels of both DNA and RNA modifications simultaneously, for the purpose of correlating their profiles (identity and mutual relative abundances) to specific cell states.

E) The methods of the present inventions involve a small amount of sample consumption. A small fraction of biopsy, or surgically removed tissue, may be submitted to the technology, while preserving the bulk of the sample for pathology examination and any other type of analysis.

F) The methods of the present inventions may potentially be included in non-invasive procedures through the use of blood, urine, saliva, tears, amniotic fluid, tissue biopsies, and any possible biological sample containing nucleic acids.

G) Sample preparation allows for the utilization of a relatively small portion of the entire cellular content. The remaining components are still available for additional analysis (e.g., protein content for phenotypic expression analysis; DNA for genomic expression; RNA for transcriptomics analysis, etc.).

H) Could be readily adapted for unattended, automated operation by utilizing existing robotic systems, thus providing an excellent platform for high-throughput screening applications.

I) The immunoassay-based detection scheme will provide the basis for very inexpensive, convenient, easy to use, point of care diagnostic applications.

J) As a diagnostic tool, it could be employed to simultaneously recognize different possible risk factors, or identify the stage (benign, benign nodule, early vs. late stage) of a certain cancer; to identify the etiologic agent of an infection; to monitor the course and assess the effectiveness of therapeutic treatment. For example, when a stage of cancer is detected, treatment options which may be initiated include but are not limited to: active surveillance/watchful waiting, surgery, cryosurgery, ultrasound treatment, radiotherapy, hormone treatment, chemotherapy, etc. or combination thereof.

As another example, when methods described herein distinguish between a viral, such as a poliovirus, HIV-1, etc., a yeast (fungi) and bacteria cell infection in a cell, such as from a patient, then an appropriate antiviral treatment (i.e. a broad-spectrum inhibitor for picornavirus, antiretroviral therapies, respectively), antifungal treatment (such as amphotericin B (and its lipid formulations), various azole derivatives, echinocandins, and flucytosine) or antibacterial treatment (i.e. an antibiotic, such as amoxicillin, fluoroquinolones or cephalosporins, etc.), respectively, may be initiated to that patient.

K) Methods described herein can be used for identifying epigenetic changes in gene expression in organisms under different growth conditions.

II. Introduction.

The elucidation of the biological significance of whole cell or tissue DNA structural modifications and RNA post-transcriptional modifications is hampered by the dearth of effective high-throughput sequencing approaches for detecting, locating, and tracking their levels as a function of predetermined experimental factors. While RNA is primarily described herein, these methods are applicable to identifying and associating DNA structural modifications with cell physiological stages, cancer and disease states.

Therefore, with the goal of confronting this knowledge gap, a strategy was discovered and developed for completing global surveys of total deoxynucleotide modifications and total ribonucleotide modifications in a cell, which is based on the analysis of whole cell or tissue extracts by direct infusion electrospray ionization mass spectrometry (ESI-MS). Thus, in one embodiment, a direct infusion electrospray ionization mass spectrometer (ESI-MS) is used to identify and quantify at least one or more modification in a DNA structure. In another embodiment, a direct infusion electrospray ionization mass spectrometer (ESI-MS) is used to identify and quantify at least one or more modification in a RNA structure.

The methods described herein, eschews chromatographic separation to promote instead the direct application of MS techniques capable of providing detection, differentiation, and quantification of post-transcriptional modifications (PTMs) in complex ribonucleotide mixtures. Accurate mass analysis was used to carry out database-aided identification of PTMs, whereas multistep tandem mass spectrometry (MS$^n$) and consecutive reaction monitoring (CRM) provided the necessary structural corroboration. Thus, in one embodiment, multistep tandem mass spectrometry (MS$^n$) and consecutive reaction monitoring (CRM) are used to identify and quantify at least one or more modification in a DNA structure. In another embodiment, multistep tandem mass spectrometry (MS$^n$) and consecutive reaction monitoring (CRM) are used to identify and quantify at least one or more modification in a RNA structure.

Heat-map plots derived from these data obtained by ion mobility spectrometry mass spectrometry (IMS-MS) provided comprehensive modification profiles that are unique for certain cell types and metabolic states. Thus isolated tRNA samples were used as controlled sources of PTMs in standard-additions quantification. Intrinsic internal standards enabled direct comparisons of heat-maps obtained under different experimental conditions, thus offering the opportunity to simultaneously evaluate the global effects of such conditions on the expression levels of total cellular or tissue PTMs. This type of comparative analysis is contemplated to support the investigation of the system biology of RNA modifications. Thus, in one embodiment, an ion mobility spectrometry mass spectrometry (IMS-MS) is used to identify and quantify at least one or more modification in a DNA structure. In another embodiment, an ion mobility spectrometry mass spectrometry (IMS-MS) is used to identify and quantify at least one or more modification in a RNA structure.

A. Value of Total RNA Variant Analysis from Biological Samples.

One tenet of systems biology is that the behavior of a biological system arises from the complex network of functional interactions between its components. RNA is uniquely positioned in such a network to accurately capture the overall behavior of biological systems, as well as the specific metabolic and epigenetic state of a cell. The RNA building blocks display numerous variations of the four canonical bases, which contribute to defining the breathtaking diversity of structures and functions characteristic of natural RNA (Chang and Varani, 1997; Carell et al., 2012). These post-transcriptional modifications (PTMs) are introduced by the activity of specialized enzymes that, in many cases, have been identified and investigated (Ferré-D'Amaré, 2003). Over one hundred ribonucleotide PTMs and corresponding metabolic pathways are currently described in the RNA Modifications (Limbach et al., 1994; Cantara et al., 2011) and MODOMICS (Dunin-Horkawicz et al., 2006; Machnicka et al., 2012) databases. However, with the exception of a handful of PTMs involved in molecular recognition and stabilization of RNA structure (Kowalak et al., 1994; Ofengand, 2002; Helm, 2006) their biological function is still largely unknown. The observation that methylation of the 3' nucleotide protects miRNAs from uridylation, a prelude to exonucleolytic degradation (Li et al., 2005), suggests that many PTMs may act as signals or modulators of vital cellular processes. This type of observation has been made possible by the availability of targeted analytical approaches based on bisulfite chemistry (Frommer et al., 1992; Herman et al., 1996) or specific restriction enzymes (Singer-Sam et al., 1990; Issa et al., 1994), which enable the detection of methylation sites by high-throughput sequencing techniques (Ajay et al., 2011; Koboldt et al., 2013). Unfortunately, there are no high-throughput approaches for the majority of other PTMs. For this reason, their functional elucidation has been severely hampered by the inability to detect, locate, and track their levels as a function of predetermined experimental factors.

Mass spectrometry (MS)-based approaches have historically played a determinant role in the discovery and characterization of RNA modifications (McCloskey, 1979; McCloskey, J. A., 1985; Crain, 1990a; Nordhoff et al., 1996). This platform affords the ability to recognize the characteristic mass signatures associated with the different variants, as well as the unique fragmentation patterns necessary to confirm their structures (Banoub, J. H. and Limbach, P. A., 2010 and reference therein). High-resolution determinations enable the unambiguous differentiation of mononucleotides with very similar elemental compositions that produce nearly overlapping isotopic distributions (Quinn et al., 2013). Multistep tandem mass spectrometry ($MS^n$)(Solouki et al., 1996; Collings et al., 2001) and ion mobility spectrometry mass spectrometry (IMS-MS) (von Helden et al., 1995; Clemmer and Jarrold, 1997; Verbeck et al., 2002) have been proven capable of tackling mixtures of isobaric mononucleotides that share the same elemental composition, but display different structures (Quinn et al., 2013). These capabilities are exemplified by the analysis of the isomeric species uridine and pseudouridine, which include either an N- or C-glycosidic bond between the pyrimidine ring and ribose unit. This distinctive feature confers different stability to collisional activation, which is substantiated by a greater incidence of base loss from the N- than the C-glycosidic form (Wu and McLuckey, 2004). Unique conformations associated with the different ring attachments influence their interactions with background gas during IMS-MS analysis, thus enabling unambiguous differentiation even when both isomers are present simultaneously in the same sample (Quinn et al., 2013). Thus, in one embodiment, methods combine one or more types of mass spectrometric (MS) methods, including but not limited to high resolution, multistep tandem mass spectrometry ($MS^n$), ion mobility spectrometry mass spectrometry (IMS-MS), etc., used to identify and quantify at least one or more modification in a DNA structure. In another embodiment, embodiment, methods combine one or more types of mass spectrometry (MS) methods, including but not limited to high resolution, multistep tandem mass spectrometry ($MS^n$), ion mobility spectrometry mass spectrometry (IMS-MS), etc., are used to identify and quantify at least one or more modification in a RNA structure.

Modified ribonucleotides can be analyzed in complex mixtures obtained by hydrolyzing larger RNA samples into mononucleotide components, which may be further treated with phosphatase to obtain the corresponding nucleosides (Crain, 1990b). The ensuing samples are typically resolved by coupling liquid chromatography (Esmans et al., 1998; Chan et al., 2010; Su et al., 2014) or capillary electrophoresis (Apruzzese and Vouros, 1998) with MS detection (i.e., LC- and CE-MS, respectively), which are meant to provide separation and reduction of chemical background, while avoiding undesirable analyte bias. In previous work, we investigated the merits of direct infusion electrospray ionization (ESI) (Yamashita and Fenn, 1984; Banks et al., 1994) to perform nucleotide analysis in the absence of front-end chromatographic procedures (Quinn et al., 2013). The direct approach was evaluated by using standard samples that contained the canonical ribo- and deoxyribonucleotides with the addition of pseudouridine that constitutes the most abundant variant present in nature (Charette and Gray, 2000). Recently this method was extended to investigations of mixtures obtained directly from cell samples that contained the full complement of natural PTMs expressed by the selected organism. The capability of this approach was accessed to unambiguously recognize modified mononucleotides from the remaining background in the absence of chromatography, as well as the possibility of determining their abundance in complex biological samples. The reproducibility of this type of analysis was determined to learn whether this approach could provide comprehensive epitranscriptomic profiles and reveal possible correlations between RNA modifications and specific cellular states.

B. Applications.

Exposure of cells to external stimuli results in immediate adaptation through new regulatory responses affecting cellular memory to maximize survival. Often, these adverse external stimuli produce cellular anomalies that have been typically characterized by DNA methylations, histone modifications, and, more recently, activities involving various RNA species. Thus, DNA and RNA, and subsets thereof, are decorated with modifications. RNA in particular has post-transcriptional modifications that may have structural and functional roles within the cell. Thus, in one embodiment, a mass spectrometry platform is used to identify and quantify at least one or more modification in a DNA structure. In another embodiment, a mass spectrometry platform is used to identify and quantify at least one or more modification in a RNA structure.

1. Identifying Cancer Cells and Stages of Cancer.

A direct comparison between normal and malignant prostate samples described herein, revealed 13 common modifications and 1 and 6 unique RNA variants, respectively. In particular, heat maps of total RNA (including modified variants) distinguished between benign and cancerous prostate tissue. A heat map (or cluster analysis) relates to a graph of the number of each modified RNA structure identified using methods described herein. Analysis of benign and prostate tissue, FIG. 14A-14E, shows heat maps of modified RNA showing the different between these tissues. Identification of specific stages of cancer is contemplated using methods of the present inventions. Further the inventors describe obtaining breast, lung and uterus tissues from different individuals that showed tissue-specific features that were reproducible across donors. Thus, in one embodiment, methods comprising MS is used to identify and quantify at least one or more modification in a RNA structure associated with a cancer cell. For examples, see the Experimental section. In another embodiment, methods comprising MS is used to identify and quantify at least one or more modification in a DNA structure associated with a cancer cell.

Figure 15:
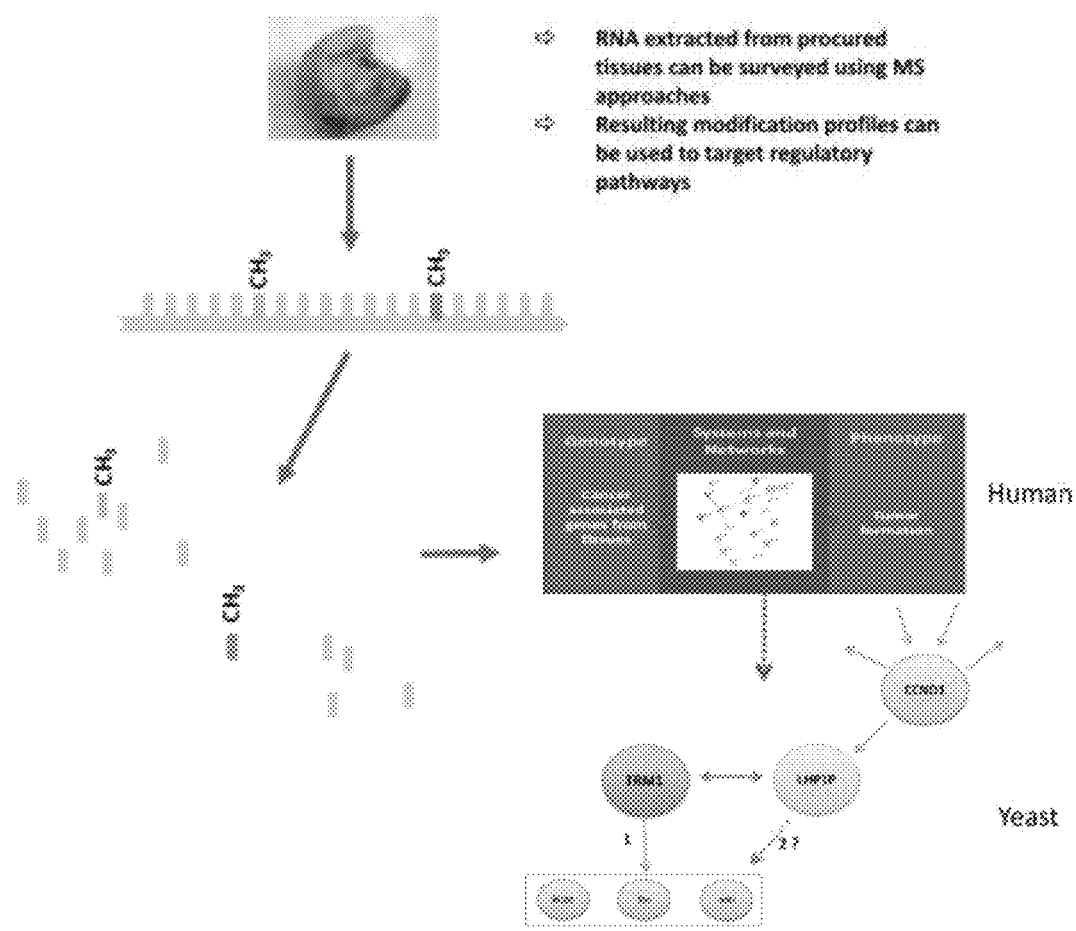
FIG. 15. Shows the hypothetical identification of a gene associated with certain prostate cancers known to cause downstream expression of RNA modifications common to those mapped, during the development of the inventions, in the malignant prostate tissue samples.

The systematic exploration of the interactome is typically supported by genomics and proteomics approaches that focus on nucleic acids and protein components. However, other cellular components traditionally viewed as products or intermediates of specific pathways can participate in regulatory mechanisms by influencing the interactome. For example, RNA is involved in protein synthesis and gene regulation, but its ability to undergo extensive post-transcriptional modification provides new opportunities for enzyme-based pathways to feedback at the mRNA-translation level to regulate protein expression. Therefore, an MS-based strategy was developed, as described herein, to obtain comprehensive maps of RNA modifications, which were then used to explore the complex signaling pathways responsible for the multistage processes that take cells from normalcy to malignancy. See, FIG. 15. Further, *S. cerevisiae* grown under various conditions including a mutant form of stress-activated protein kinase Hog1, contained unique PTMs absent in untreated cells and up or down regulated RNA modified structures, FIG. 26. Therefore, the use of RNA modifications as biomarkers for processes that take cells from normalcy to malignancy is contemplated for identifying precancerous cells.

Figure 16:
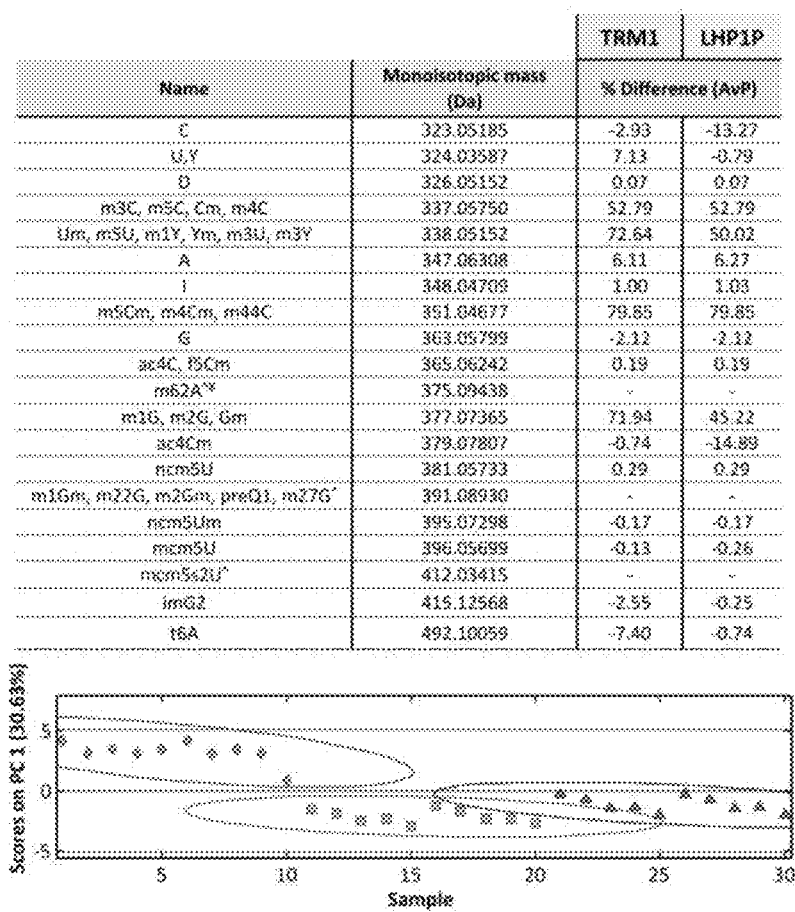
FIG. 16. Shows an exemplary knockdown analysis of genes expressed in prostate tissues. A. Comparison between control strain and TRM1 or PHP1P knockdowns revealed significant changes in modification expression (indicated by % difference and PCA (prostate cancer) analysis). ^Modifications that occur in TRM1. ¥ Modifications that occur in LHP1P. * Modifications found in the control but absent in the knock down samples.

An exemplary comparison between types of modified yeast cells, a control strain and TRM1 or PHP1P knockdowns revealed significant changes in RNA modification expression (indicated by % difference and PCA analysis)

showed ^modifications that occur in TRM1 knock down, ¥ modifications that occur in LHP1P knock down, * modifications found in the control, but not other samples, in FIG. 16. Thus, in one embodiment, methods comprising MS for identifying RNA having structural modifications is used to provide heat maps for identifying stages of cancer.

2. Identifying Virally Infected Cells.

As shown herein, methods of the present inventions were used to distinguish between poliovirus, LA virus and HIV-1, in addition to distinguishing between yeast (fungi) and bacteria cells. Therefore, the inventors contemplate using methods of the present inventions comprising MS for identifying microbes, i.e. virus and bacteria, and fungi. Thus, in one embodiment, the inventors contemplate methods comprising MS for identifying the type of infection using maps of isolated RNA having modified structures. In one embodiment, a mass spectrometry platform is used to identify and quantify at least one or more modification in a DNA structure associated with a virally infected cell. In another embodiment, a mass spectrometry platform is used to identify and quantify at least one or more modification in a RNA structure associated with a virally infected cell. For examples, see below and in the Examples.

Additionally, typical technologies employed for the analysis of viral RNA, such as RT-PCR, rely on hybridization/amplification and strand amplification techniques that fail to detect covalent modifications for the lack of ad hoc complementary nucleotides capable of sustaining strand extension. In other words, strand amplification techniques do not replicate the covalent modifications present on the original RNA strand due to the unavailability of a complementary base. In contrast, mass spectrometry is capable of identifying these covalent modifications when large sample amounts are present based on their characteristic mass to charge ratios and fragmentation properties. As a result of the sample size requirement, we have developed a magnetic bead based DNA probe hybridization technique to isolate sufficient amounts of viral RNA for MS analysis. Thus MS-based approaches require the availability of RNA samples that were not produced by strand-amplification techniques. For this reason, we further explored the application of affinity capture to obtain sufficient amounts of viral RNA directly from virions, infected cells, or culture media. The selected strategy involved the utilization of antisense oligonucleotides complementary to the specific target, which were anchored to paramagnetic beads for rapid separation. FIGS. 22A-22C and 23A-23C.

Figure 22A:
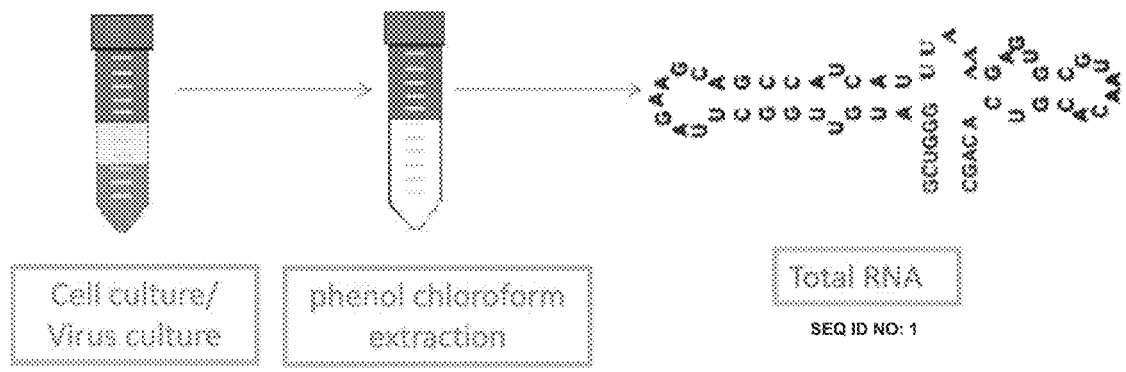
FIG. 22A-22C. Shows one exemplary embodiment of an experimental method strategy using a Widmer Probe 2 designed as a synthetic probe complementary to 5' UTR of LA virus. Magnetic beads with high-density thiol groups on the surface are coupled to an antisense probe (small olignucleotides). 22A. Total RNA isolation from cells. 22B. Magnetic Beads with high-density thiol groups on the surface. 22C. Analysis: including Gel Electrophoresis and Mass Spectrometry.
Figure 22B:

Therefore in order to begin determining whether MS analysis of ribonucleotide modifications at the whole genome level would provide information on targeting viral RNA, total RNA from S. cerevisiae was isolated using a classic phenol/chloroform extraction and digested to mononucleotides using a cocktail of specific nucleases. Global RNA modification profiles revealed 41 hits across technical and biological replicates with a reproducibility of ±4.4% and ±7.8% relative standard deviation (% RSD), respectively. Surprisingly, 13 RNA structures were found, which were known to be in other organisms, but not in yeast. Individual modification levels were absolutely and/or relatively quantified by either standard-additions method with known amounts of purified tRNA$^{Phe}$, or by using canonical nucleotides as intrinsic internal standards. See an exemplary overview of this method is shown in FIG. 22A.

Figure 22C:
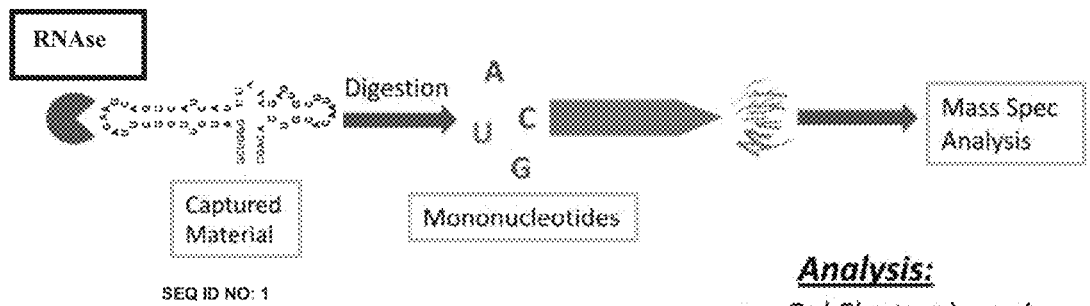
Figure 23A:
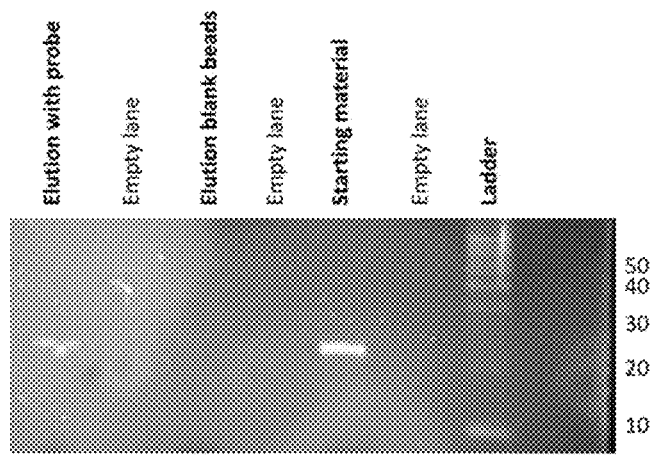
FIG. 23A-23C. Shows an exemplary analysis of RNA modifications identified using beads as described herein. Testing capture beads: Small antisense oligo 'Target' from Integrated DNA technologies (IDT). Capture Conditions: Flowthrough-Add total RNA to beads, heat to 95° C. and slow cool; Washes (5)—Using 150 mM Ammonium Acetate; Elution 1—Using 150 mM Ammonium Acetate; heat to 95° C.; remove SN immediately; and Elution 2—Using Water, heat to 95° C., remove SN immediately. 23A. 12% PAGE gel: Beads with probe vs. Blank Beads 23B. Comparison of target species. 23C. 0.8% denaturing agarose gel: Total RNA used in capture.
Figure 23B:
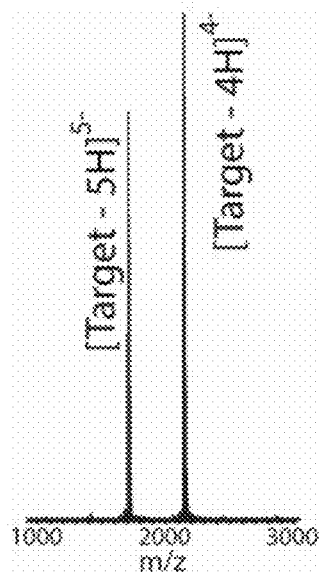
Figure 23C:
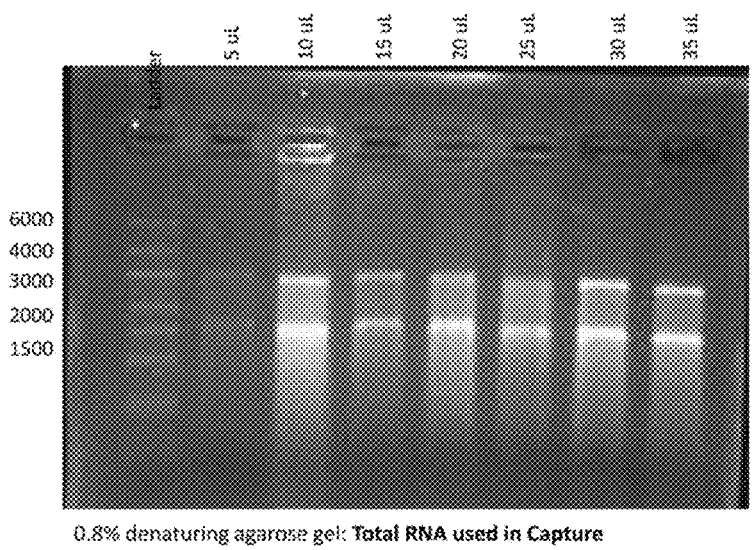
Figure 24:
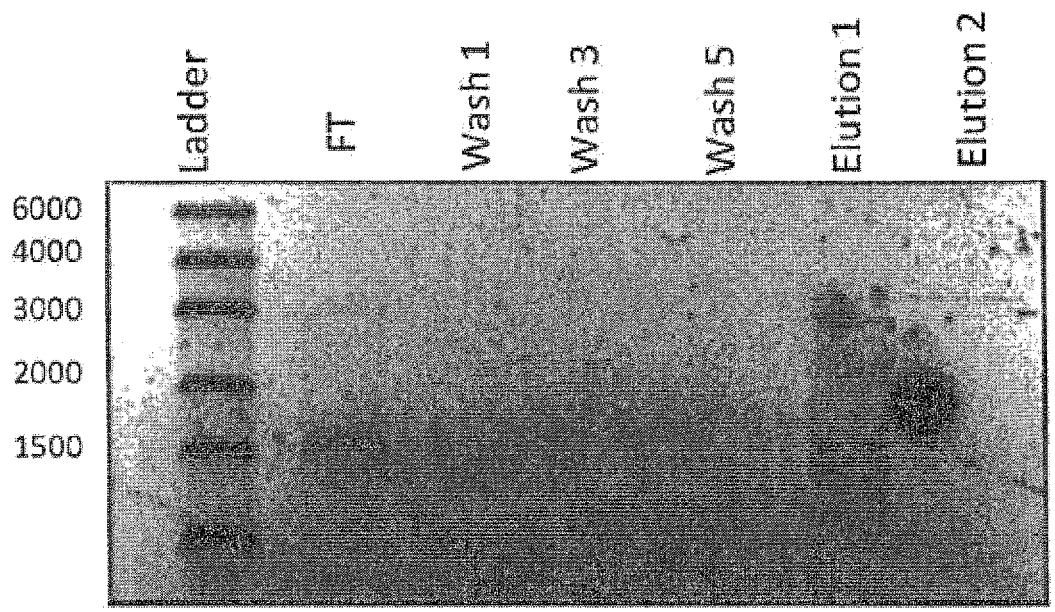
FIG. 24. Shows exemplary results showing the presence of RNA in Flowthrough and the first elution from RNA bead capture.
Figure 25:
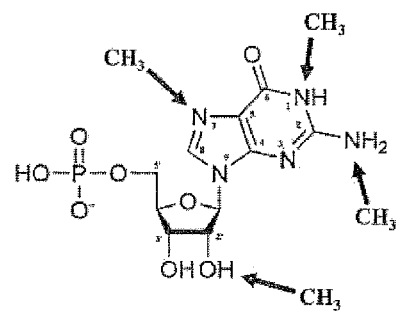
FIG. 25. Shows exemplary structural PTM RNA structure identified using the methods described herein.

Additionally (and concurrently with viral RNA studies described herein), studies were performed on HeLa cells to examine RNA modification content in total RNA versus isolated mRNA. Isolation of mRNA was performed using affinity capture techniques designed to target the poly A tail found common in mRNA species, see an exemplary overview of this method in FIG. 22B The success of the capture was confirmed using gel electrophoresis and reverse transcription polymerase chain reaction. FIG. 22C. The total RNA and isolated mRNA were then subjected to the same digestion and mapping as described herein. Global profiles revealed hits in total RNA and isolated mRNA. This information is contemplated for determining the applicability of this strategy to map modifications in rRNA and tRNA.

3. Identifying Infections.

In additional to viral infections, as shown herein, methods of the present inventions were used to distinguish between E. coli and S. cerevisiae, such that 26 modifications were common, whereas 14 and 17 were unique for each. Therefore, the inventors contemplate using methods of the present inventions comprising MS for identifying microbes and fungi. Thus, in one embodiment, the inventors contemplate methods comprising MS for identifying the type of infection using maps of isolated RNA having modified structures.

4. Identifying Changes in Cell Physiology.

Figure 26:
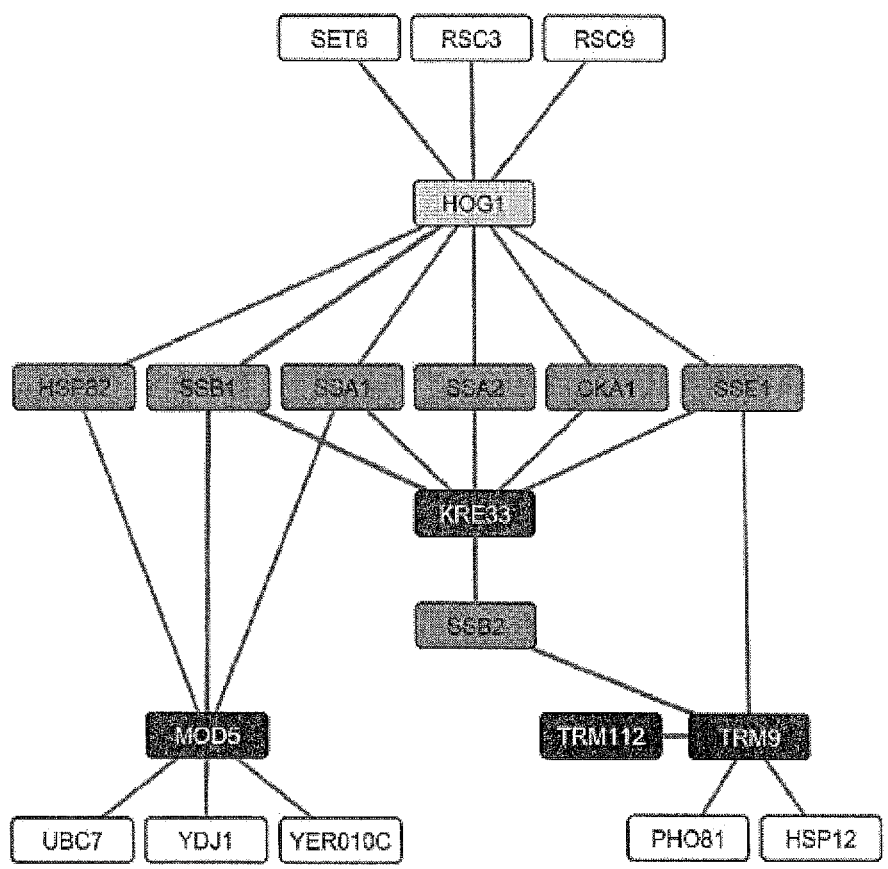
FIG. 26. Shows an exemplary interaction of HOG1 within a biochemical pathway.

As shown herein, methods of the present inventions were used to show changes in modified RNA structures associated with induction of proteins, such as the stress protein Hog1, FIG. 26. Therefore, the inventors contemplate using methods of the present inventions for identifying physiological states of cells. Thus, in one embodiment, the inventors contemplate methods comprising MS for identifying stressed cells using isolated RNA having modified structures.

In an exemplary embodiment, a mass spectrometry platform is used to monitor changes in RNA modifications potentially present in S. cerevisiae under various external stimuli.

C. Information Obtained During the Development of the Present Inventions.

With the rare exceptions of 2-O'-methylation, adenosine-N6-methylation, and pseudouridylation, current high-throughput sequencing approaches (e.g., RNA-seq and similar next-generation techniques) are incapable of detecting PTMs, owing to the fact that analysis takes place on DNA copies, rather than genuine RNA samples bearing the PTMs. The lack of sufficient data on PTM expression and distribution has significantly hampered the elucidation of their biological functions. MS-based approaches are contemplated to fill this gap in information by enabling PTM recognition and quantification on the basis of their unique mass and fragmentation signatures. These types of approaches have traditionally relied on liquid chromatography and capillary electrophoresis to reduce chemical background and provide separation before analysis. We recently demonstrated proof-of-principle for their possible implementation without any high-resolution separation, which will greatly simplify their incorporation in large scale, high-throughput applications. The method developed and described here was found capable of providing comprehensive surveys of ribonucleotide modifications at the full-transcriptome level. Direct infusion analysis with either high-resolution MS or IMS-MS detection enabled the positive identification of PTMs in complex cellular extracts based on their individual molecular masses, unique fragmentation patterns, and characteristic conformational features. Eliminating typical front-end chromatographic steps streamlined the operations without affecting detection sensitivity and characterization capabilities. Combining lysis and nucleic acid extraction in a single step led to minimal carryover of cellular components, which did not have any appreciable consequence on the ability to detect modified ribonucleotides. The proposed workflow provided comprehensive PTM information by using as little as ~800 µg of wet cell pellet or ~69 microL of culture at 0.3 $OD_{600}$ (corresponding to ~$1.2 \times 10^7$ cells). Contemplative estimates show that the same analysis could be comfortably completed by using as little as 25 micrograms of human tissue, well below the amount of material attainable from typical biopsy operations.

The proposed approaches rely on database searching and gas-phase activation techniques to positively identify the observed PTMs. However, these methods do not preclude the identification of new PTMs that are absent from the available databases, i.e. not previously reported. Indeed, it is likely that many of the observed signals that did not return hits in these experiments may correspond to yet undiscovered and/or unidentified PTMs. Identification of the presence of new PTM RNA structures in total cell extracts using methods of the present inventions provides an additional benefit over previous methods in light of the almost exclusive emphasis placed by earlier studies on tRNA/rRNA analysis (McCloskey, 1979; McCloskey, J. A., 1985; Crain, 1990a; Chan et al., 2010; Su et al., 2014). In summary, the information provided herein, clearly demonstrated that methods of the present inventions comprising various MS platforms, in concert or individually, are capable of providing the information necessary to support structural RNA characterization.

The utilization of isolated/commercial tRNA standard provided an excellent avenue for accomplishing quantification in the absence of pure stocks of ribonucleotide variants. Reinterpreting a classic standard-additions strategy, purified tRNA from commercial sources was added to total RNA extracts immediately before ribonuclease digestion, which enabled the release in situ of accurately known amounts of specific PTMs. In this way, proper signal-concentration curves were obtained in parallel for the PTMs in the standard, thus enabling their multiplexed determination in the total ribonucleotide mixture. Further, we evaluated also the possibility of utilizing the endogenous canonic ribonucleotides as a proxy internal reference.

This approach allowed us to determine the relative abundance of PTMs with no addition of individual standards. The fact that the results matched the quantitative data from standard-additions determinations provided validation and enabled us to use AvPs to accurately monitor changes of expression levels across multiple samples. The results demonstrated that the typical technical reproducibility (i.e., sample to sample of the same culture) was significantly better than the biological one (i.e., culture to culture), thus substantiating the robustness of the proposed workflow. The observed reproducibility levels (expressed as average RSD % for detected PTMs) were obtained without the utilization of stable-isotope standards, which is particularly challenging when multiple PTMs are targeted at the same time. As a natural development of any strategy based on MS platforms, future work will explore the possibility of incorporating different isotope labeling techniques in our approach. It is expected that their implementation will further improve the technical reproducibility, but it is not clear whether they will have any beneficial effect on the biological one. In the meantime, the reproducibility observed for our label-free approach allowed us to define the boundaries for deciding whether any fluctuation observed in yeast samples might be simply ascribable to experimental inconsistencies, or assumed legitimate biological significance.

The heat-maps afforded by IMS-MS analysis clearly substantiated the possibility of visualizing in a very direct and compact format the full complement of PTMs produced by a cell, i.e. a full profile, which will be expected to promote large-scale comparative studies of complete epitranscriptomes. Thus in one embodiment, a heat map showing types of RNA structural modifications associated with the presence of cancer cells is contemplated. Thus in a further embodiment, a heat map showing types of RNA structural modifications associated with the stage of cancer is contemplated. In particular, prostate cancer is diagnosed based upon a heat map showing types of RNA structural modifications associated with prostate cancer. Thus in a further embodiment, a heat map showing types of RNA structural modifications associated with the stage of cancer is contemplated.

The unique features identified by dispersing the signals on the $t_D$ and m/z dimensions can lead to an immediate appreciation of qualitative variations between the types of PTMs in different samples. The ability to complete direct data subtraction offers the opportunity to detect and quantify more subtle variations of expression levels manifested by common PTMs. The possibility to observe concomitant variations of modifications in comprehensive and self-consistent fashion will enable the investigation of their functional relationships at the system biology level. In particular, it is contemplated to use methods described herein to investigate up- or down-regulation of specific PTMs as a function of growth conditions.

References: The following references are herein incorporated by reference in their entirety.

Ajay, S. S., Parker, S. C. J., Ozel Abaan, H., Fuentes Fajardo, K. V., and Margulies, E. H. (2011). Accurate and comprehensive sequencing of personal genomes. Genome Res 21, 1498-1505.

Apruzzese, W. A., and Vouros, P. (1998). Analysis of DNA adducts by capillary methods coupled to mass spectrometry: a perspective. Journal of Chromatography 794, 97-108.

Banks, J. F., Shen, S., Whitehouse, C. M., and Fenn, J. B. (1994). Ultrasonically assisted electrospray ionization for LC/MS determination of nucleosides from a transfer RNA digest. Analytical Chemistry 66, 406-414.

Banoub, J. H., and Limbach, P. A. (2010). Mass Spectrometry of Nucleosides and Nucleic Acids (Boca Raton Fla.: CRC Press Inc.).

Biemann, K., and McCloskey, J. A. (1962). Application of mass spectrometry to structure problems. VI. Nucleosides. J. Am. Chem. Soc. 84, 2005-2007.

Bushberg, J. T., Seibert, J. A., Leidholdt Jr., E. M., and Boone, J. M. (2012). The essential physics of medical imaging (Philadelphia: Wolters Kluwer Health/Lippincott Williams & Wilkins).

Cantara, W. A., Crain, P. F., Rozenski, J., McCloskey, J. A., Harris, K. A., Zhang, X., Vendeix, F. A. P., Fabris, D., and Agris, P. F. (2011). The RNA Modification Database, RNAMDB: 2011 update. Nucleic Acids Res. 39, D195-201.

Carll, T., Brandmayr, C., Hienzsch, A., Müller, M., Pearson, D., Reiter, V., Thoma, I., Thumbs, P., and Wagner, M. (2012). Structure and function of noncanonical nucleobases. Angew. Chem. Int. Ed. Engl. 51, 7110-7131.

Castro-Perez, J., Roddy, T. P., Nibbering, N. M. M., Shah, V., McLaren, D. G., Previs, S., Attygalle, A. B., Herath, K., Chen, Z., Wang, S.-P., et al. (2011). Localization of fatty acyl and double bond positions in phosphatidylcholines using a dual stage CID fragmentation coupled with ion mobility mass spectrometry. J. Am. Soc. Mass Spectrom. 22, 1552-1567.

Chan, C. T. Y., Dyavaiah, M., DeMott, M. S., Taghizadeh, K., Dedon, P. C., and Begley, T. J. (2010). A quantitative systems approach reveals dynamic control of tRNA modifications during cellular stress. PLoS Genet. 6, e1001247.

Chang, K. Y., and Varani, G. (1997). Nucleic acids structure and recognition. Nat. Struct. Biol. 4 Suppl, 854-858.

Charette, M., and Gray, M. W. (2000). Pseudouridine in RNA: what, where, how, and why. IUBMB Life 49, 341-351.

Chomczynski, P., and Sacchi, N. (1987). Single-step method of RNA isolation by acid guanidinium thiocyanate-phenol-chloroform extraction. Anal. Biochem. 162, 156-159.

Clemmer, D. E., and Jarrold, M. F. (1997). Ion mobility measurements and their applications to cluster biomolecules. J. Mass Spectrom. 32, 577-592.

Collings, B. A., Campbell, J. M., Mao, D., and Douglas, D. J. (2001). A combined linear ion trap time-of-flight system with improved performance and MSn capabilities. Rapid Communications in Mass Spectrometry 15, 1777-1795.

Crain, P. F. (1990a). Mass spectrometric techniques in nucleic acid research. Mass Spectrom Rev 9, 505-554.

Crain, P. F. (1990b). Preparation and enzymatic hydrolysis of DNA and RNA for mass spectrometry. Methods Enzymol. 193, 782-790.

Crain, P. F. (1990c). Preparation and enzymatic hydrolysis of DNA and RNA for mass spectrometry. Meth. Enzymol. 193, 782-790.

Damen, C. W. N., Chen, W., Chakraborty, A. B., van Oosterhout, M., Mazzeo, J. R., Gebler, J. C., Schellens, J. H. M., Rosing, H., and Beijnen, J. H. (2009). Electrospray ionization quadrupole ion-mobility time-of-flight mass spectrometry as a tool to distinguish the lot-to-lot heterogeneity in N-glycosylation profile of the therapeutic monoclonal antibody trastuzumab. J. Am. Soc. Mass Spectrom. 20, 2021-2033.

Dunin-Horkawicz, S., Czerwoniec, A., Gajda, M. J., Feder, M., Grosjean, H., and Bujnicki, J. M. (2006). MODOMICS: a database of RNA modification pathways. Nucleic Acids Res. 34, D145-149.

Dwivedi, P., Wu, C., Matz, L. M., Clowers, B. H., Siems, W. F., and Hill, H. H., Jr (2006). Gas-phase chiral separations by ion mobility spectrometry. Anal. Chem. 78, 8200-8206.

Esmans, E., Broes, D., Hoes, I., Lemière, F., and Vanhoutte, K. (1998). Liquid chromatography-mass spectrometry in nucleoside, nucleotide and modified nucleotide characterization. Journal of Chromatography A 794, 109-127.

Fabris, D., Turner, K. B., and Hagan, N. A. (2010). Electrospray Ionization-Mass Spectrometry for the Investigation of Protein-Nucleic Acids Interactions. In Mass Spectrometry of Nucleosides and Nucleic Acids, (J. Banoub and P. Limbach eds., CRC Press, Taylor and Francis Group, LLC, London, U. K.), pp. 303-327.

Ferré-D'Amaré, A. R. (2003). RNA-modifying enzymes. Curr. Opin. Struct. Biol. 13, 49-55.

Fritsch, E. F., and Maniatis, T. (1989). Molecular Cloning: A Laboratory Manual (U.S.A: Cold Spring Harbor Laboratory Pr).

Frommer, M., McDonald, L. E., Millar, D. S., Collis, C. M., Watt, F., Grigg, G. W., Molloy, P. L., and Paul, C. L. (1992). A genomic sequencing protocol that yields a positive display of 5-methylcytosine residues in individual DNA strands. Proc. Natl. Acad. Sci. U.S.A. 89, 1827-1831.

Giles, K., Pringle, S. D., Worthington, K. R., Little, D., Wildgoose, J. L., and Bateman, R. H. (2004). Applications of a travelling wave-based radio-frequency-only stacked ring ion guide. Rapid Commun. Mass Spectrom. 18, 2401-2414.

Von Helden, G., Wyttenbach, T., and Bowers, M. T. (1995). Conformation of macromolecules in the gas phase: use of matrix-assisted laser desorption methods in ion chromatography. Science (New York, N. Y 267, 1483-1485.

Helm, M. (2006). Post-transcriptional nucleotide modification and alternative folding of RNA. Nucleic Acids Res. 34, 721-733.

Herman, J. G., Graff, J. R., Myohanen, S., Nelkin, B. D., and Baylin, S. B. (1996). Methylation-specific PCR: a novel PCR assay for methylation status of CpG islands. Proc. Natl. Acad. Sci. U.S.A. 93, 9821-9826.

Issa, J. P., Ottaviano, Y. L., Celano, P., Hamilton, S. R., Davidson, N. E., and Baylin, S. B. (1994). Methylation of the oestrogen receptor CpG island links ageing and neoplasia in human colon. Nat. Genet. 7, 536-540.

Koboldt, D. C., Steinberg, K. M., Larson, D. E., Wilson, R. K., and Mardis, E. R. (2013). The next-generation sequencing revolution and its impact on genomics. Cell 155, 27-38.

Kowalak, J. A., Dalluge, J. J., McCloskey, J. A., and Stetter, K. O. (1994). The role of posttranscriptional modification in stabilization of transfer RNA from hyperthermophiles. Biochemistry 33, 7869-7876.

Lapthorn, C., Pullen, F., and Chowdhry, B. Z. (2013). Ion mobility spectrometry-mass spectrometry (IMS-MS) of small molecules: Separating and assigning structures to ions. Mass Spectrom Rev 32, 43-71.

Li, J., Yang, Z., Yu, B., Liu, J., and Chen, X. (2005). Methylation protects miRNAs and siRNAs from a 3'-end uridylation activity in *Arabidopsis*. Curr. Biol. 15, 1501-1507.

Limbach, P. A., Crain, P. F., and McCloskey, J. A. (1994). Summary: the modified nucleosides of RNA. Nucleic Acids Res 22, 2183-2196.

Machnicka, M. A., Milanowska, K., Osman Oglou, O., Purta, E., Kurkowska, M., Olchowik, A., Januszewski, W., Kalinowski, S., Dunin-Horkawicz, S., Rother, K. M., et al. (2012). MODOMICS: a database of RNA modification pathways—2013 update. Nucleic Acids Research 41, D262-D267.

McCloskey, J. A. (1979). Characterization of nucleosides by mass spectrometry. Nucleic Acids Symp Ser s109-13.

McCloskey, J. A. (1985). Mass spectrometry of nucleic acid constituents and related compounds. In Mass Spectrometry in the Health and Life Sciences, A. L. Burlingame, N. Castagnoli, Eds., (Amsterdam: Elsevier), pp. 521-546.

Miller, J. H. (1972). Experiments in molecular genetics (Cold Spring Harbor Laboratory).

Monroe, M. (2012). Molecular Weight Calculator, v. 6.49. world wide web://ncrr.pnl.gov/software/.

Nordhoff, E., Kirpekar, F., and Roepstorff, P. (1996). Mass spectrometry of nucleic acids. Mass Spectrom. Rev. 15, 67-138.

Ofengand, J. (2002). Ribosomal RNA pseudouridines and pseudouridine synthases. FEBS Lett. 514, 17-25.

Quinn, R., Basanta-Sanchez, M., Rose, R. E., and Fabris, D. (2013). Direct infusion analysis of nucleotide mixtures of very similar or identical elemental composition. J. Mass Spectrom. 48, 703-712.

Singer-Sam, J., Grant, M., LeBon, J. M., Okuyama, K., Chapman, V., Monk, M., and Riggs, A. D. (1990). Use of a HpaII-polymerase chain reaction assay to study DNA methylation in the Pgk-1 CpG island of mouse embryos at the time of X-chromosome inactivation. Mol. Cell. Biol. 10, 4987-4989.

Smith, C. A., O'Maille, G., Want, E. J., Qin, C., Trauger, S. A., Brandon, T. R., Custodio, D. E., Abagyan, R., and Siuzdak, G. (2005). METLIN: a metabolite mass spectral database. Therapeutic Drug Monitoring 27, 747-751.

Solouki, T., Pasa-Tolic, L., Jackson, G. S., Guan, S., and Marshall, A. G. (1996). High-resolution multistage MS, MS2, and MS3 matrix-assisted laser desorption/ionization FT-ICR mass spectra of peptides from a single laser shot. Anal. Chem. 68, 3718-3725.

Su, D., Chan, C. T. Y., Gu, C., Lim, K. S., Chionh, Y. H., McBee, M. E., Russell, B. S., Babu, I. R., Begley, T. J., and Dedon, P. C. (2014). Quantitative analysis of ribonucleoside modifications in tRNA by HPLC-coupled mass spectrometry. Nat Protoc 9, 828-841.

Tomer, K. B., Guenat, C. R., and Deterding, L. J. (1988). Consecutive reaction monitoring in a four-sector mass spectrometer: MS4 and one step beyond. Anal. Chem. 60, 2232-2236.

Verbeck, G. F., Ruotolo, B. T., Sawyer, H. A., Gillig, K. J., and Russell, D. H. (2002). A fundamental introduction to ion mobility mass spectrometry applied to the analysis of biomolecules. J Biomol Tech 13, 56-61.

Wu, J., and McLuckey, S. A. (2004). Gas-phase fragmentation of oligonucleotide ions. International Journal of Mass Spectrometry 237, 197-241.

Yamashita, M., and Fenn, J. B. (1984). Electrospray ion source. Another variation on the free-jet theme. J. Phys. Chem. 88, 4671-4675.

World wide web://metlin.scripps.edu/index.php
World wide web://mods.rna.albany.edu/
World wide web://modomics.genesilico.pl/

1. Johansson, M. & Bystrom, A.: Dual function of the tRNA(m(5)U54)methyltransferase in tRNA maturation. RNA 8, 324-335 (2002).
2. Copela, L. A., Chakshusmathi, G., Sherrer, R. L., & Wolin, S. A.: The La protein functions redundantly with tRNA modification enzymes to ensure tRNA structural stability. RNA 12, 644-654 (2006).
3. Rylova, S. N., Amalfitano, A., et al.: The CLN3 Gene is a Novel Molecular Target for Cancer Drug Discovery. Cancer Research 62, 801-808 (2002).

EXPERIMENTAL

The following examples serve to illustrate certain embodiments and aspects of the present invention and are not to be construed as limiting the scope thereof.

In the experimental disclosures which follow, the following abbreviations apply: N (normal); M (molar); mM (millimolar); µM (micromolar); mol (moles); mmol (millimoles); (micromoles); nmol (nanomoles); pmol (picomoles); g (grams); mg (milligrams); µg (micrograms); ng (nanograms); pg (picograms); L and (liters); ml (milliliters); µl (microliters); cm (centimeters); mm (millimeters); µm (micrometers); nm (nanometers); U (units); min (minute); s and sec (second); deg (degree); ° C. (degrees Centigrade/Celsius).

Example I

The Following Describes Exemplary Methods and Materials Used During the Development of the Present Inventions.

A. Preparation of Cellular Extracts.

*Saccharomyces cerevisiae* strain BY4741 was grown in yeast extract, peptone, dextrose (YPD) and synthetic complete (SC) media. Cell suspensions were streaked onto YPD agar plates and incubated at 30° C. overnight. Five individual colonies were selected from each plate and placed into individual tubes containing 6 mL of either YPD or SC medium. Growth tubes were incubated at 30° C. with 200-rpm gyration. Optical density at 600 nm ($OD_{600}$) was monitored on a ThermoFisher Scientific (Waltham, Mass.) Nanodrop 2000c spectrophotometer until a value slightly greater than 0.3 units was achieved. Each liquid culture was diluted to a final 0.3 $OD_{600}$ to ensure that the tubes contained comparable "cell concentrations" (i.e., number of cell per volume unit). A 3-mL aliquot of each culture was centrifuged at 6000 g for 5 min to obtain pellets that contained approximately the same number of cells. In this respect, we determined that each 3-mL culture with 0.3 $OD_{600}$ provided a wet pellet weighing on average $34.9 \times 10^{-3}$ g. *Escherichia coli* K-12 strain MG1655 was grown in synthetic complete (SC) medium according to established procedures (Fritsch and Maniatis, 1989; Miller, 1972). Harvesting was carried out in analogous way.

Each pellet was disrupted by using Denaturation Solution (Life Technologies, Grand Island, N.Y.) in the presence of 0.5 mm diameter glass beads (BioSpec Products, Bartlesville, Okla.). When required by the standard-additions protocol, accurately known aliquots of *S. cerevisiae* $tRNA^{Phe}$ (Sigma-Aldrich, St. Louis, Mo.) were introduced at this point into the lysate to serve as internal standard. Total RNA was extracted by using the ToTALLY RNA Extraction Kit (Life Technologies, Grand Island, N.Y.), which is based on a typical phenol/chloroform procedure. The RNA was precipitated by using cold isopropanol and then treated with DNase 1 (New England Biolabs, Ipswich, Mass.) in 1× DNase buffer to remove any remaining DNA. The recovered RNA was subsequently desalted by ethanol precipitation overnight and reconstituted in 50 µL of RNase-free water (Sigma-Aldrich, St. Louis, Mo.). The concentration of intact total RNA from each sample was measured by UV absorbance at 260 nm. Nuclease P1 and phosphodiesterase 1 from snake venom (Sigma-Aldrich, St. Louis, Mo.) were employed to complete the digestion of RNA into individual mononucleotides, as previously described (Crain, 1990b). Immediately before analysis, final samples were diluted 1:10 in 150 mM ammonium acetate and 10% isopropanol.

B. Mass Spectrometry.

Samples were analyzed by direct infusion electrospray ionization (ESI) on either a ThermoFisher Scientific (Waltham, Mass.) LTQ-orbitrap Velos mass spectrometer or a Waters (Milford, Mass.) Synapt G2 HDMS IMS mass spectrometer. Analyses were performed in nanoflow ESI mode by using quartz emitters produced in house by a Sutter Instruments Co. (Novato, Calif.) P2000 laser pipette puller. Up to 5 µL samples were typically loaded into each emitter by using a gel-loader pipette tip. A stainless steel wire was inserted in the back-end of the emitter to supply an ionizing voltage that ranged between 0.9 and 1.2 kV. Source temperature and desolvation conditions were adjusted by closely monitoring the incidence of ammonium adducts and water clusters (Fabris, D. et al., 2010).

For high-resolution determinations, the LTQ-orbitrap instrument was calibrated by using an anion mixture that contained sodium dodecyl-sulfate, sodium taurocholate, and Ultramark. These standards enabled calibration over a range of 150-2000 m/z with up to 100 ppb mass accuracy. Tandem mass spectrometry (MS/MS) was accomplished by isolating the precursor ions of interest in the linear trap quadrupole (LTQ) element, which were then collided with N2 to activate fragmentation. Multistep activation experiments (MS$^n$) (Collings et al., 2001; Solouki et al., 1996) were completed by properly isolating first-generation and subsequent fragments prior to activation. The fragmentation of mass-selected ions was activated by using a typical 25V collision voltage. Ensuing products were mass analyzed either in the LTQ or the Orbitrap region of the instrument. Consecutive reaction monitoring (CRM)(Tomer et al., 1988) was performed by dialing the selected precursor→fragment transitions in the instrument data system. Series of diagnostic CRM experiments were performed in systematic fashion by inputting lists of precursor→fragment transitions specific for the different modifications, which were completed by the instrument with no further user intervention.

In IMS-MS experiments, apparent drift time (to) was determined by allowing ions to move through the travelling wave (Tri-WAVE) element of the instrument (Giles et al., 2004), before transferring them for mass analysis into the time-of-flight (TOF) stage operated in single reflectron mode. The instrument was calibrated by using a 2 mg/mL solution of cesium iodide in 50:50 water/methanol, which afforded up to 10 ppm mass accuracy. For comprehensive mixture analysis, the Tri-WAVE region was held at a pressure of approximately 4.40 mbar (uncalibrated gauge reading) by a 90 mL/min flow of $N_2$ and 180 mL/min of He. It was operated with an approximately 650 m/s IMS wave velocity, a 40 V wave height, a 109 m/s transfer wave velocity, and a 2.0 V transfer wave height. Time aligned parallel (TAP) dissociation and mass-selected time-aligned fragmentation of isobars were performed by raising the transfer voltage to 17 V and the cell pressure to ~4.60 mbar (uncalibrated gauge reading) with a flow of 140 mL/min N2 and 180 mL/min He. At the same time, IMS wave velocity was raised to ~700 m/s, transfer wave velocity to –600 m/s, and transfer wave height to 4.0 V.

C. Data Analysis.

High-resolution and fragmentation data obtained on the LTQ-orbitrap instrument were processed by Xcalibur 2.1 software (ThermoFisher Scientific, Waltham, Mass.). Mass calculations and predictions of elemental composition were performed by using the Molecular Weight Calculator software made available by the Pacific Northwest National Laboratory (Monroe, 2012). A data reduction step was implemented prior to database searching to simplify the operations and minimize the incidence of false positives. Instead of relying on a predefined intensity threshold to discriminate signal from noise, the experimental masses to be employed in the searches were selected according to a deconvolution algorithm included in the Xcalibur 2.1 software (Bushberg et al., 2012). This algorithm requires the detection of full-fledged $^{12}C$ and $^{13}C$ signals to correctly assign the charge state of observed species. If the $^{13}C$ peak of a low-abundance component was not recognized from the background (and a plausible charge was not assigned), then the mass of the corresponding $^{12}C$ was filtered out regardless of whether its intensity afforded an acceptable signal-to-noise ratio. The resulting mass list was then searched against the METLIN database (world wide web://metlin-.scripps.edu/index.php) and a non-redundant registry obtained by combining the entries present in the RNA Modifications (world wide web://mods.rna.albany.edu/) and MODOMICS databases (world wide web://modomics.gen-esilico.pl/). Matching between experimental data and database information was carried out by using software developed in house.

IMS-MS data were displayed in the form of heat-map plots with arrival time ($t_D$) and mass to charge ratio (m/z) placed on the x- and y-axis, respectively, by using OriginPro 9.1 (Origin Lab, North Hampton, Mass.). A color gradient provided in each plot was used to communicate the signal intensity expressed in arbitrary ion counts. For data subtraction analysis, appropriate scaling factors were utilized to align the intensity scales of the selected plots. Such factors were calculated to match the combined intensities of the four canonical ribonucleotides (i.e., $$\sum_1^4 cr_i,$$

with $cr_i$ corresponding to the respective absolute intensity in arbitrary counts) observed in each plot. Taking advantage of this proxy, de facto internal reference, it was possible also to express the abundance of each species in relation to that of the canonical ribonucleotides according to:

$$AvP_x = \frac{ai_x}{\sum_1^4 cr_i} \cdot 100 \qquad \text{Equation 1}$$

in which $AvP_x$ is the abundance versus proxy of a certain species obtained from its absolute intensity ($ai_x$) normalized to the combination of the abundances of the canonical ribonucleotides $$\left(\sum_1^4 cr_i\right).$$

Home-built software was employed to process the experimental data, calculate AvP values and, when necessary, apply appropriate scaling factor for data alignment. The same application was employed also to perform point-by-point subtraction of aligned data. The software application developed in house is the object of a manuscript in preparation. The results were visualized in heat-map format by utilizing OriginPro 9.1 (Origin Lab, North Hampton, Mass.).

Please refer to FIG. 9A-9B, Scheme 1 for one embodiment of an outline of the methods used during the development of the present inventions.

Example II

The Following Example Describes Direct Infusion Analysis of Cellular Nucleotide Mixtures.

A sensible but deceptively challenging way to reduce sample losses and analyte bias consists of reducing the number of sample-handling steps included in a prospective experimental workflow. Classic phenol-chloroform extraction was used to simultaneously achieve cell lysis and rapid isolation of nucleic acid components (Chomczynski and Sacchi, 1987), followed by digestion into separate mononucleotides (Crain, 1990b). Owing to the absence of high-resolution separation steps, the final samples were anticipated to contain the desired mononucleotide analytes and also unrelated cellular components carried through the entire workflow (Scheme 1, see FIG. 9A-9B, bottom). The complexity of these types of mixtures can be immediately appreciated by examining representative data obtained from a digest of total RNA from a sample of *S. cerevisiae* grown in yeast extract, peptone, dextrose (YPD) medium, which are shown in FIG. 1., A Representative ESI-MS spectrum of total RNA digest obtained from *S. cerevisiae* grown in YPD medium. The enlargement shows the region containing the majority of the PTMs. Signals marked with * are hits from our custom modifications registry; Δ proton-bound dimers of the most abundant species in the spectrum ┼ METLIN hits; o species detected also in the blank. A broad distribution of signals with very different intensities covered the entire range between m/z 300 and 700—the region in which PTMs are typically observed. Abundant signals were readily assigned to the deprotonated molecular ions of canonical ribonucleotides (i.e., [NMP-H]$^-$, where N indicates any nucleoside)(Quinn et al., 2013). Their experimental masses exhibited an average of ~100 ppb deviation from values calculated from the corresponding elemental compositions, which matched the typical accuracy afforded by these types of LTQ-orbitrap determinations (Quinn et al., 2013).

Figure 2:
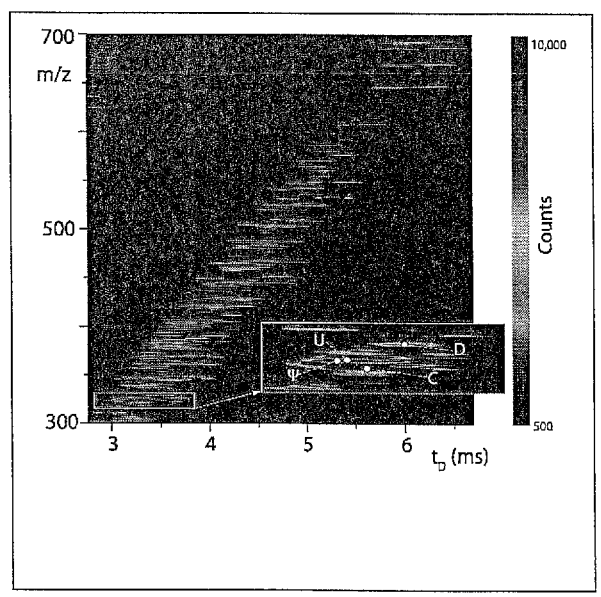
FIG. 2. Shows an exemplary heat-map obtained by IMS-MS analysis in negative ion mode of the *S. cerevisiae* RNA digest shown in FIG. 1 (see Examples for details).

The complexity of whole-cell extracts was also confronted by utilizing IMS-MS, which enables the differentiation of ions according to their size/conformation. In this technique, ions are dispersed on the time dimension as they travel across a low-pressure region of the instrument (Dwivedi et al., 2006; Lapthorn et al., 2013). The probability of undergoing low-energy collisions with background gas is a function of their conformation, which determines the travel time. The corresponding data are displayed in the form of heat-maps or 3D plots, in which the different dimensions consist of arrival time ($t_D$), mass to charge ratio (m/z), and signal intensity. A representative heat-map obtained from the same yeast extract is shown in FIG. 2. The canonical ribonucleotides were immediately recognized on the basis of their characteristic m/z and $t_D$ values, as exemplified in the enlarged region of the map. As demonstrated in previous work, the additional dimension facilitated the differentiation of isomeric/isobaric species, such as uridine and pseudouridine, which cannot be discriminated solely by mass analysis (Quinn et al., 2013). Given that the sample was derived directly from a whole-cell extract with no RNA fractionation, the corresponding heat-map provided an immediate and comprehensive representation of the PTMs present in the cells.

Example III

The Following Example Describes Identification of Modified Ribonucleotides.

The vast majority of the detected signals were readily assigned with the aid of database searching. Initial data reduction followed a conservative approach that eschewed the application of a pre-determined threshold to eliminate background noise on the basis of signal intensity, but relied instead on the detection of recognizable isotopic envelopes to differentiate signal from noise. This task employed a deconvolution algorithm included in the instrument's data system, which was designed to infer the charge state of any given signal from the respective isotopic distribution (Bushberg et al., 2012). When the ESI-MS data shown in FIG. 1 were processed, the filtering operation returned 1,206 of the 14,639 entries contained in the initial mass list, which were subsequently employed for database searching.

The searches were performed against a database specialized on RNA modifications, as well as a more comprehensive metabolomics registry capable of handling unrelated species present in the workflow carryover. The latter consisted of the METLIN database (hosted and maintained by the Scripps Institute) (Smith et al., 2005; world wide web:// metlin.scripps.edu/index.php), which comprises in excess of 75,000 endogenous and exogenous metabolites from a broad selection of living organisms, ranging from bacteria, to plants, to animals and humans. In addition, a non-redundant index of known RNA PTMs was generated in house by combining the information contained in the RNA Modifications Database (hosted by the RNA Institute of University at Albany) (Limbach et al., 1994; Cantara et al., 2011; world wide web://mods.rna.albany.edu/) and MODOMICS (hosted by the International Institute of Molecular and Cell Biology in Warsaw) (Dunin-Horkawicz et al., 2006; Machnicka et al., 2012; world wide web://modomics.genesilico.pl/). After redundant entries were eliminated, we ensured that the mass of each PTM appeared in both the nucleoside and nucleotide form to allow for the recognition of possible products present in the nuclease digests. For each entry, the mass of the deprotonated and protonated species (i.e., [M−H]$^-$ and [M+H]$^+$) were calculated to enable proper matching data obtained in either polarity. The final custom registry included 254 searchable entries.

A total of 268 database hits were obtained when the reduced experimental data were searched against METLIN, whereas 40 were found in the custom registry (Table 1). The observed experimental masses matched very closely those found in the databases. The majority of hits provided an average deviation between experimental and calculated masses that fell within the accuracy assessed from canonical ribonucleotides, whereas weaker signals displayed slightly higher deviations. The majority of such hits corresponded to modifications typically observed in *S. cerevisiae*'s ribosomal-RNA (rRNA) or transfer-RNA (tRNA), but 13 of them had not been previously reported for this organism according to the information included in the RNA Modifications and MODOMICS databases (marked with asterisk in Table 1). This observation may be a consequence of the broader scope of these analyses, which was not limited to specific rRNA/tRNA fractions but targeted whole-cell extracts. With merely a few exceptions, the majority of the hits afforded by the custom registry were also found in METLIN. This observation provides an indication of the excellent but not absolute overlap between the databases employed in the study. In particular, the greater breadth afforded by METLIN enabled the putative assignment of other notable but unrelated species of cellular origin (marked with a red tick in FIG. 1), such as UDP-L-arabinose, UDP-D-xylose, and many others. Their detection in the sample mixture—an unintended outcome of the broad nature of phenol-chloroform extraction—confirmed the potential for carryovers anticipated for the proposed workflow. In our hands, however, the presence of these species did not appear to hamper the characterization of low-abundance PTMs.

The m/z values obtained from the IMS-MS determination (provided on the y-axis of the heat-map in FIG. 2) were submitted to the same data treatment described above, and then used to search the custom registry. This operation yielded the same database hits produced by the ESI-MS data listed in Table 1. In this case, the experimental values afforded by the canonical ribonucleotides displayed an average of 13 ppm deviation from the theoretical values provided by their elemental composition, which is consistent with the typical accuracy achieved with this type of instrumentation. In analogy with the ESI-MS data displayed in FIG. 1, carryover species contributed significantly to the complexity of the observed heat-map, but did not have any adverse effect on PTM detection.

Example IV

The Following Example Describes Assignment of Structure and a Confirmation Process.

As part of the confirmation process for identifying a PTM RNA structure, a close match between experimental and theoretical masses calculated from known elemental compositions assists with achieving a positive identification. For species of this size, the level of closeness can is seen by the sub-ppm accuracy afforded by the instrument. This can greatly reduce the number of possible elemental compositions that could match the experimental data, thus minimizing the risk of erroneous interpretations (Quinn et al., 2013). However, regardless of the accuracy afforded by the available instrumentation, positive identification cannot be based solely on matching mass values, but must receive further corroboration by gas-phase fragmentation data consistent with the putative analyte structure. The facile cleavage of the N-glycosidic bond represents a characteristic dissociation channel that is diagnostic of nucleotide structures (Biemann and McCloskey, 1962; Crain, 1990a) and can be frequently employed to discriminate between isomeric forms present simultaneously in a sample (Quinn et al., 2013). Cleavage products can immediately reveal whether the modifying group may be situated on the phosphoribose or nucleobase moiety of the PTM structure. Further, these first-generation fragments can be submitted to subsequent isolation/activation steps in $MS^n$ experiments to obtain additional details on the nature and position of the modification (Quinn et al., 2013).

These points are exemplified by the analysis of the species detected at m/z 376.0684 in FIG. 1, which could potentially match different methyl-G isomers (i.e., 377.0762 u neutral mass in Table 1). In anionic mode, characteristic phosphoribose fragments produced by base loss were readily observed upon collisional activation of the deprotonated precursor in the LTQ-orbitrap analyzer (FIG. 3a). The fact that such products were detected in both methylated and unmethylated form (the latter with much greater abundance) was consistent with the presence of alternative isomers with the methyl group on the ribose (i.e., 2'-O-methyl-GMP (Gm) only possible match), or the purine system (i.e., 1-methyl-GMP (m'G), N2-methyl-GMP ($m^2G$), or 7-methyl-GMP ($m^7G$)). In positive ion mode, activation of the protonated species detected at m/z 378.0840 led to complementary products corresponding to free and methylated nucleobase (not shown) (Quinn et al., 2013). The first-generation fragment obtained in positive ion mode was subsequently submitted to both $MS^3$ (i.e., m/z 378→166→, FIG. 3b) and $MS^4$ analysis (i.e., m/z 378→166→124-+, FIG. 3b inset) to identify the position of the methyl group onto the purine system. The observed fragments were consistent with N1-, N2- and N7-methylation, thus supporting the simultaneous presence of these isomers in the S. cerevisiae sample.

The information obtained from these types of determinations corroborated the vast majority of the hits returned by database searching (marked with † in Table 1). The exception consisted of a few species for which limited signal intensity hindered the direct application of multiple activation steps. In this case, an alternative approach was implemented, which involved the application of consecutive reaction monitoring (CRM) (Tomer et al., 1988) to detect diagnostic precursor-product relationships characteristic of target nucleotides (Quinn et al., 2013). This technique affords excellent noise suppression and high duty cycle, which enhance the ability to detect low-abundance analytes in the presence of elevated background. However, its implementation requires prior knowledge of characteristic transitions to be monitored during analysis. In our case, this approach was facilitated by the predictable nature of ribonucleotide dissociation pathways (i.e., the above described base loss followed by ribose and nucleobase fragmentation), which provided series of specific precursor→product transitions for each entry of our non-redundant registry. The actual analyses were performed in automated mode with no operator intervention. In this way, the results of multiple CRM experiments were combined to corroborate the identity of low-abundance analytes and, in most cases, confirm the simultaneous presence of isomeric species (Table 1).

Figure 7A:
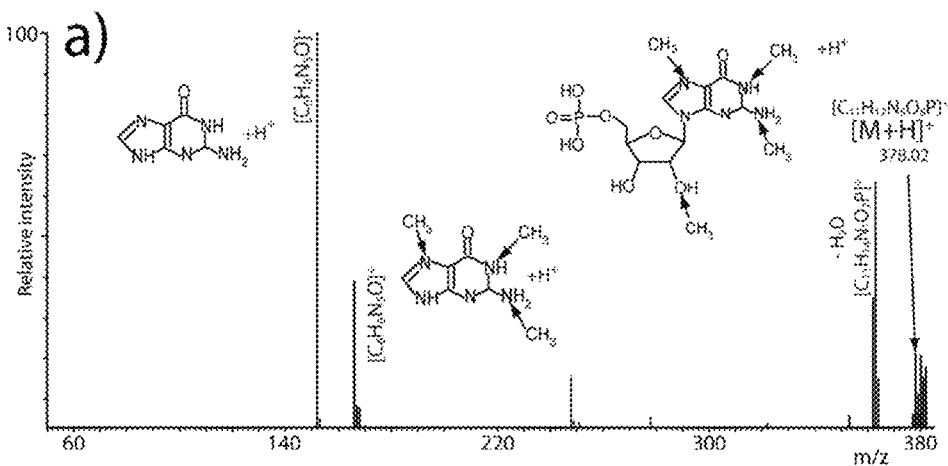
FIG. 7A-7C. Shows an exemplary product ion spectra obtained at the 7a) 3.672, 7b) 3.825, and 7c) 4.246 ms intervals of a mass-selected time-resolved dissociation experiment in which the precursor ion at m/z 378 was isolated in the mass-selective quadrupole, dispersed in the ion mobility element, and activated before final mass analysis. As described herein, the facile cleavage of the N-glycosidic bond enabled the discrimination of the Gm isomer with methylation on the ribose moiety, which provided an unmethylated purine fragment, from the remaining isomers that produced methylated purine fragments. Weaker signals characteristic of further cleavage of the purine system confirmed the presence of the remaining isomers. It should be noted that the signals observed at the selected time intervals displayed different abundances for methylated/unmethylated purine moieties, which were consistent with partial overlap between isomers on the time scale. The contributions of the individual isomers were recognized by employing reconstructed ion chromatograms (RICs) of unique diagnostic fragments (see FIG. 4A-4E).
Figure 7B:
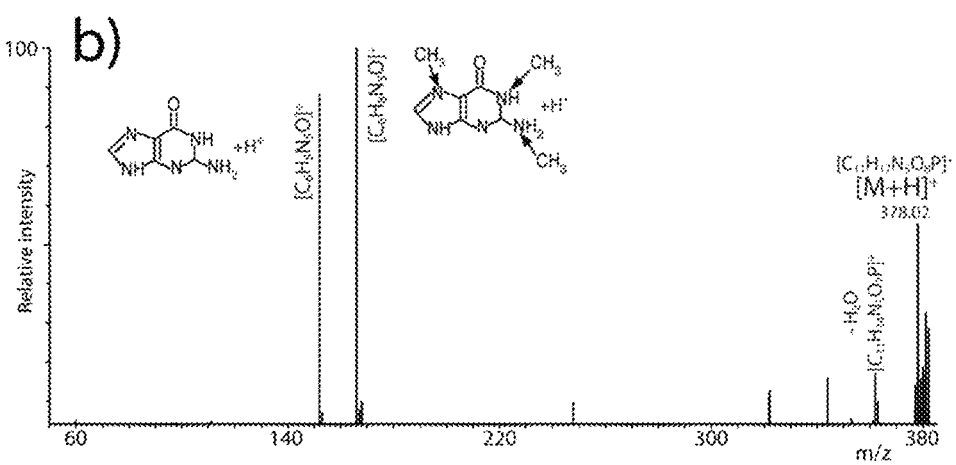
Figure 7C:
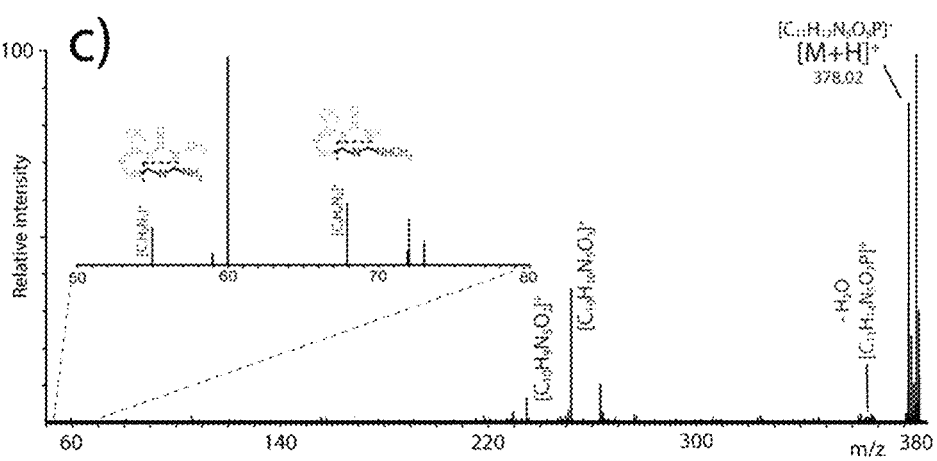

In the case of IMS-MS determinations, gas-phase dissociation was employed in analogous fashion to corroborate the initial assignments obtained by searching the observed m/z values in the custom registry. As described in previous work, the assignments were confirmed by activating in parallel the species dispersed on the time dimension by the ion mobility element, before transfer to the mass analyzer (Quinn et al., 2013). Called time aligned parallel (TAP) dissociation (Castro-Perez et al., 2011; Damen et al., 2009), this technique provided extensive fragmentation data that matched those observed for the yeast extract in the LTQ-orbitrap determinations. In addition, we explored an alternative characterization strategy that mimicked more traditional tandem MS spectrometry by fragmenting those species that were recognized as potential PTMs. As illustrated for the methyl-G species described above, this type of determination was completed by isolating the precursor ion at m/z 378 in the mass-selective quadruple, by allowing the various isomers to disperse on the time domain in the ion mobility element, and by then activating their gas-phase dissociation before final mass analysis. In what could be defined as mass-selected time-resolved dissociation experiment, the data obtained at different intervals displayed fragmentation patterns that were characteristic of the various methyl-G isomers (FIG. 7A-7C) and matched those observed in LTQ-orbitrap experiments (FIG. 3A-3B). As discussed above, dissociation of the N-glycosidic bond differentiated isomers with the methyl group located either on the phosphoribose or nucleobase moiety, whereas additional fragmentation of the latter identified the position of methylation sites on the purine system. A close examination of these data revealed that characteristic fragments, such as the methylated/unmethylated purine moieties, could be detected with distinctive intensity patterns in different sections of the time domain (compare for example panel 7a) and 7b) of FIG. 7A-7C), thus suggesting possible overlap between isomers with very similar mobility properties. The possible ambiguity was resolved by extracting the mobility profiles of diagnostic fragments unique for each isomer (FIG. 4A-4E). The resulting reconstructed ion chromatograms (RICs) clearly differentiated the individual species on the time scale, which helped explain the observed spectral overlap. When the mobility profile of m/z 378 was submitted to Gaussian fitting (FIG. 4a), the various components displayed a distribution that matched that of the individual RIC traces (panel 4b-4e), thus providing the weight of the different isomers in the sample mixture. The benefits and perils of mass-selected time-resolved dissociation will be expounded in a dedicated report.

None of the approaches described in this report employ specific $t_D$ values to achieve positive identification of the various species, which is instead based on corroborating fragmentation information. The time domain was used to achieve separation between isomers and to enable the observation of their specific fragmentation patterns. $t_D$ determinations showed an average reproducibility of ±0.006 ms over repeated analyses on different days, which could potentially support the utilization of $t_D$ as a unique identifying characteristic. However, in light of the number of experimental variables that may affect such quantity, reproducibility of this type of experiment across different instruments/platforms is contemplated before $t_D$ values can be employed directly for identification purposes. In the meantime, the ability to achieve positive corroboration was determined by the comprehensive nature of the structural information afforded by gas-phase dissociation in combination with the rather conservative principles employed for initial data reduction. Filtering out signals that did not possess recognizable isotopic patterns increased the efficiency of database searches and the effectiveness of subsequent analyses. While this criterion might have caused the occasional rejection of potentially valid information, conservative data reduction minimized the incidence of false positives by removing questionable signals from the initial mass lists. In this way, subsequent analyses targeted the species that had a legitimate probability of yielding viable fragmentation data for assignment confirmation.

Example V

The Following Example Describes Absolute Versus Relative Assessment of Modification Levels.

The implementation of these MS approaches, either individually or in concert, can provide a comprehensive inventory of the PTMs detectable in a lysate. However, the ability to merely identify their presence is not sufficient to support functional studies based on the evaluation of their expression levels as a function of experimental variables. The selected platform must be able to provide valid information on the respective abundances to appreciate possible up- or down-regulation and explore functional hypotheses. Classic quantitative approaches require the availability of target analyte in neat form to generate a calibration curve through serial dilutions, or to perform incremental additions to the original sample according to the standard additions method. Unfortunately, the broad implementation of such strategies has been severely limited by the inadequate availability of standards for the majority of known modifications. The workflow proposed here presents the opportunity to overcome this challenge by utilizing purified tRNA samples as intrinsic sources of PTMs in standard-addition determinations. According to this strategy, tRNA was added to the sample as an internal standard capable of releasing its PTMs at once during the RNase digestion step (Scheme 1). Samples containing incremental amounts of tRNA were then used to generate the signal/concentration curves necessary to determine unknown concentrations.

A basis for this strategy was tested by exploring the utilization of S. cerevisiae tRNA$^{Phe}$ (commercially available in isolated form) as a controlled source of selected PTMs. In preliminary experiments, predetermined amounts were submitted to the entire workflow to replicate actual application conditions. The concentration of intact tRNA$^{Phe}$ was monitored by UV absorption determinations through the steps preceding RNase digestion (Scheme 1), which revealed an average ~25% sample recovery. Upon hydrolysis, ESI-MS analysis on the LTQ-orbitrap displayed signals for the entire complement of PTMs represented in this type of tRNA, with no trace of undigested substrate (FIG. 8), thus indicating that the covalent modifications did not hamper nuclease activity. The analysis was repeated on samples that contained decreasing concentrations of tRNA$^{Phe}$ to evaluate the limit of detection of the proposed workflow. The results revealed that, on average, the various PTMs required a sample consumption in the amol range to produce a 3:1 or better signal-to-noise ratio (Table 1S). In addition to putative detection limits, this exercise enabled us to obtain individual signal/concentration curves that provided the signal response for each ribonucleotide in tRNA$^{Phe}$ (Table 1S).

Based on these results, we tested the utilization of tRNA$^{Phe}$ in a modified standard-addition procedure that involved mixing weighed amounts of S. cerevisiae pellet with accurately known increments of standard. This modus operandi ensured that standard and endogenous RNA underwent together the entire workflow. Also in this case, UV determinations were used to evaluate RNA recovery, which matched the ~25% average observed earlier for isolated standard. The excellent match between recoveries observed in the absence/presence of cell material indicated that lysis debris did not significantly interfere with phenol-chloroform extraction and subsequent workflow operations. The data obtained from the standard-addition series were used to generate the curves necessary to complete the quantitative determination of the PTMs in the extract (Table 2). The absence of accurate estimates of cellular volumes precluded a correct translation of extract concentrations into actual cellular concentrations. For this reason, the total amounts of PTMs in the sample were more conveniently expressed in terms of mol per gram of wet pellet (mol/g, Table 2), which were based on the weight of initial cell material employed in the determination. For conversion purposes, we estimated that 1 g of wet pellet corresponded to ~86 mL of a culture suspension with 0.3 OD$_{600}$. The results clearly displayed the typical gulf between abundant canonic ribonucleotides and low-abundance modifications representing the bulk of the observed analytes, which showcased the excellent dynamic range afforded by this approach. In the context of the detection limits obtained from isolated tRNA$^{Phe}$ (Table 1S), the observed values indicated that valid determinations could be comfortably accomplished for even the least abundant modifications (i.e., ac$^4$Cm and cmnm$^5$s$^2$U) with as little as 800 μg of wet pellet (~69 μL of a culture suspension with 0.3 OD$_{600}$). It should be noted that, although this determination covered a subset of the entire complement of cellular PTMs—those represented in tRNA$^{Phe}$—the utilization of different tRNAs or other controlled sources of natural PTMs could extend the coverage to virtually any type of modified ribonucleotides, thus making this strategy viable for a wide range of possible applications.

The proposed strategy can circumvent but not eliminate the hurdles associated with the dearth of suitable standards for rigorous quantitative determinations. In many cases, however, obtaining the absolute amount of a given PTM is not as crucial as monitoring its relative abundance versus others in the sample. In proteomics studies, for example, the ability to appreciate mutual variations of post-translational modifications—reliable indicators of up- and down regulation—is at least as valuable as the ability to determine their absolute levels. For this reason, we explored the possibility of utilizing the four canonical ribonucleotides, whose overall amounts and distributions are dependent on the cell's genetic makeup, as a convenient internal reference to observe relative variations within a given organism. More specifically, we combined their signal intensities to establish a multicomponent reference, which could fit the MS definition of a proxy base-peak, for quantifying the various PTMs in terms of abundance versus proxy (i.e., AvP). As shown in Table 2, this information was readily attainable for PTMs in the extract, regardless of their representation in a putative standard, thus providing a self-consistent and comprehensive measure of their relative abundances in the sample. We evaluated the effectiveness of this approach by comparing experimental AvP values obtained from isolated tRNA$^{Phe}$ with putative figures calculated for a fixed concentration by using the respective signal/concentration curves (Table 1S). The excellent match between corresponding values provided the justification for a broader application of this treatment to monitor the relative variations of PTM levels in actual cell material.

Example VI

The Following Example Describes Reproducibility of PTM Analysis.

Separate aliquots of the same S. cerevisiae pellet were submitted in parallel to the entire workflow to assess the technical reproducibility (precision) of the approach. The analysis of five individual samples consistently produced 40 hits. Their relative abundances were expressed in AvP units to enable direct comparisons of their distributions (Table 3). Overall, the values displayed an average of ±4.4% relative standard deviations (RSD %) for the PTMs, which offered a measure of the reproducibility of these determinations. Not surprisingly, the species at the higher end of the AvP scale displayed better reproducibility (i.e., smaller RSD % values) than those at the lower end, owing to the greater susceptibility of the latter to possible fluctuations of experimental conditions throughout the workflow. For comparison purposes, the reproducibility of the ESI-MS analysis itself was evaluated separately by repeating the determination of the same digestion mixture for a total of five times. The results provided an average RSD % of ±1.6% calculated from the PTMs in the sample, thus suggesting that workup operations, such as extraction/lysis, digestion, etc., contributed the lion's share of the overall ±4.4% uncertainty intrinsic in these determinations. It should be noted that in general the observed reproducibility benefited significantly from the utilization of relative rather than absolute notations.

Indeed, any experimental inconsistency affecting detection is typically expected to influence analyte and reference in the same direction, as they both undergo simultaneously the same procedure. When abundances are expressed in relation to the reference, these effects tend to cancel out, thus minimizing the impact of analytical fluctuations. This explains the observation that RSD % obtained directly from ion counts (absolute notation) were distinctively larger than those calculated from the corresponding AvPs (relative notation, Table 3).

In order to weigh sample-to-sample variability (i.e., biological reproducibility) against the observed technical reproducibility, we performed parallel analyses of individual samples grown in separate cultures under otherwise identical conditions. These experiments produced consistently the same hits obtained from the technical repeats, but their relative abundances displayed an average RSD % of ±7.8 (Table 3). At least at first sight, sample-to-sample fluctuations are typically ascribable to variations of total RNA in each sample. However, great effort was placed into growing the cultures in parallel under identical conditions, harvesting them at the same growth phase, and diluting the culture before aliquoting to approximate the same number of cells per sample. In addition, a closer look at the results revealed that the PTMs manifested widely different fluctuation levels from one another (e.g., compare ±14% for D with ±2.9% for ac$^4$C/f$^5$Cm). Any variation of overall RNA content would be expected to affect PTMs in the same direction, leading to comparable swings. Therefore, these considerations ruled out possible variations of total RNA as a source of uncertainty and suggested the influence of uncontrolled experimental variables that will warrant further investigation. When evaluating the uncertainty intrinsic in these determinations it was observed that biological reproducibility of ±7.8% included also the ±4.4% contribution of the underlying technical reproducibility present in each determination. This shows the example range for S. cerevisiae. Taken together, these figures provided a measure of the typical range within which the incidence of PTMs may vary sample-to-sample under strictly controlled conditions in these yeast experiments. Determining such range for the specific system under investigation is contemplated for increased confidence whether a certain variation is significant and may be unambiguously attributed to actual biological factors rather than mere sample variability.

Example VII

The Following Example Describes Epitranscriptomic Profiling.

Heat-maps generated by IMS-MS analysis were analyzed as direct representations of global PTM profiles. In this type of plot, the independent variables describing molecular mass and ion mobility behavior are dispersed onto orthogonal dimensions. Their intersection is unique for each analyte and enables their accurate differentiation. For this reason, a heat-map can provide a comprehensive view of the distribution of species in the sample. As exemplified in FIG. 2, the full complement of cellular PTMs, i.e. a full profile, and carryovers from the original lysate was observed in a single experiment that placed the abundances on a common scale. The visual nature of these plots lends itself to immediate comparisons between related samples. For example, inspection of the map obtained from a sample grown in synthetic complete medium (SC, FIG. 5*a*) revealed numerous signals in common with those observed for the YPD sample (FIG. 2), which corresponded to legitimate PTMs. These findings were readily confirmed by performing database searching of their respective m/z values, which led to the positive identification of 49 hits corroborated by gas-phase activation experiments (Table 4). Of this total, 40 hits matched PTMs observed in the YPD analysis (Table 1), whereas the remaining 8 were unique for this sample. The vast majority of the discrepancies between the SC and YPD samples corresponded instead to different carryover components, a direct consequence of the widely different compositions of these growth media and their putative effects on cell metabolism.

Visual comparison are contemplated to provide qualitative information on the presence/absence of a certain PTM or PTMs, then actual data subtraction can reveal more subtle differences between related heat-maps and provide an assessment of the different levels of common PTMs. This type of analysis was accomplished by expressing the intensity scales in AvP units to enable axes alignment and point-by-point subtraction. The resulting differential plot highlighted the subtle changes experienced by low-abundance species, such as ac$^4$C and f$^5$Cm (FIG. 5*b*). Overall, 30 of the 38 common PTMs were found to be more abundant in the SC than in the YPD sample, whereas the remaining 8 were less abundant. A closer look at the relative deviations featured in the differential plot showed that several of them exceeded the average RSD % of ±7.8% that expresses the biological reproducibility for these types of yeast samples (Table 4). A more accurate assessment of the individual variations was obtained by comparing such deviations with the corresponding individual uncertainties provided in Table 3. This analysis indicated that the differences between SC and YPD profiles were confidently ascribable to the effects of the distinct growth media on *S. cerevisiae* metabolism, which represented the controlled variable between these datasets. Metabolic states can influence the expression of PTMs through the different metabolic pathways responsible for their biogenesis. At the same time, the enzymatic infrastructure that constitutes such pathways is coded by the genome of the organism under consideration. Therefore, global PTM profiles reflect the intersection of the very specific genetic and metabolic makeups of the respective cells. We explored the ability of the proposed approach to tackle this source of diversity by analyzing different microorganisms and comparing their PTM profiles. To this end, *E. coli* cultures were grown in the same SC medium utilized for *S. cerevisiae*, in such a way as to eliminate the type of available nutrients as an environmental variable. As expected, the recorded heat-maps (FIG. 6a) differed significantly from those afforded by the corresponding *S. cerevisiae* sample (FIG. 5a). The plot obtained by subtracting the former from the latter served to accurately assess such differences and to guide subsequent analysis (FIG. 6b). The enlargement helps illustrate the type of variations afforded by low-abundance modifications. Overall, the *E. coli* sample provided a total of 30 hits, of which 23 were in common with *S. cerevisiae* (Table 2S). The common hits displayed relative deviations ranging from $1.68 \times 10^{-2}$% to 173%, many of which exceeded the RSD % values obtained from biological repeats of either organism. This observation provided excellent indications that these deviations were statistically significant, consistent with the considerable evolutionary distance between *E. coli* (a prokaryote) and *S. cerevisiae* (a eukaryote) in the phylogenetic tree.

TABLE 1

Hits obtained by searching the ESI-MS data in FIG. 1 against the non-redundant database generated in house (by combining data from the RNA Modifications and Modomics Databases, see Examples). The experimental mass of the neutral species is expressed in mass units (u). Monoisotopic mass was calculated from the respective elemental composition.

| Exp. mass (u) | Monoisotopic (u) | Hit[1] |
|---|---|---|
| 323.0519 | 323.05185 | $C^{\ddagger}$ |
| 324.0359 | 324.03587 | $Y^{\ddagger}, U^{\ddagger}$ |
| 326.0515 | 326.05152 | $D^{\ddagger}$ |
| 337.0675 | 337.06750 | $m^3C, m^5C, Cm^{\ddagger}, m^4C^*$ |
| 338.0515 | 338.05152 | $m^3Y^*, Um^{\ddagger}, m^5U, m^1Y, Ym^{\ddagger*}, m^3U$ |
| 347.0631 | 347.06308 | $A^{\ddagger}$ |
| 348.0471 | 348.04710 | $I^{\ddagger}$ |
| 361.0787 | 361.07873 | $m^1A, m^2A^*, m^6A, m^8A^*, Am^{\ddagger}$ |
| 363.0580 | 363.05800 | $G^{\ddagger}$ |
| 365.0623 | 365.06242 | $ac^4C^{\ddagger*}, f^5Cm^{\ddagger*}$ |
| 375.0942 | 375.09438 | $m^6Am^*, m^1Am^*, m^6_2A^{\ddagger*}$ |
| 377.0762 | 377.07365 | $m^1G^{\ddagger}, m^2G^{\ddagger}, m^7G^{\ddagger}, Gm^{\ddagger}$ |
| 379.0762 | 379.07807 | $ac^4Cm^{\ddagger*}$ |
| 381.0572 | 381.05733 | $ncm^5U^*$ |
| 391.0893 | 391.08923 | $m^1Gm^*, m^2_2G, preQ1^*, m^2_7G$ |
| 427.0429 | 427.04505 | $cmnm^5s^2U$ |
| 492.1005 | 492.10059 | $t^6A^{\ddagger}$ |
| 588.1580 | 588.15811 | $yW^{\ddagger}$ |

TABLE 1-continued

Hits obtained by searching the ESI-MS data in FIG. 1 against the non-redundant database generated in house (by combining data from the RNA Modifications and Modomics Databases, see Examples). The experimental mass of the neutral species is expressed in mass units (u). Monoisotopic mass was calculated from the respective elemental composition.

| Exp. mass (u) | Monoisotopic (u) | Hit[1] |
|---|---|---|

[1]Full names available at world wide web://mods.rna.albany.edu/ Hosted by The RNA Institute, College of Arts and Sciences, State University of New York at Albany and world wide web://modomics.genesilico.pl/.
‡Assignments corroborated by tandem mass spectrometry (i.e., MS$^n$ and CRM determinations). Modifications previously unreported in *S. cerevisiae*.

TABLE 2

Quantitative determination of ribonucleotides present in total RNA extract of *S. cerevisiae*. This standard-additions determination used tRNA$^{Phe}$ purified from *S. cerevisiae* to achieve in situ release of PTM standards (see Examples). Name abbreviation and neutral experimental mass in mass units (u) are provided for each ribonucleotide.

| Hit[1] | Exp. mass (u) | Conc. (M)[2] | Amount (mol/g)[3] | Exp. AvP[4] |
|---|---|---|---|---|
| C | 323.0519 | $2.60 \times 10^{-5}$ | $1.25 \times 10^{-7}$ | 28.7 |
| U/Ψ | 324.0359 | $2.26 \times 10^{-5}$ | $1.09 \times 10^{-7}$ | 22.0 |
| D | 326.0515 | $2.40 \times 10^{-6}$ | $1.16 \times 10^{-8}$ | 2.95 |
| $m^3C, m^5C, Cm, m^4C$ | 337.0675 | $2.48 \times 10^{-7}$ | $1.19 \times 10^{-9}$ | $2.45 \times 10^{-1}$ |
| $m^3Y, Um, m^5U, m^1Y, Ym, m^3U$ | 338.0515 | NA | NA | 1.03 |
| A | 347.0631 | $2.41 \times 10^{-5}$ | $1.16 \times 10^{-7}$ | 21.6 |
| I | 348.0471 | NA | NA | $1.44 \times 10^{-1}$ |
| $m^1A, m^2A, m^6A, Am, m^8A$ | 361.0787 | $4.40 \times 10^{-7}$ | $4.40 \times 10^{-9}$ | $1.02 \times 10^{-1}$ |
| G | 363.0580 | $2.42 \times 10^{-5}$ | $1.17 \times 10^{-7}$ | 27.7 |
| $ac^4C, f^5Cm$ | 365.0623 | NA | NA | $4.75 \times 10^{-1}$ |
| $m^6Am, m^1Am, m^6_2A$ | 375.0942 | NA | NA | $5.01 \times 10^{-3}$ |
| $m^1G, m^2G, m^7G, Gm$ | 377.0762 | $1.32 \times 10^{-7}$ | $6.34 \times 10^{-10}$ | 1.02 |
| $ac^4Cm$ | 379.0762 | NA | NA | $6.85 \times 10^{-3}$ |
| $ncm^5U$ | 381.0572 | NA | NA | $3.37 \times 10^{-2}$ |
| $m^1Gm, m^2_2G, preQ1, m^2_7G$ | 391.0893 | $5.64 \times 10^{-7}$ | $2.72 \times 10^{-9}$ | $6.26 \times 10^{-1}$ |
| $cmnm^5s^2U$ | 427.0429 | NA | NA | $1.02 \times 10^{-2}$ |
| $t^6A$ | 492.1005 | NA | NA | $1.34 \times 10^{-1}$ |
| yW | 588.1580 | $2.50 \times 10^{-7}$ | $1.20 \times 10^{-9}$ | $1.84 \times 10^{-1}$ |

[1]Full names available at world wide web://mods.rna.albany.edu/ Hosted by The RNA Institute, College of Arts and Sciences, State University of New York at Albany and world wide web://modomics.genesilico.pl/.
[2]The concentration of each PTM in the extract was calculated from the respective curve afforded by the standard-additions determination. This amount accounts also for the ~25% recovery estimated from the standard tRNA$^{Phe}$ added to each sample. NA indicates PTMs that could not be determined due to their absence in the standard tRNA$^{Phe}$.
[3]The amount of each PTM per gram of wet pellet was calculated from the respective extract concentration by taking in account the initial weight of intact *S. cerevisiae* material.
[4]For each PTM, the value of abundance versus proxy (AvP) was calculated from the respective signal intensity as percentage of the sum of the intensities of the four canonic ribonucleotides (see Examples). Each value was the average of five repeat analyses. This amount represents a relative measure of the abundance of each PTM in the sample, which can be always calculated across the board in the absence of PTM standards (see Examples).

TABLE 3

Reproducibility of ESI-MS analysis of total RNA extract from *S. cerevisiae* grown in YPD medium.

| Hit[1] | Exp. mass (u) | Technical reproducibility[2] | | Biological reproducibility[3] | |
|---|---|---|---|---|---|
| | | Ave. AvP | AvP RSD % | Ave AvP | AvP RSD % |
| C | 323.0519 | 28.7 | ±5.0 | 29.1 | ±4.9 |
| Y, U | 324.0359 | 22.0 | ±4.1 | 22.1 | ±9.1 |
| D | 326.0515 | 2.95 | ±3.7 | 1.18 | ±14 |
| $m^3C$, $m^5C$, Cm, $m^4C$ | 337.0675 | $2.45 \times 10^{-1}$ | ±5.5 | $7.04 \times 10^{-1}$ | ±7.5 |
| $m^3Y$, Um, $m^5U$, $m^1Y$, Ym, $m^3U$ | 338.0515 | 1.03 | ±3.6 | $7.28 \times 10^{-1}$ | ±5.5 |
| A | 347.0631 | 21.6 | ±4.7 | 21.3 | ±6.6 |
| I | 348.0471 | $1.44 \times 10^{-1}$ | ±3.8 | $7.31 \times 10^{-2}$ | ±6.1 |
| $m^1A$, $m^2A$, $m^6A$, $m^8A$, Am | 361.0787 | $1.02 \times 10^{-1}$ | ±6.9 | $4.53 \times 10^{-1}$ | ±11 |
| G | 363.0580 | 27.7 | ±2.6 | 27.4 | ±2.2 |
| $ac^4C$, $f^5Cm$ | 365.0623 | $4.75 \times 10^{-1}$ | ±2.2 | $4.87 \times 10^{-1}$ | ±2.9 |
| $m^6Am$, $m^1Am$, $m^6_2A$ | 375.0942 | $5.01 \times 10^{-3}$ | ±9.9 | $5.15 \times 10^{-2}$ | ±11 |
| $m^1G$, $m^2G$, $m^7G$, Gm | 377.0762 | 1.02 | ±2.5 | $7.52 \times 10^{-1}$ | ±4.8 |
| $ac^4Cm$ | 379.0762 | $6.85 \times 10^{-3}$ | ±4.0 | $7.34 \times 10^{-3}$ | ±5.4 |
| $ncm^5U$ | 381.0572 | $3.37 \times 10^{-2}$ | ±6.3 | $2.76 \times 10^{-2}$ | ±13 |
| $m^1Gm$, $m^2_2G$, preQ1, $m^2_7G$ | 391.0893 | $6.26 \times 10^{-1}$ | ±4.9 | $2.25 \times 10^{-1}$ | ±9.9 |
| $cmnm^5s^2U$ | 427.0429 | $1.02 \times 10^{-1}$ | ±1.2 | $4.62 \times 10^{-3}$ | ±6.5 |
| $t^6A$ | 492.1005 | $1.34 \times 10^{-1}$ | ±6.5 | $5.89 \times 10^{-2}$ | ±8.9 |
| yW | 588.1580 | $1.84 \times 10^{-1}$ | ±1.3 | $1.86 \times 10^{-2}$ | ±9.7 |
| | | | Ave. ±4.4% | | Ave. ±7.8% |

[1] Full names available at world wide web://mods.rna.albany.edu/ Hosted by The RNA Institute, College of Arts and Sciences, State University of New York at Albany and world wide web://modomics.genesilico.pl/.
[2] Assessed by applying the proposed workflow to five separate aliquots of the same *S. cerevisiae* pellet. For each PTM, abundance versus proxy (AvP) was calculated from the respective signal intensity as percentage of the sum of the intensities of the four canonic ribonucleotides (see Examples). Average and relative standard deviation (RSD %) are reported.
[3] Assessed from five different samples of *S. cerevisiae* grown under identical conditions in separate YPD cultures.

TABLE 4

Hits provided by a total RNA extract from *S. cerevisiae* grown in synthetic complete medium (SC).

| Hit[1] | Exp. mass (u) | Exp. AvP[2] | Rel. dev. (%)[3] |
|---|---|---|---|
| C | 323.0519 | 21.5 | +28.8 |
| Y, U | 324.0359 | 25.7 | -15.4 |
| D | 326.0515 | 2.62 | +11.9 |
| $m^3C$, $m^5C$, Cm, $m^4C$ | 337.0675 | 1.13 | -129 |
| $m^3Y$, Um, $m^5U$, $m^1Y$, Ym, $m^3U$ | 338.0515 | 1.24 | -18.4 |
| $ho^5U$ | 340.0308 | $9.94 \times 10^{-2}$ | NA |
| A | 347.0631 | 23.7 | -9.20 |
| I | 348.0471 | $1.42 \times 10^{-1}$ | +1.61 |
| $m^1A$, $m^2A$, $m^6A$, Am | 361.0787 | $4.78 \times 10^{-1}$ | -130 |
| $m^1I$, Im | 362.0628 | $2.52 \times 10^{-2}$ | NA |
| G | 363.0580 | 29.1 | -5.13 |
| $ac^4C$, $f^5Cm$ | 365.0624 | $5.72 \times 10^{-1}$ | -18.6 |
| $m^6Am$, $m^1Am$, $m^6_2A$ | 375.0944 | $3.53 \times 10^{-2}$ | -150 |
| $m^1G$, $m^2G$, $m^7G$, Gm | 377.0737 | 1.32 | -25.3 |
| $ac^4Cm$ | 379.0781 | $1.75 \times 10^{-2}$ | -87.4 |
| $ncm^5U$ | 381.0573 | $9.02 \times 10^{-2}$ | -91.2 |
| $m^1Gm$, $m^2_2G$, preQ1, $m^2_7G$ | 391.0892 | $4.85 \times 10^{-1}$ | +25.4 |
| $ncm^5Um$ | 395.0730 | $2.33 \times 10^{-2}$ | NA |
| $mcm^5U$ | 396.0570 | $6.24 \times 10^{-2}$ | NA |
| $mcm^5s^2U$ | 412.0342 | $6.37 \times 10^{-2}$ | NA |
| $i^6A$ | 415.1257 | $1.54 \times 10^{-1}$ | NA |
| $t^6A$ | 492.1006 | $1.49 \times 10^{-1}$ | -10.7 |
| Ar(p) | 559.0717 | $9.71 \times 10^{-3}$ | NA |
| yW | 588.15811 | $4.20 \times 10^{-2}$ | +126 |

[1] Full names available at world wide web://mods.rna.albany.edu/ Hosted by The RNA Institute, College of Arts and Sciences, State University of New York at Albany and world wide web://modomics.genesilico.pl/.
[2] Abundance versus proxy (AvP) calculated from the respective signal intensity as percentage of the sum of the intensities of the four canonic ribonucleotides (see Examples). Each value was the average of five repeat analyses.
[3] Relative deviations between AvPs obtained from *S. cerevisiae* grown in YPD and SC under otherwise identical conditions. NA indicates deviations that could not be calculated due to the absence of the corresponding species in the YPD samples.

TABLE 4A

Exemplary names and structures of RNA having modifications identified in a total RNA extract from *S. cerevisiae* grown in synthetic complete medium (SC) as identified in Table 4. Structures from world wide web://mods.rna.albany.edu/ Hosted by The RNA Institute, College of Arts and Sciences, State University of New York at Albany and world wide web://modomics.genesilico.pl/.

| Hit | Names (common) (X- Not in database) | Structure(s), respectively (X- Not in database) |
|---|---|---|
| C | cytidine | 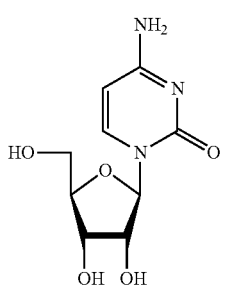 |

TABLE 4A-continued

*Exemplary names and structures of RNA having modifications identified in a total RNA extract from S. cerevisiae grown in synthetic complete medium (SC) as identified in Table 4. Structures from world wide web://mods.rna.albany.edu/ Hosted by The RNA Institute, College of Arts and Sciences, State University of New York at Albany and world wide web://modomics.genesilico.pl/.*

| Hit | Names (common) (X- Not in database) | Structure(s), respectively (X- Not in database) |
|---|---|---|
| Y, U | Pseudouridine, uridine | 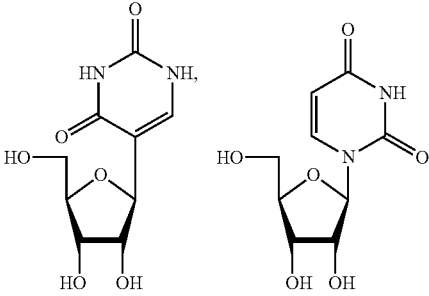 |
| D | dihydrouridine | |
| m³C, m⁵C, Cm, m⁴C | 3-methylcytidine, 5-methylcytidine, 2'-O-methylcytidine, N⁴-methylcytidine | 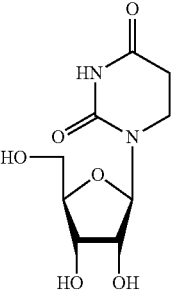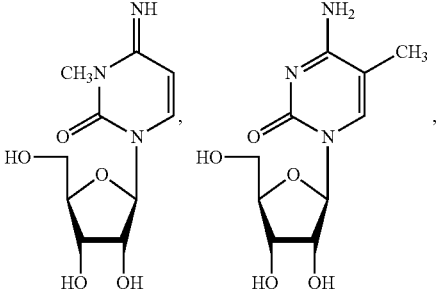 |

TABLE 4A-continued

*Exemplary names and structures of RNA having modifications identified in a total RNA extract from S. cerevisiae grown in synthetic complete medium (SC) as identified in Table 4. Structures from world wide web://mods.rna.albany.edu/ Hosted by The RNA Institute, College of Arts and Sciences, State University of New York at Albany and world wide web://modomics.genesilico.pl/.*

| Hit | Names (common) (X- Not in database) | Structure(s), respectively (X- Not in database) |
|---|---|---|
| $m^3Y$, Um, $m^5U$, $m^1Y$, Ym, $m^3U$ | 3-methylpseudouridine, 2'-O-methyluridine, 5-methyluridine, 1-methylpseudouridine, 2'-O-methylpseudouridine, 3-methyluridine | 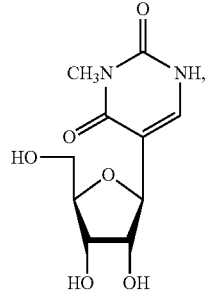 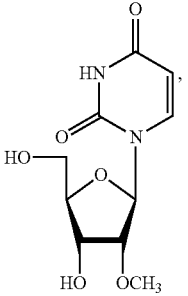 |
| $ho^5U$ | 5-hydroxyuridine | 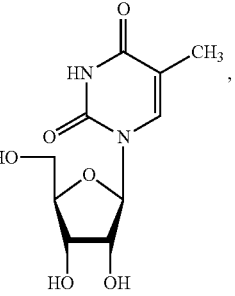 |
| A | adenosine | 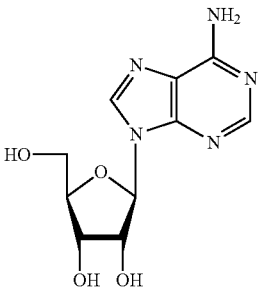 |

TABLE 4A-continued

Exemplary names and structures of RNA having modifications identified in a total RNA extract from *S. cerevisiae* grown in synthetic complete medium (SC) as identified in Table 4. Structures from world wide web://mods.rna.albany.edu/ Hosted by The RNA Institute, College of Arts and Sciences, State University of New York at Albany and world wide web://modomics.genesilico.pl/.

| Hit | Names (common) (X- Not in database) | Structure(s), respectively (X- Not in database) |
|---|---|---|
| I | inosine | |
| $m^1A$, $m^2A$, $m^6A$, Am | 1-methyladenosine, 2-methyladenosine, $N^6$-methyladenosine, 2'-O-methyladenosine, | |
| $m^1I$, Im | 1-methylinosine, 2'-O-methylinosine | |

TABLE 4A-continued

*Exemplary names and structures of RNA having modifications identified in a total RNA extract from S. cerevisiae grown in synthetic complete medium (SC) as identified in Table 4. Structures from world wide web://mods.rna.albany.edu/ Hosted by The RNA Institute, College of Arts and Sciences, State University of New York at Albany and world wide web://modomics.genesilico.pl/.*

| Hit | Names (common) (X- Not in database) | Structure(s), respectively (X- Not in database) |
|---|---|---|
| G | guanosine | |
| ac⁴C, f⁵Cm | $N^4$-acetylcytidine, 5-formyl-2'-O-methylcytidine | |
| m⁶Am, m¹Am, m⁶₂A | $N^6$,2'-O-dimethyladenosine, 1,2'-O-dimethyladenosine, $N^6,N^6$-dimethyladenosine | |
| m¹G, m²G, m⁷G, Gm | 1-methylguanosine, $N^2$-methylguanosine, 7-methylguanosine, 2'-O-methylguanosine | |

TABLE 4A-continued

*Exemplary names and structures of RNA having modifications identified in a total RNA extract from S. cerevisiae grown in synthetic complete medium (SC) as identified in Table 4. Structures from world wide web://mods.rna.albany.edu/ Hosted by The RNA Institute, College of Arts and Sciences, State University of New York at Albany and world wide web://modomics.genesilico.pl/.*

| Hit | Names (common) (X- Not in database) | Structure(s), respectively (X- Not in database) |
|---|---|---|
| ac⁴Cm | N⁴-acetyl-2′-O-methylcytidine | |
| ncm⁵U | 5-carbamoylmethyluridine | |
| m¹Gm, m²₂G, preQ1, m²₇G | 1,2′-O-dimethylguanosine, N²,N²-dimethylguanosine, 7-aminomethyl-7-deazaguanosine, X | |

TABLE 4A-continued

*Exemplary names and structures of RNA having modifications identified in a total RNA extract from S. cerevisiae grown in synthetic complete medium (SC) as identified in Table 4. Structures from world wide web://mods.rna.albany.edu/ Hosted by The RNA Institute, College of Arts and Sciences, State University of New York at Albany and world wide web://modomics.genesilico.pl/.*

| Hit | Names (common) (X- Not in database) | Structure(s), respectively (X- Not in database) |
|---|---|---|
| ncm⁵Um | 5-carbamoylmethyl-2'-O-methyluridine | |
| mcm⁵U | 5-methoxycarbonylmethyluridine | |
| cmnm⁵s²U | 5-carboxymethylaminomethyl-2-thiouridine | |
| i⁶A | N⁶-isopentenyladenosine | |

TABLE 4A-continued

*Exemplary names and structures of RNA having modifications identified in a total RNA extract from S. cerevisiae grown in synthetic complete medium (SC) as identified in Table 4. Structures from world wide web://mods.rna.albany.edu/ Hosted by The RNA Institute, College of Arts and Sciences, State University of New York at Albany and world wide web://modomics.genesilico.pl/.*

| Hit | Names (common) (X- Not in database) | Structure(s), respectively (X- Not in database) |
|---|---|---|
| $t^6A$ | $N^6$-threonylcarbamoyladenosine | 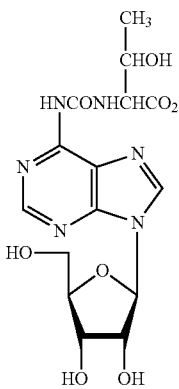 |
| Ar(p) | 2'-O-ribosyladenosine (phosphate) | 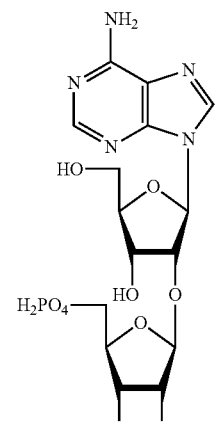 |
| yW | wybutosine | 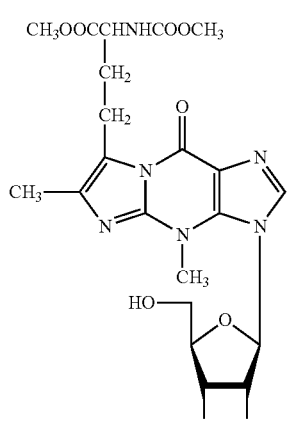 |

TABLE 1S

Figure 8:
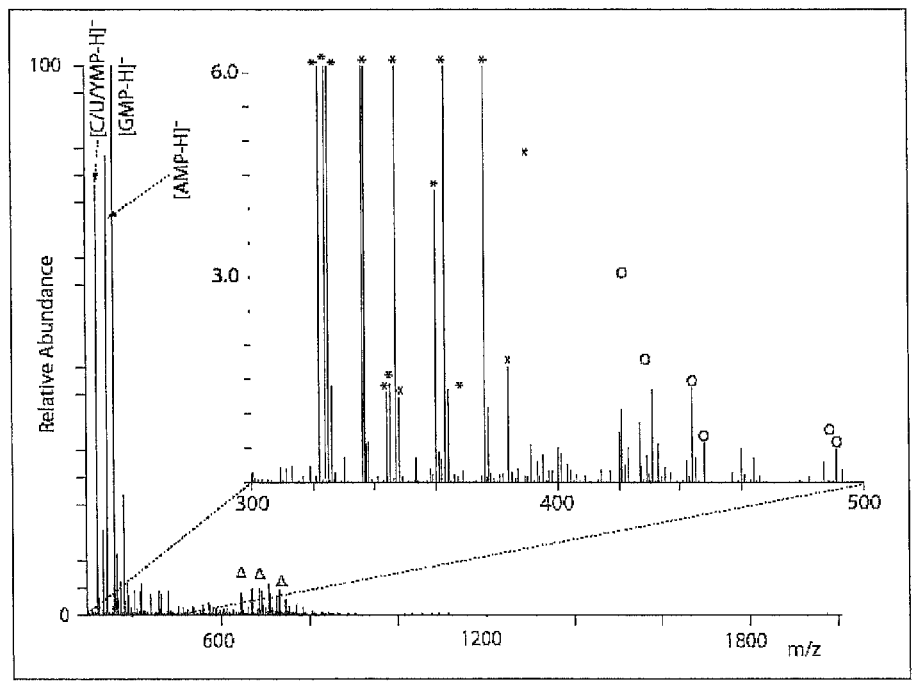
FIG. 8. Shows an exemplary ESI-MS spectrum of digestion mixture obtained in negative ion mode from *S. cerevisiae* tRNA$^{Phe}$. The enlargement shows the region containing the majority of the PTMs. Signals marked with * are hits from our custom modifications registry; Δ proton-bound dimers of the most abundant species in the spectrum; o species detected also in the blank. No undigested tRNA$^{Phe}$ was observed in the high m/z range.

Figures of merit obtained from the analysis of isolated tRNA$^{Phe}$ from S. cerevisiae (FIG. 8). The abbreviation for each ribonucleotide is provided together with the corresponding monoisotopic neutral mass in mass units (u) and the number of equivalents present in each mole of initial tRNA$^{Phe}$.

| Species | Exp. mass (u) | Equivalent per mole | [1]Detection limit (mol) | [2]Response (m, q) | [3]Theoretical AvP (%) | [3]Experimental AvP (%) |
|---|---|---|---|---|---|---|
| C | 323.0519 | 15 | 3.44 × 10$^{-17}$ | 1.61 × 10$^{11}$, 5.01 | 24.7 | 24.6 |
| U/Ψ | 323.0279 | 14 | 2.68 × 10$^{-17}$ | 1.53 × 10$^{11}$, 2.03 × 10$^1$ | 21.9 | 21.6 |
| D | 326.0514 | 2 | 1.80 × 10$^{-17}$ | 1.82 × 10$^{11}$, 3.01 × 10$^1$ | 3.73 | 3.75 |
| m$^3$C, m$^5$C, Cm | 337.0674 | 3 | 5.50 × 10$^{-17}$ | 1.41 × 10$^{11}$, 8.00 × 10$^1$ | 4.33 | 4.34 |
| A | 347.0630 | 17 | 9.58 × 10$^{-17}$ | 1.31 × 10$^{11}$, 9.20 | 22.8 | 22.1 |
| m$^1$A | 361.0787 | 1 | 9.29 × 10$^{-17}$ | 3.52 × 10$^{10}$, 3.03 × 10$^1$ | 3.60 × 10$^{-1}$ | 3.75 × 10$^{-1}$ |
| G | 363.0579 | 18 | 1.55 × 10$^{-17}$ | 1.71 × 10$^{11}$, 3.78 × 10$^1$ | 31.5 | 31.7 |
| m$^2$G, Gm | 377.0718 | 3 | 5.29 × 10$^{-18}$ | 1.24 × 10$^{11}$, 5.88 × 10$^1$ | 3.81 | 3.61 |
| m$^2_2$G | 391.0892 | 1 | 2.44 × 10$^{-17}$ | 1.71 × 10$^{11}$, 2.07 × 10$^1$ | 1.75 | 1.60 |
| yW | 588.1571 | 1 | 4.14 × 10$^{-17}$ | 1.10 × 10$^{11}$, 1.71 × 10$^1$ | 1.13 | 1.16 |

[1]The limit of detection (LOD) was obtained by calculating the moles of each ribonucleotide, which provided at least a 3:1 signal to noise ratio. The results are the average of five repeat determinations. The calculation accounted for an average of ~0.093 uL sample consumption during ESI-MS analysis and a ~25% sample recovery for the entire work flow (see Examples).
[2]The response for each ribonucleotide was calculated by averaging the signals of five repeat determinations for samples with decreasing concentration of tRNA$^{Phe}$. Each signal average was plotted against the respective concentration to obtain signal/concentration curves with the indicated slopes (m in counts/M) and intercepts (q in counts).
[3]For each ribonucleotide, the value of abundance versus proxy (AvP) was calculated by dividing the respective intensity by the sum of the intensities of the four canonic ribonucleotides (see Examples). The experimental AvP was calculated directly from the ESI-MS data. The theoretical value was obtained from the intensity that would be expected from the analysis of exactly 1M of tRNA$^{Phe}$, which was calculated by substituting the equivalents per mole of each species into the respective response curve. The excellent match between theoretical and experimental justifies the utilization of AvP to monitor fluctuations of PTM expression (see Examples).

TABLE 2S

Hits provided by a total RNA extract from E. coli grown in synthetic complete medium (SC).

| Hit | Exp. mass (u) | Average AvP (%) | Deviation (%)[1] |
|---|---|---|---|
| C | 323.0519 | 21.4 | +2.40 × 10$^{-1}$ |
| Y, U | 324.0357 | 22.1 | −15.0 |
| D | 326.0510 | 2.27 × 10$^{-1}$ | +1.68 × 10$^2$ |
| m$^3$C, m$^5$C, Cm, m$^4$C | 337.0673 | 8.08 × 10$^{-2}$ | 173 |
| m$^3$Y, Um, m$^5$U, m$^1$Y, Ym, m$^3$U | 338.0513 | 2.44 × 10$^{-1}$ | 134 |
| A | 347.0628 | 25.7 | −7.95 |
| I | 348.0468 | 3.54 × 10$^{-3}$ | 190 |
| m$^5$Cm, m$^4$Cm, m$^4_4$C | 351.0830 | 1.31 × 10$^{-2}$ | NA |
| mo$^5$U | 354.0463 | 3.53 × 10$^{-3}$ | NA |
| G | 363.0575 | 30.8 | −5.61 |
| ac$^4$C, f$^5$Cm | 365.0617 | 4.95 × 10$^{-1}$ | 14.3 |
| mnm$^5$U | 367.0776 | 2.86 × 10$^{-3}$ | NA |
| m$^1$G, m$^2$G, m$^7$G, Gm | 377.0720 | 2.26 × 10$^{-1}$ | 141 |
| cmo$^5$U, chm$^5$U | 398.0362 | 1.58 × 10$^{-1}$ | NA |

[1]Deviation from the average AvP obtained for the same PTM in S. cerevisiae grown in SC under identical conditions.

Example VIII

This Example Describes Comprehensive Ribonucleotide Modification Maps as Tracking Tools for the Multistage Processes Involved in Cell Transformation from Normalcy to Malignancy.

The systematic exploration of the interactome is typically supported by genomics and proteomics approaches that focus on nucleic acids and protein components. However, other cellular components traditionally viewed as products or intermediates of specific pathways can participate in regulatory mechanisms by influencing the interactome. For example, RNA is involved in protein synthesis and gene regulation, but its ability to undergo extensive post-transcriptional modification provides new opportunities for enzyme-based pathways to feedback at the mRNA-translation level to regulate protein expression. Therefore, an MS-based strategy to was developed to obtain comprehensive maps of RNA modifications, which were then used to explore the complex signaling pathways responsible for the multistage processes that take cells from normalcy to malignancy.

A. Methods.

RNA samples were obtained by phenol-chloroform extraction of E. coli MG1655 and S. cerevisiae 2998. When appropriate, aliquots of S. cerevisiae tRNA$^{phe}$ (Sigma-Aldrich) were introduced into the lysate as an internal standard. Additionally, S. cerevisiae BY1473 and the TRM and LHP1P knockdowns were obtained from Thermo Scientific. The starting material was hydrolyzed to mononucleotide mixtures by digestion with specific nucleases. Sample solutions were diluted to final concentrations of ~3 μM total ribonucleotides (NMPs) in 100 mM ammonium acetate and 10% 2-propanol.

Direct infusion nanospray analyses were performed either on a Thermo Scientific LTQ-Orbitrap Velos, or a Waters Synapt G2 HDMS mass spectrometer. High-resolution determinations and MS$^n$ were completed on the former by using an automated procedure. Ion mobility determinations and time aligned parallel (TAP) fragmentation were completed on the latter. Data interpretation employed Waters Driftscope software. (see FIGS. 9A and 9B for an overview of methods).

B. Results.

Data of each *E. coli* extract was collected in negative mode from m/z 300-700. Typical experimental masses of canonical ribonucleotides exhibited an average of ~800 ppb deviation from their calculated theoretical values. Reduced data from each extract was searched against a non-redundant database compiled by combining data from the RNA Modifications and Modomics Databases. A total of 36 hits were consistently obtained and subjected to fragmentation to confirm analyte structure by observing the characteristic cleavage of the N-glycosidic bond found in each ribonucleotide. Discrimination of isobaric species was achieved by employing $MS^n$ and IMS-MS experiments on each isobaric mixture.

Repeat analyses of an accurately known amount of naturally modified $tRNA^{phe}$ that was subjected to the entire workflow resulted in a sample recovery of ~25%. Cellular expression levels of RNA modifications were monitored quantitatively through the standard additions method by introducing incremental amounts of $tRNA^{phe}$ to the lysed material. Table A provides exemplary LOD and signal response information while Table AA shows exemplary structures including at least one new RNA modification found in *E. coli*.Tables B-D provide additional exemplary results of this analysis.

Figure 11A:
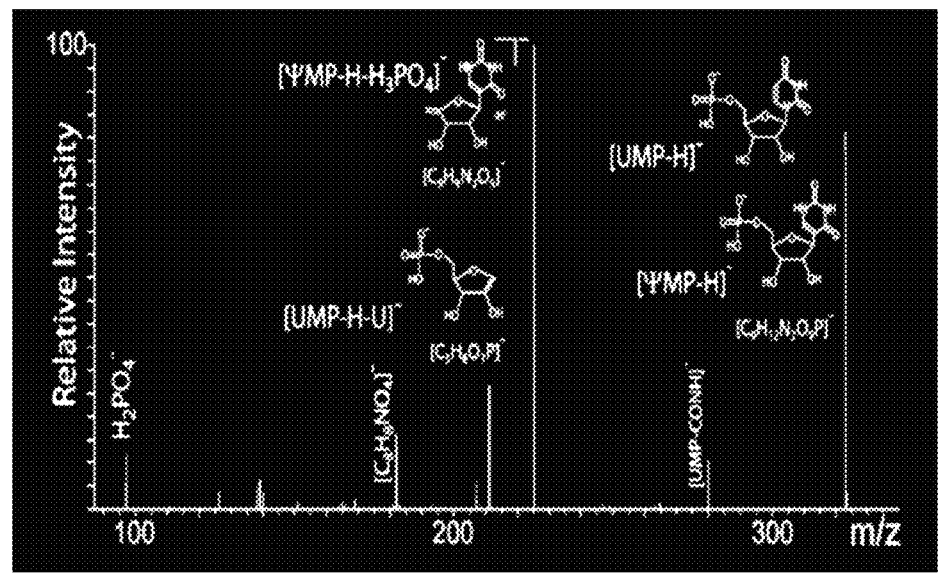
FIG. 11A-11C: Shows an exemplary discrimination of isobars. 11A) Tandem MS used to discriminate UMP and ΨMP by unique fragments. 11B) IMS-MS shows two distinct mobility profiles for UMP and ΨMP. 11C) Global profiling of extracts can be displayed as heat maps to show overall complexity.
Figure 11B:
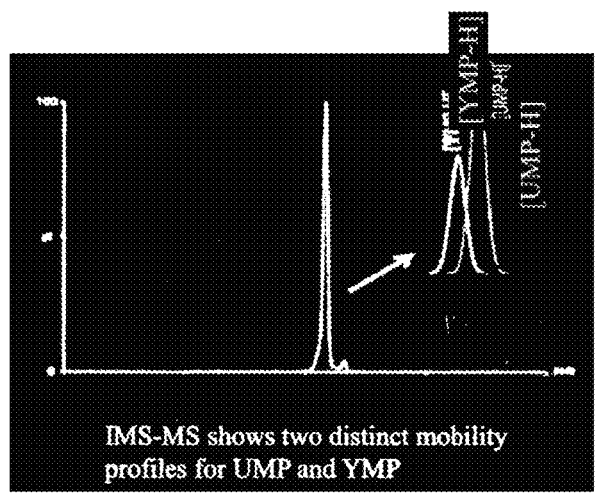
Figure 11C:
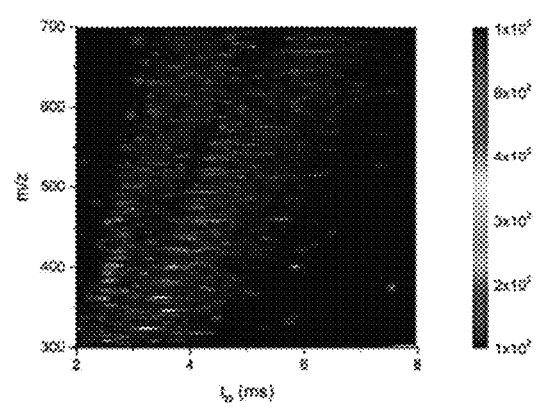

In order to obtain a convenient but rigorous way to compare relative abundances between samples, the abundance versus proxy (AvP) was calculated for each hit by dividing the respective intensity by the sum of the intensities of the four canonical ribonucleotides. The validity of this quantity was supported by the excellent match between experimental and theoretical values calculated for 1 M of $tRNA^{phe}$, knowing its normal content of RNA modifications. This quantity was then utilized to assess the technical and biological reproducibility of the proposed workflow, which amounted to ±9.4% and ±22% RSD %, respectively. FIG. 10A-10B shows exemplary tandem MS analysis of methyl-G from *E. coli* total RNA digest. 10A) MS/MS spectrum of methyl-G from *E. coli* total RNA digest. 10B) MS 3 spectrum obtained by activating m/z 376.09, 166.09. Inset: MS 4 spectrum obtained by activating m/Z. 376.09-166.09-123.84. FIG. 11A-11C shows an example of 11A) Tandem MS used to discriminate UMP and ΨMP by unique fragments. 11B) IMS-MS shows two distinct mobility profiles for UMP and ΨMP. 11C) Global profiling of extracts can be displayed as heat maps to show overall complexity.

1. Comparison of Modified RNA Structure Profiles Between *E. coli* and *S. cerevisiae*.

Figure 12:
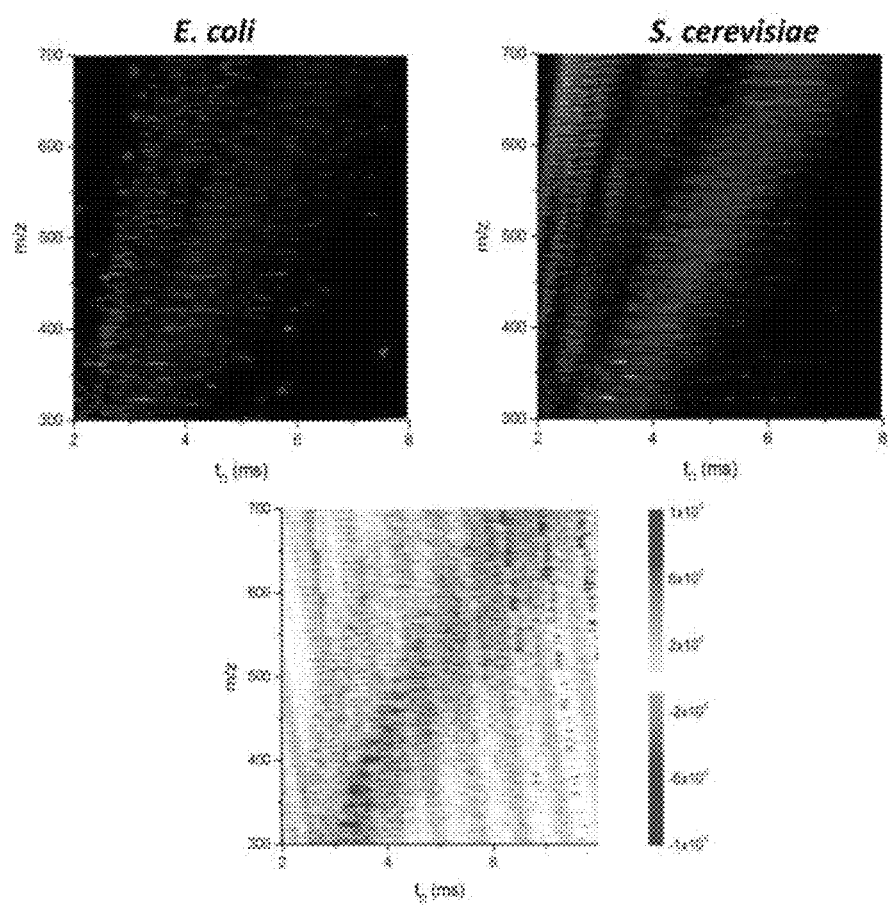
FIG. 12: Shows an exemplary species discrimination from their global mobility profiles. Difference plot was made by subtracting the plot of *S. cerevisiae* from that of *E. coli* by using a spreadsheet. These plots enable easy observations of the differences in modification profiles at the whole cell or tissue level by IMS-MS.
Figure 13:
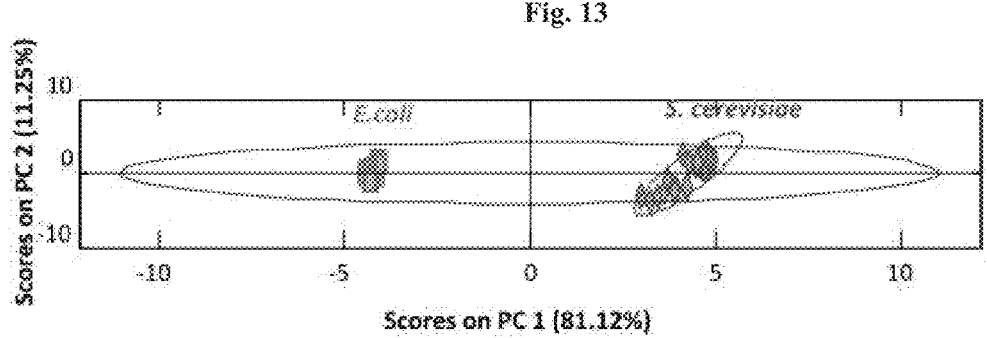
FIG. 13: Shows an exemplary cluster analysis. Principal component analysis of the RNA modifications obtained from 25 sets of *E. coli* and *S. cerevisiae* reveals two distinct populations. Results suggest that microorganisms show distinct RNA modification fingerprints capable of identifying each microorganism

Based on these results, we tested the ability of this method to differentiate different organisms altogether. In one exemplary experiment, direct comparison between profiles afforded by *E. coli* and *S. cerevisiae* grown in the same type of medium lead to the identification of 26 common hits and 10 and 13 unique hits, respectively. Use of this platform has enabled discrimination of varying microorganisms by cellular type as well as metabolic state with a reproducibility of ±1.71% RSD. In one exemplary experiment, maps obtained from *E. coli* and *S. cerevisiae* were compared, 26 modifications were common, whereas 14 and 17 were unique for each. As shown in FIG. 12 a difference plot made by subtracting plot of *S. cerevisiae* from *E. coli* using a script written in house. Cluster analysis confirmed that the two samples had originated from very distinct populations, demonstrating the possibility of obtaining unique fingerprints of RNA modifications based on cell type. FIG. 13 shows a principal component analysis of the RNA modifications obtained from 25 sets of *E. coli* and *S. cerevisiae* that reveals two distinct populations. These results show that microorganisms have distinct RNA modification fingerprints capable of identifying that microorganism.

Interactome analysis is typically supported by genomics and proteomics approaches focused on gene and protein activities. However, cellular components traditionally viewed as products or intermediates of specific pathways can participate in regulatory mechanisms. For example, RNA is involved in protein synthesis and gene regulation and, at the same time, may undergo extensive post-transcriptional modification. This feature provides the opportunity for enzyme-based pathways to feedback at the mRNA level to regulate protein expression.

2. Comparison of Modified RNA Structure Profiles Between Benign and Malignant Samples of Biopsy Tissues.

Thus, comprehensive maps were obtained in similar fashion from human prostate, and benign prostate areas, breast, lung and uterus tissues from different individuals showing tissue-specific features that were reproducible across donors. For an example, see prostate information in FIG. 14A-14E. In fact, cluster maps show distinct differences between benign and malignant samples, FIGS. 14B and 14C. Thus, in one embodiment, a cluster map is derived for identifying a benign sample from a malignant biopsy sample. Further, such cluster maps obtained from mass spectrometry analysis of biopsy samples are contemplated for distinguishing between stages of cancer, see FIG. 14D for an example.

Additionally, a direct comparison between normal and malignant prostate samples revealed at least 13 common modifications with at least 1 and 6 unique modifications, respectively, which indicated the potential for correlations between malignancy and variations of modification biogenesis. Thus, in one embodiment, at least two uniquely modified RNA nucleotides in a prostate biopsy sample, (as compared to a biopsy sample from a normal area of prostate) correlates with the development of a malignant cancer.

3. Comparison of Modified RNA Structure Profiles that are Up-Regulated and/or Down Regulated Between Organisms Having Altered Gene Expression.

Even further, this information indicated that modified RNA molecules might correlate with changes in gene expression pathways involved with the development of cancer cells and tissues. Therefore, the following describes utilizing these types of modification profiles as starting points for identification of corresponding pathways that may be up- or down-regulated. In order to test for malignancy and variations of modification biogenesis associated with changes in PTM profiles, an exemplary gene associated with certain prostate cancers known to cause downstream expression of RNA modifications common to those mapped in the malignant prostate tissue samples was used (FIG. 15), i.e. CCND1 (CLN3 expressed in *S. cerevisiae*) (Refs. 1-3). Thus a knock-down analysis was done for observing changes in PTM. CCND1 has the following characteristics: mRNA and protein are found to overexpressed in certain cell lines: CCND1 causes overexpression of LHP1P, LHP1P co-expresses with TRM1, Pathway 1 is normal expression pathway; dependent on LHP1P, and Pathway 2 can occur in the presence or absence of TRM1. (see, FIG. 16). Thus specific *S. cerevisiae* homologues of knockdowns of the TRM and LHP1 genes associated with these known pathways are being explored to validate the occurrence of these predicted fluxes. Thus, roles of RNA modifications have in cell transformation are contemplated as a tool to monitor the multistage processes that lead from normalcy to malignancy of cells and tissues.

In summary, these methods are contemplated for use in providing results that may be new avenues for use in providing additional diagnostic tools in medicine.
1. Johansson, M. & Bystrom, A.: Dual function of the tRNA(m(5)U54)methyltransferase in tRNA maturation. RNA 8, 324-335 (2002).
2. Copela, L. A., Chakshusmathi, G., Sherrer, R. L., & Wolin, S.A.: The La protein functions redundantly with tRNA modification enzymes to ensure tRNA structural stability. RNA12, 644-654 (2006).
3. Rylova, S. N., Amalfitano, A., et al.: The CLN3 Gene is a Novel Molecular Target for Cancer Drug Discovery. Cancer Research 62, 801-808 (2002).

Example IX

This example relates to using methods of the present inventions for identifying virus-infected cells. The following describes investigating post-transcriptional modifications of host cell RNA and viral RNA by affinity capture and MS analysis. Further, this example relates to RNA viruses, which mutate rapidly and are difficult to control, which pose major health concerns. Therefore, these methods are contemplated to be further useful for analyzing the status of infection of RNA viruses.

The development of effective therapeutic strategies for HIV and other retroviruses is challenging in part because the viral genomic RNA integrates as DNA within the host's genome where it serves as a template for expressing new genomic RNA and viral mRNA. Additional challenges include that established techniques for RNA analysis, such as RT-PCR, use hybridization and amplification procedures that cannot "copy" covalent PTMs present on the original strand. In other words, established techniques for RNA analysis cannot replicate covalent PTMs present in nucleotides expressed by the original RNA nucleotide strand.

In contrast, mass spectrometry is capable of identifying the native PTMs, individually or as part of RNA strands, isolated directly from cells based upon their characteristic mass signature and fragmentation properties. Thus, methods of DNA-probe hybridization were developed and used to capture different types of viral RNAs for mass spectrometric (MS) analysis of post-transcriptional modifications (PTMs). While cellular RNA is extensively decorated with covalent modifications by post-transcriptional processes, little is known about possible modifications of viral RNA before integration or packaging into new infectious particles. Therefore, methods for identifying host genomic RNA, then viral RNA, or combinations thereof, is contemplated to lead to new strategies for selectively targeting viral RNA and thus new therapeutics. Developing an approach based on affinity purification to isolate viral RNA from overwhelming quantities of cellular RNA is contemplated to enable the MS analysis of ribonucleotide modifications at the whole genome level.

Complementary probes were designed during the development of the present inventions that target highly conserved regions of viral RNA, such as their 5'-untranslated region (5'-UTR) to circumvent the possible sequence variability associated with ability of RNA viruses to mutate rapidly. An E. coli strain expressing a 5'UTR of HIV-1, a HeLa cell expressing virus, and a yeast strain containing the virus-like particle (LA virus) was selected as model systems to develop a strategy based on affinity capture by antisense oligodeoxynucleotides (ODNs). Paramagnetic beads were derivatized with ODNs complementary to the infrequently mutating 5'-untranslated region. The amount of beads was scaled up to obtain sufficient amounts of viral RNA, which was estimated to contain 2.6 nmol of ODNs. FIG. 22A-22C and FIG. 23A-23C.

A. Methods.

The development of each step of the proposed workflow was supported by MS determinations performed on a Bruker solariX Fourier transform ion cyclotron resonance (FTICR) mass spectrometer equipped with a 12T superconducting magnet; a Thermo Scientific LTQ-Orbitrap Velos instrument; or a Waters Synapt G2 HDMS ion mobility spectrometry mass spectrometer (IMS-MS). Analyses were accomplished by nanoflow electrospray ionization in negative ion mode. Typical samples were desalted by buffer-exchange against 150 mM ammonium acetate by using Millipore Microcon ultrafiltration devices. Samples were diluted to a final 1-µM concentration and added with 10% isopropanol immediately before analysis. Detection of RNA modifications was carried out by first treating the desired RNA sample with specific nucleases to digest it into individual mononucleotide components.

B. Results.

Initially the utilization of antisense oligonucleotides that were labeled with a biotin group at the 5'-end to enable immobilization onto streptavidin-coated beads. When a test sample was applied to the derivatized beads, followed by salt washes and final thermal elution, the fraction of interest was found to contain both target and antisense oligonucleotides (see, FIG. 30A). These results indicated that the temperature increases employed to dissociate the complex between target and antisense counterpart were also detrimental to the biotin-streptavidin interaction and induced unwanted deterioration of the affinity medium. As possible alternatives, we tested the utilization of 5'-thio-oligonucleotides to be linked by iminothiolane reaction to amine-coated beads, or by direct formation of disulfide bonds with sulfhydryl surfaces. The former produced low derivatization yields, whereas the latter provided affinity media with acceptable capacity. When these types of beads were tested, the elution fraction contained the desired target (FIG. 30B).

Figure 17:
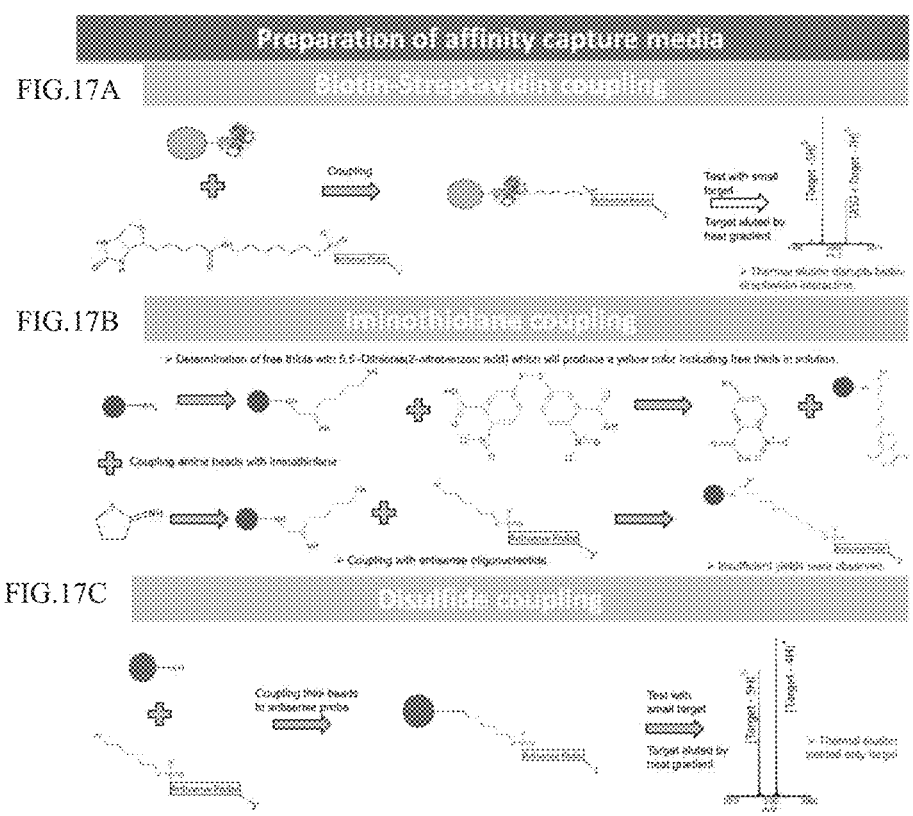
FIG. 17A-17C. Shows an exemplary preparation of affinity capture media: 17A. Biotin-Streptavidin coupling. 17B. Iminothiolane coupling. 17C. Disulfide coupling; including problems associated with each in the lower right of each method.

During the development of the present inventions the following steps were taken in order to determine a method for affinity capture RNA for MS analysis: a) Test different strategies to prepare affinity capture media based on specific target-antisense interactions; b) Develop strategies to guide the selection of antisense oligonucleotides with the ability to capture viral RNA in total cell lysates; c) Evaluate different technologies to verify the purity of captured genomic RNA; d) Apply the above approaches to perform actual analysis of RNA modifications in viral RNA. Several examples of affinity capture media are shown in FIG. 17A-17C, in particular, Biotin-Streptavidin, Iminothiolane, and disulfide coupling, along with undesirable results where thermal elution disrupts biotin-streptavidin interactions, insufficient yields were observed and thermal elution yielded target, respectively. Thus, problems with each of these methods led to the development of methods described herein for probe selection and using fluorescent labeling and magnetic beads as capture media. Additionally, these experiments were done in yeast, bacteria and human HeLa cells.

Figure 18:
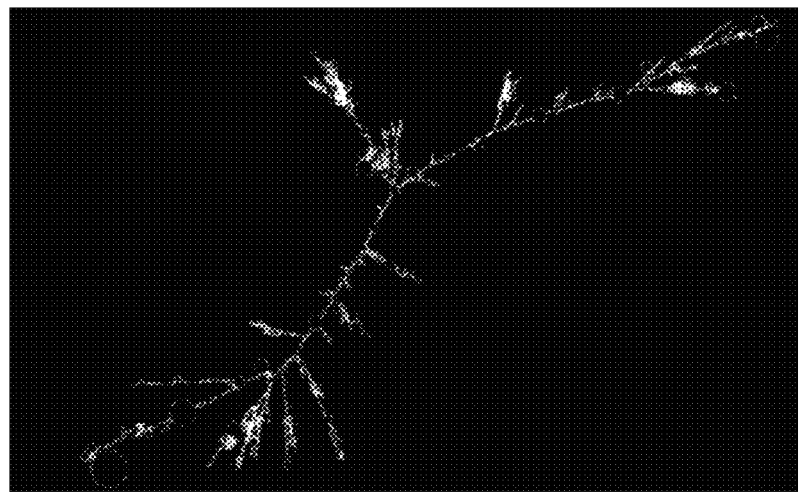
FIG. 18. Shows an exemplary sFold analysis that predicts likely secondary structures based on thermodynamic considerations.
Figure 19:
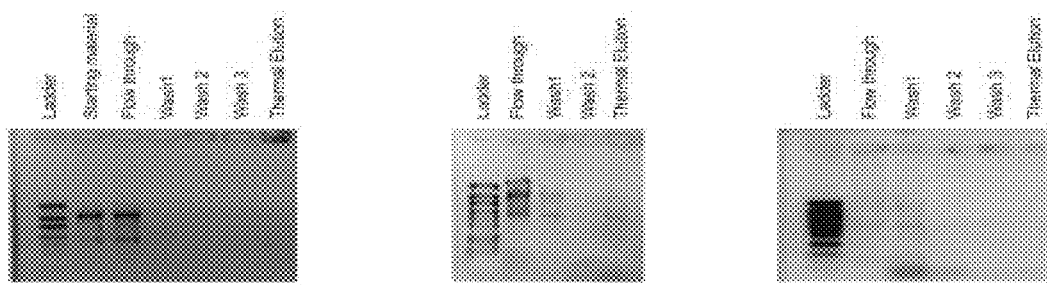
FIG. 19. Shows an exemplary gel electrophoresis to monitor the lack of success of a few probes selected for capturing a viral genome based upon computational selection.
Figure 20A:
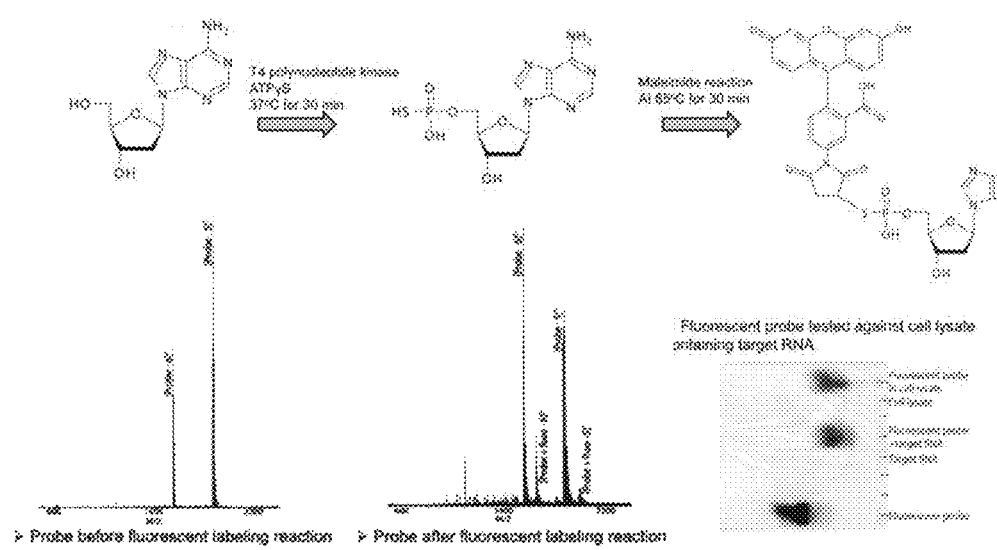
FIG. 20A-20B. Shows an exemplary analysis strategy, developed and tested for use in the methods described herein, to guide probe selection, based on the binding of fluorescent-labeled probes to the substrate of interest, i.e. target RNA. 20A. T4 polynucleotide kinase reaction subsequent to a fluorescent labeling reaction. The structure at the far right shows a probe after fluorescent labeling reaction 20B. An example of a fluorescent probe of the present inventions tested against cell lysate containing target RNA showing results of modified RNA structures at the far right.

Therefore, appropriately designed sets of affinity media were then employed to purify genomic RNA from isolated HIV-1 virions, poliovirus, hepatitis C virus, and S. cerevisiae L-A virus. These experiments afforded mixed results that highlighted the challenge of identifying the best possible regions of viral RNA to be targeted by the capture interactions. Computational tools that consider the presence of possible secondary structures and the putative stability of antisense annealing are typically employed to guide the selection process. For example, sfolds, see FIG. 18 and Table E, in addition to the unsuccessful results of a few probes selected for initial testing based chosen by computational methods, FIG. 19. Therefore, these algorithms cannot account for higher-order structure or bound proteins, which may prevent the capture interactions, FIG. 19. For this reason, we explored the application of fluorescent-labeled oligonucleotides to evaluate their actual ability to anneal with viral RNA in complex lysates, FIG. 20A. MS analysis was employed to optimize the conditions of the labeling reaction (FIG. 31), which were then employed to derivatize series of putative capture constructs. The addition of labeled probes to viral lysates was followed by nucleic acid extraction and gel electrophoresis to highlight stable binding. Initial results have already shown considerable success in identifying viable capture sequences.

1. *E. coli* Expressing Virus.

Figures 21A, 21B, 21C:
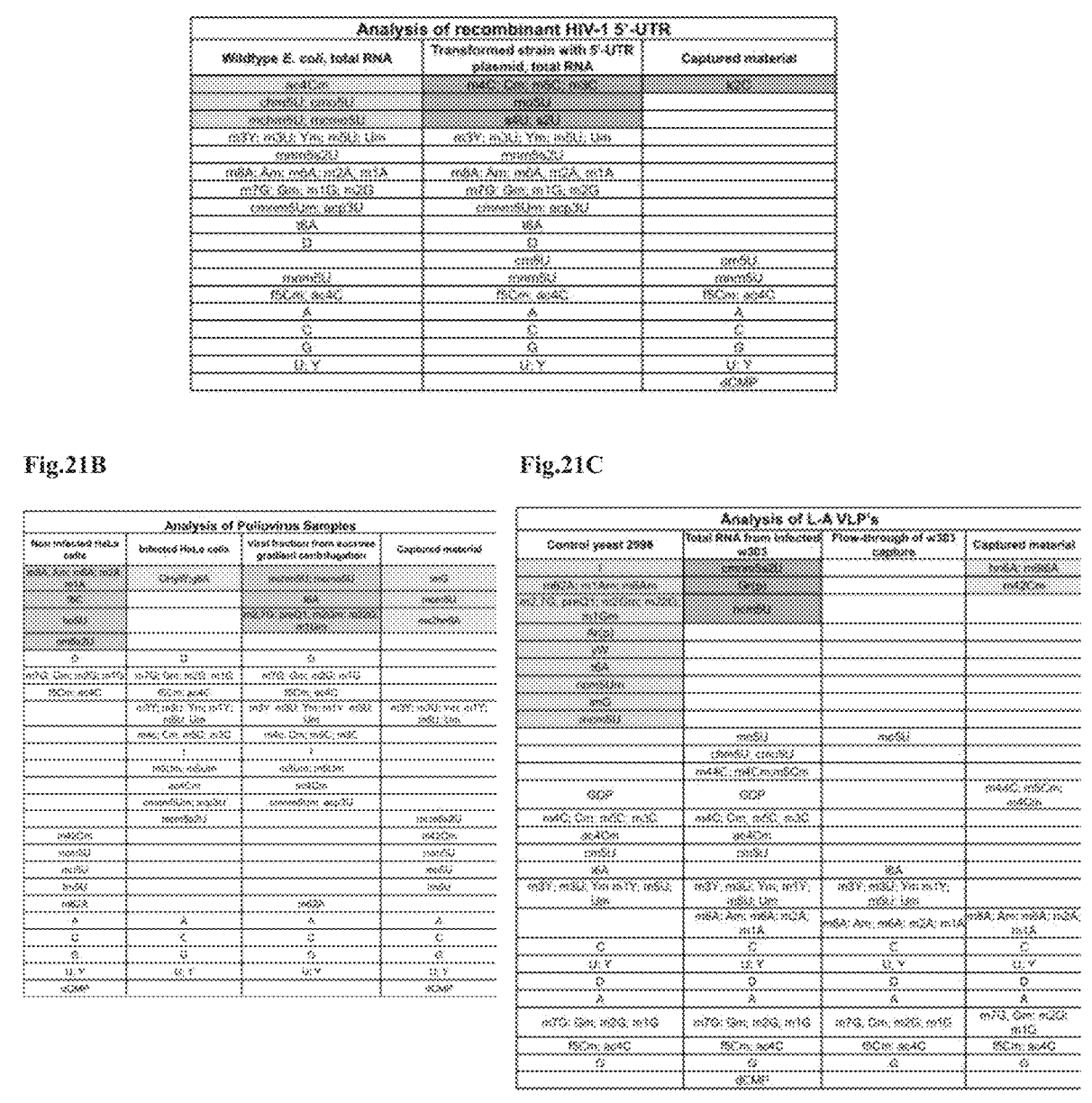

Similar methods were used for isolating RNA structures from *E. coli* expressing virus, (i.e. a recombinant HIV-1 5'UTR). FIG. 21A.

In addition to the results shown in FIG. 21A-21C, it was found that different modifications are present in *E. coli* total RNA with and without the 5'-UTR HIV-1 plasmid; the expressed 5'-UTR purified from the transformed strain contained a unique modification that was absent in wildtype; total RNA extracted from uninfected hosts and infected cells showed distinct modifications patterns (profiles); captured material contained unique modifications that differed from those detected in the corresponding total lysates; and affinity capture increased the ability to observe low-abundance modifications in viral RNA.

2. HeLa Cells and Virus Expressing HeLa Cells.

Additionally (and concurrently with viral RNA studies described herein), studies were performed on HeLa cells to examine RNA modification content in total RNA versus isolated mRNA. Isolation of mRNA was performed using affinity capture techniques designed to target the poly A tail found common in mRNA species, see an exemplary overview of this method in FIG. 22B. The success of the capture was confirmed using gel electrophoresis and reverse transcription polymerase chain reaction. The total RNA and isolated mRNA were then subjected to the same digestion and mapping as described herein. Global profiles revealed hits in total RNA and isolated mRNA. This information is contemplated for determining the applicability of this strategy to map modifications in rRNA and tRNA.

Therefore, these approaches were further applied to HeLa cells to initially compare modification content in total RNA versus isolated mRNA. The latter was isolated from the initial material by affinity capture techniques targeting the poly-A tail common to mRNA molecules. Gel electrophoresis and reverse transcription polymerase chain reaction (RT-PCR) were applied to assess the success of the capture. Hits observed by searching data obtained from HeLa cells isolated mRNA against the non-redundant database generated in house (i.e. at the University of Albany by combining data from the RNA Modifications and Modomics Databases). FIG. 29. Profiles revealed a total of 90 and 42 putative hits in total RNA and isolated mRNA respectively.

Profiles of virally infected cells were compared to uninfected cells, see, FIG. 21B. As shown in the figure, several PTM RNA structures either appeared or disappeared while other remained the same.

Thus, MS approaches allow for quantification of RNA modifications in both total RNA and isolated mRNA.

1. Rose, R. E., Giza, J., Fabris, D. Comprehensive ribonucleotide modification maps as possible tracking tools for the multistage processes involved in cell transformation from normalcy to malignancy (*ASMS*, 2014).

3. Yeast Expressing Virus.

Therefore in order to begin determining whether MS analysis of ribonucleotide modifications at the whole genome level would provide information on targeting viral RNA, total RNA from *S. cerevisiae* (2 strains) was isolated using a classic phenol/chloroform extraction and digested to mononucleotides using a cocktail of specific nucleases.

a. *S. cerevisiae* w303 Strain.

Figure 20B:
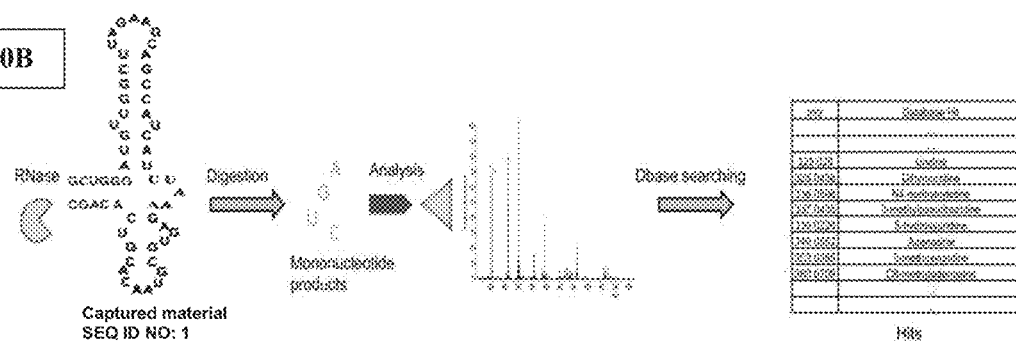

An additional capture method, using the w303 yeast strain containing the LA virus as a model system, a strategy to isolate viral RNA was developed based on the hybridization of antisense DNA probes immobilized on magnetic beads. Paramagnetic beads were derivatized with antisense oligodeoxynucleotides (ODNs) to target viral RNA within the total RNA of w303. The region targeted by the ODNs was the infrequently mutating 5' untranslated region of the LA virus. This region is known to be conserved, making it ideal within a sequence of highly mutable ribonucleotides. A capture system prepared as described above was then employed to isolate the RNA of L-A virus-like-particles (VLP's) from total lysates of w303 yeast. In this case, both MS and gel electrophoresis were employed to analyze the elution fraction for the possible presence of extraneous RNA species. Upon digestion with ribonucleases, MS analysis revealed the presence of up to 23 RNA modifications that were assigned with the aid of database searching. FIG. 20B.

Analysis of LA virus RNA revealed the presence of nine PTMs which have a modification that was not previously reported on this RNA. In comparison, analogous analysis total RNA extracts from non-infected yeast displayed up to 40 modifications. Of these, 12 hits were in common with those observed in the L-A VLP's, thus supporting the hypothesis that viral RNA may be differentially modified. Through MS analysis, 30 PTMs were identified on isolated viral RNA, none of which were reported for this RNA. A total of 72 PTMs were observed on the total RNA of the w303 yeast strain as compared to uninfected yeast strains.

Surprisingly, the same types of PTMs were detected in total RNA obtained from yeast strain BY4741 not containing LA virus and capable of expressing up to 41 PTMs'. This observation is consistent with the fact that enzymes responsible for PTM biogenesis are not necessarily viral proteins, but are instead encoded by host yeast genome.

1. Reyes-Darias, J., Sánchez-Luque, F., & Berzal-Herranz, A. (2012). HIV RNA dimerisation interference by antisense oligonucleotides targeted to the 5' UTR structural elements. Virus Research, 169(1), 63-71. Retrieved Oct. 21, 2014.

2. Icho, Tateo, and Reed B. Widmer. "The Double-stranded RNA Genome of Yeast Virus L-A Encodes Its Own Putative RNA Polymerase by Fusing Two Open Reading Frame." The Journal of Biological Chemistry264.April 25 (1989): 6716-723. Web.

3. Rose, R. E., Giza, J., Fabris, D. Comprehensive ribonucleotide modification maps as possible tracking tools for the multistage processes involved in cell transformation from normalcy to malignancy. (ASMS, 2014).

b. *S. cerevisiae* BY4741 Strain.

Uninfected yeast strain BY4741 has been shown to express up to 40 PTMs[1], some of which were also observed in the w303 yeast strain, as well as isolated viral RNA. This observation is consistent with the fact that enzymes producing PTMs may not be solely encoded by the virus, but also by the host yeast genome.

1. Quinn, R., Basanta-Sanchez, M., Rose, R. E. & Fabris, D.: Direct infusion analysis of nucleotide mixtures of very similar or identical elemental composition. J. Mass Spectrom. 48, 703-12 (2013).
2. Holmberg, A., Blomstergren, A., Nord, O., Lukacs, M., Lundeberg, J., Uhlen, M.: The biotin-streptavidin interaction can be reversibly broken using water at elevated temperatures. Electrophoresis 26, 501.510 (2005).
3. Bischoff, R., Coull, J. M., Regnier, F. E.: Introduction of 5'-Terminal Functional Groups into Synthetic Oligonucleotides for Selective Immobilization. Analytical Biochem. 164, 336-344 (187).

Example X

This Example Describes the Epitranscriptomics of Long Noncoding (Lnc)RNAs in *S. cerevisiae*, i.e. Changes in PTM RNA Structures Related to a Change in Growth Conditions and/or Gene Expression.

Ribonucleic acids (RNA) are involved in a variety of regulatory processes that allow for functions of biological systems. RNA is related to gene expression such that certain RNA modifications have been found to be over or under expressed in cancerous tissues, making these modifications target for potential biomarkers (Koshida et al. 2011) in addition to their use in profiling a disease state. These modifications can be detected using MS and IMS-MS approaches that allow for the identification and differentiation of different isobaric species of RNA modifications.

A. Introduction.

Exposure of cells to external stimuli results in immediate adaptation through new regulatory responses affecting cellular memory to maximize survival or death. These responses result in wide ranges of anomalies caused by epigenetic events which have historically been characterized by DNA methylations, histone modifications and/or activities involving long noncoding ribonucleic acids (lncRNAs). It is now apparent that several RNA species are post-transcriptionally modified and, are responsible for structural and functional roles within the cell. For this reason, methods were developed using mass spectrometry to globally profile these RNA modifications in *S. cerevisiae* including to investigate the role of lncRNAs; known to cause disruption of early transcriptional processes, to discover relationships between known epigenetic events and related RNA processing pathways. In particular, *S. cerevisiae* were grown under different conditions, including under salt conditions for inducing hog1 expression, FIG. 26, in order to determine specific changes in modified RNA structures.

B. Methods.

*S. cerevisiae* strains were grown in-house in either YPD (i.e. rich medium) or SC (synthetic complete) media at 30° C. and 37° C. Where applicable, strains were either induced with 0.4M NaCl or exposed to UV irradiation for 15 min. Total RNA was obtained by phenol-chloroform extraction. Extracts were hydrolyzed to mononucleotide mixtures by digestion with specific nucleases. Sample solutions were diluted to final concentrations of ~3 μM total ribonucleotides in 150 mM ammonium acetate and 10% 2-propanol. Hydrolyzed ribonucleotide mixtures from whole-cell extracts were used in order to enable both characterization and quantification of all PTMs in the transcriptome. This approach involves initial assignment by database searching, followed by structure confirmation supported by gas-phase fragmentation data.

Figure 27:
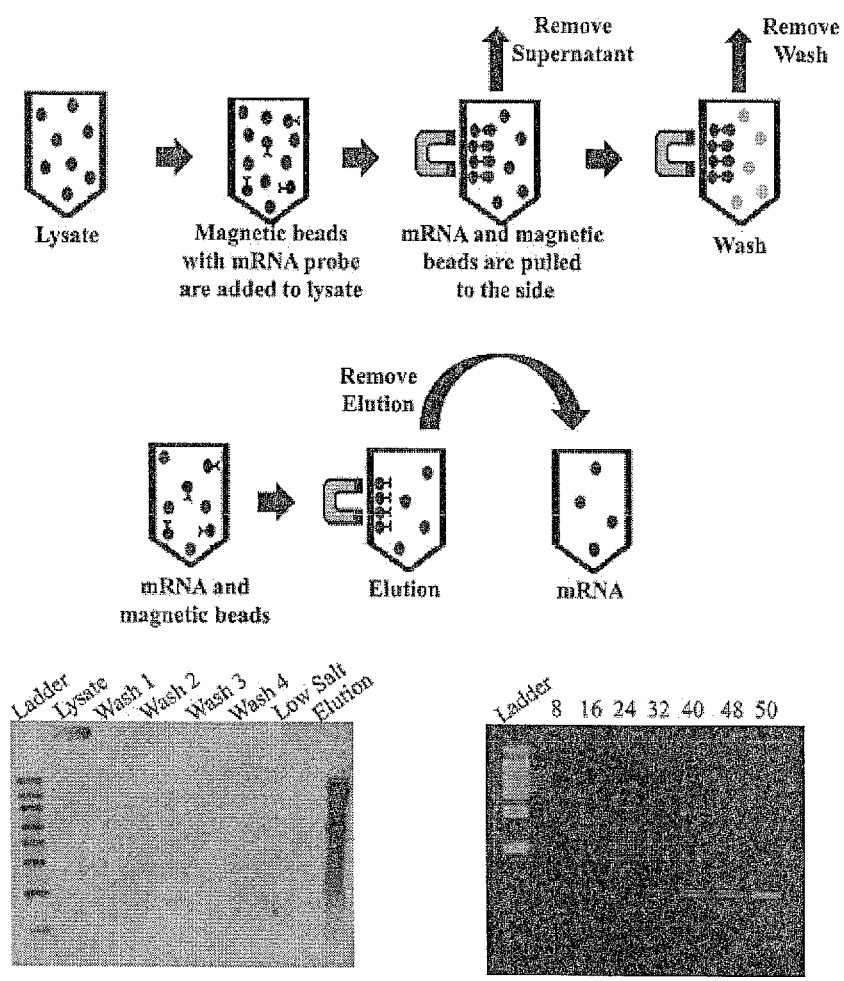
FIG. 27. Shows an exemplary location of lncRNAs in sample fractions using sequence-specific captures, also to confirm quantity.

Direct infusion nanospray analyses were performed either on a Thermo Scientific LTQ-Orbitrap Velos or a Waters Synapt G2 HDMS mass spectrometer. High-resolution determinations and MS$^n$ analyses were completed on the former utilizing automated procedures developed in-house. Ion mobility determinations and fragmentation were completed on the latter. Data interpretation employed OriginPro software. See exemplary methods, FIG. 27.

C. Preliminary Data.

*S. cerevisiae* were grown under different conditions including high salt to induce expression of at least one different gene, then analyzed for differences in modified PTM RNA structures.

1. *S. cerevisiae* were Grown Under Different Media Conditions.

Figure 28:
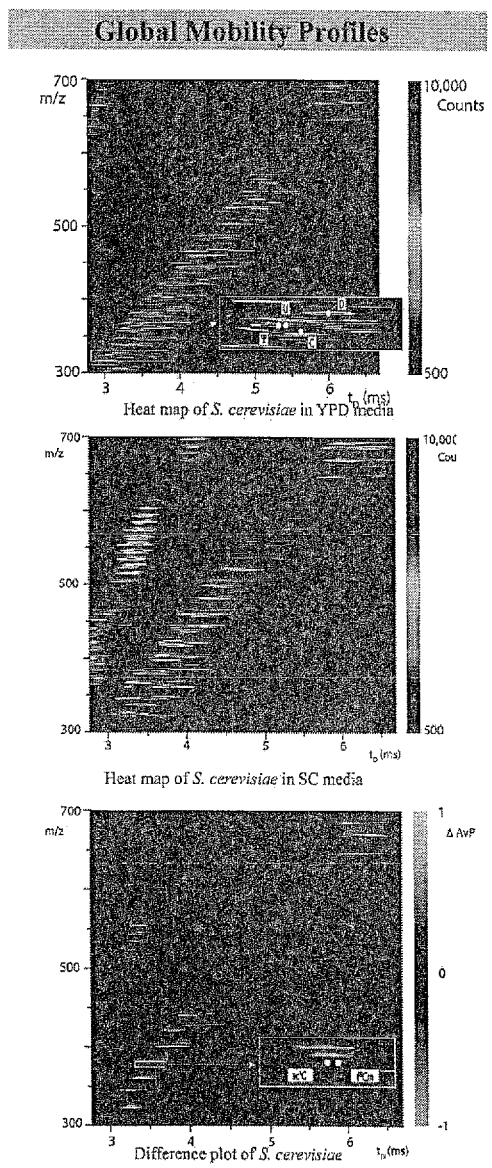
FIG. 28. Shows an exemplary global mobility profiles of isolated PTM RNA structural modifications.

High-resolution mass spectrometry and ion mobility spectrometry-mass spectrometry approaches have enabled detection of 40 ribonucleotide (PTM) modifications in whole-cell lysates of *S. cerevisiae* strain BY4741 (WT) with a biological reproducibility of ±7.8% relative standard deviation in rich media. At least eight of these structures were previously unreported for this microorganism. To assess the feasibility of the platform to monitor changes in growth conditions, *S. cerevisiae* was also grown in stringent media. In this case, a total of 49 modifications were detected whereas 8 were unique. Of the 41 common hits whose abundance swung outside the accepted biological deviation, 28 were overexpressed and 3 underexpressed in stringent media proving the ability to monitor and quantify single modification fluxes. 13 of the common PTMs that were previously unreported for this microorganism was likely due to the attention paid in the past to rRNA and tRNA analysis, whereas the comprehensive nature of this approach captured any type of PTM present in the total RNA extract. Therefore, this method identified additional PTM RNA structures over previous methods. FIG. 28.

2. *S. cerevisiae* Induced to Express Hog1.

In similar fashion, global surveys were examined to investigate correlations between epigenetic mechanisms governed by external stimuli and regulatory events involving lncRNAs. When samples of *S. cerevisiae* treated with high salt were analyzed, we found unique PTMs absent in untreated cells, as well as others that were up-/down-regulated. We identified PTMs whose induction, like that of a discrete set of ~200 long non-coding RNAs (lncRNAs), is dependent on the stress-activated protein kinase Hog1, thus suggesting that PTMs may be involved in the activity of different classes of RNAs.

Specifically, WT *S. cerevisiae* was treated with NaCl to induce the expression of hog1, FIG. 26; a stress-activated protein kinase which controls the cell cycle, gene expression, and mRNA biogenesis, resulting in overexpression of lncRNAs involved in chromatin remodeling. Profiles revealed the overexpression of 10 PTM RNA structures and occurrence of eight unique modifications confirming that particular RNA species are overexpressed during induction. In the absence of hog1 (hog1D), profiles showed the underexpression and disappearance of 24 and 7 PTM RNA structure modifications, respectively; further supporting this finding. Both WT and hog1 D mutants have also been investigated under various growth temperatures and exposure to UV irradiation. For instance, when WT growths at 30° C. and 37° C. were compared, vast depletions of modification content was detected at elevated temperatures; 16 PTM RNA structure modifications disappeared with 17 drastically underexpressed (19-136% abundance deviation).

TABLE A

*E. coli* RNA structures "hits" obtained by searching raw data against an in house database (at the U Albany by combining data from the RNA Modifications and Modomics Databases) database.

| Experimental mass (Da) | Monoisotopic mass (Da) | Hit |
|---|---|---|
| 323.05210 | 323.05185 | C‡ |
| 324.03600 | 324.03587 | Y‡, U‡ |
| 326.05129 | 326.05152 | D‡ |
| 338.05163 | 338.05152 | m3Y, Um‡, m5U, m1Y, Ym‡, m3U |
| 347.06299 | 347.06308 | A‡ |
| 348.04709 | 348.04710 | I‡ |
| 351.08301 | 351.04677 | m5Cm, m4Cm, m44C‡* |
| 363.05768 | 363.05800 | G‡ |

TABLE A-continued

*E. coli* RNA structures "hits" obtained by searching raw data against an in house database (at the U Albany by combining data from the RNA Modifications and Modomics Databases) database.

| Experimental mass (Da) | Monoisotopic mass (Da) | Hit |
|---|---|---|
| 365.06245 | 365.06242 | ac4C‡*, f5Cm‡* |
| 367.07800 | 367.07807 | mnm5U‡ |
| 375.09455 | 375.09438 | m6Am, m1Am, m62A‡ |
| 377.07342 | 377.07365 | m1G‡, m2G‡, m7G‡, Gm‡ |
| 379.07777 | 379.07807 | ac4Cm‡ |
| 398.03611 | 398.03626 | cmo5U, chm5U |
| 411.06762 | 411.06789 | cmnm5U‡ |
| 425.08330 | 425.08354 | acp3U‡, cmnm5Um‡ |
| 489.12579 | 489.12608 | Q‡ |
| 492.10031 | 492.10059 | t6A‡ |
| 506.11613 | 506.11624 | m6t6A, hn6A |

‡Assignments corroborated by tandem MS determinations
*Modifications that were not previously detected in *E. coli*

TABLE AA

*E. coli* RNA structures. X represents a structure not found in the referenced databases.

| Hit | Names (common) | Structure(s), respectively |
|---|---|---|
| C‡ | cytidine | (structure) |
| Y‡, U‡ | Pseudouridine, uridine | (structures) |
| D‡ | dihydrouridine | (structure) |

TABLE AA-continued

*E. coli* RNA structures. X represents a structure not found in the referenced databases.

| Hit | Names (common) | Structure(s), respectively |
|---|---|---|
| m³Y, Um‡, m⁵U, m¹Y, Ym‡, m³U | 3-methylpseudouridine, 2'-O-methyluridine, 5-methyluridine, 1-methylpseudouridine, 2'-O-methylpseudouridine, 3-methyluridine | |
| A‡ | adenosine | |
| I‡ | inosine | |

TABLE AA-continued

*E. coli* RNA structures. X represents a structure not found in the referenced databases.

| Hit | Names (common) | Structure(s), respectively |
|---|---|---|
| m⁵Cm, m⁴Cm, M⁴₄C‡* | 5,2'-O-dimethylcytidine, N⁴,2'-O-dimethylcytidine, N⁴,N⁴-dimethylcytidine | |
| G‡ | guanosine | |
| ac⁴C‡*, f⁵Cm‡* | N⁴-acetylcytidine, 5-formyl-2'-O-methylcytidine | |
| mnm⁵U‡ | 5-methylaminomethyluridine | |

TABLE AA-continued

*E. coli* RNA structures. X represents a structure not found in the referenced databases.

| Hit | Names (common) | Structure(s), respectively |
|---|---|---|
| m⁶Am, m¹Am, M⁶₄A‡ | N⁶,2'-O-dimethyladenosine, 1,2'-O-dimethyladenosine, N⁶,N⁶-dimethyladenosine | 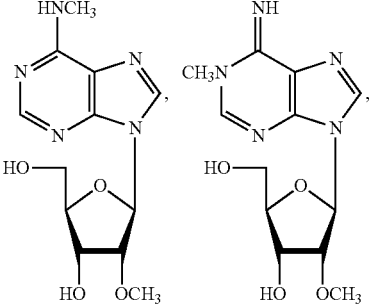 |
| m¹G‡, m²G‡, m⁷G‡, Gm‡ | 1-methylguanosine, N²-methylguanosine, 7-methylguanosine, 2'-O-methylguanosine | 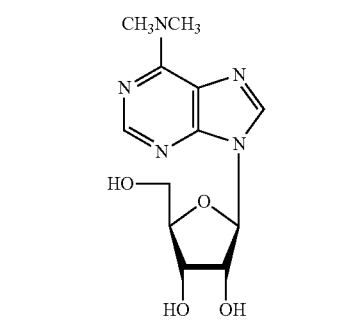 |
| ac⁴Cm‡ | N⁴-acetyl-2'-O-methylcytidine | 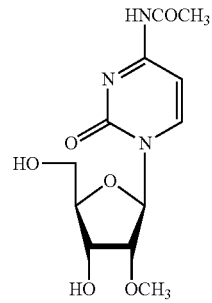 |

TABLE AA-continued
*E. coli* RNA structures. X represents a structure not found in the referenced databases.
| Hit | Names (common) | Structure(s), respectively |
|---|---|---|
| cmo⁵U, chm5U | uridine 5-oxyacetic acid, 5-(carboxyhydroxymethyl)uridine | 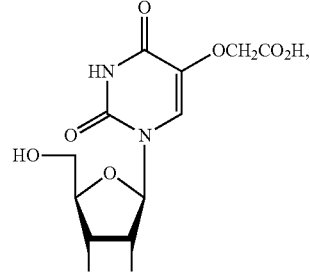 |
| cmnm⁵U‡ | 5-carboxymethylaminomethyluridine | 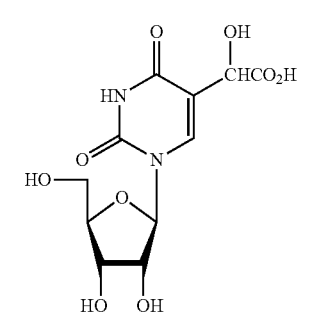 |
| acp³U‡, cmnm⁵Um‡ | 3-(3-amino-3-carboxypropyl)Uridine, 5-carboxymethylaminomethyl-2'-O-methyluridine | 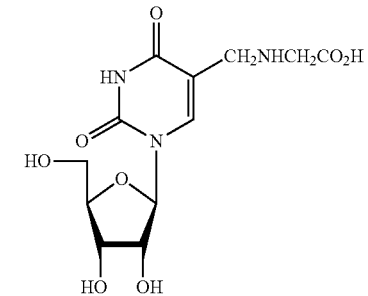 |

TABLE AA-continued

*E. coli* RNA structures. X represents a structure not found in the referenced databases.

| Hit | Names (common) | Structure(s), respectively |
|---|---|---|
| Q[‡] | queuosine | 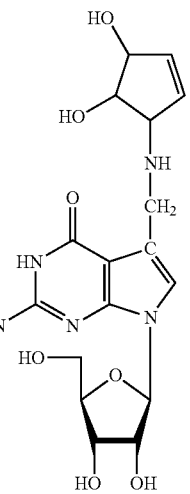 |
| t6A[‡] | N6-threonylcarbamoyladenosine | 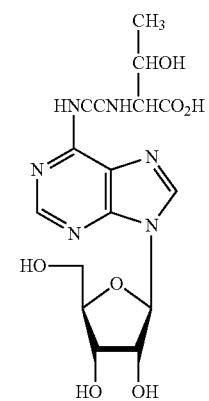 |
| m6t6A, hn6A[‡] | N6-methyl-N6-threonylcarbamoyladenosine, N6-hydroxynorvalylcarbamoyladenosine | 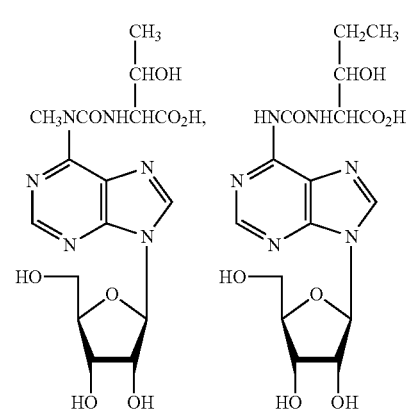 |

[‡]Assignments corroborated by tandem MS determinations

*Modifications that were not previously detected in *E. coli*

TABLE B

Summary of RNA modification analysis in total RNA extract from *E. coli*. Exemplary structures (also termed "Figures") of merit associated with this analysis: LOD and Signal Response.

| Name | Monoisotopic mass (Da) | Equivalent per mole | Detection limit (mol) | Response (m, q) | Theoretical AvP (%) | Experimental AvP (%) |
|---|---|---|---|---|---|---|
| C | 322.0441 | 15 | $3.44 \times 10^{-17}$ | $1.6 \times 10^{11}$, $5.0 \times 10^{0}$ | 24.5 | 24.5 |
| U/Ψ | 323.0279 | 14 | $2.68 \times 10^{-17}$ | $1.5 \times 10^{11}$, $2.0 \times 10^{1}$ | 21.9 | 21.9 |
| D | 325.0437 | 2 | $1.80 \times 10^{-17}$ | $1.8 \times 10^{11}$, $3.0 \times 10^{1}$ | 3.6 | 3.5 |
| m3C, m5C, Cm | 336.0597 | 3 | $5.50 \times 10^{-17}$ | $1.4 \times 10^{11}$, $8.0 \times 10^{1}$ | 4.3 | 4.3 |
| A | 346.0552 | 17 | $9.58 \times 10^{-17}$ | $1.3 \times 10^{11}$, $9.2 \times 10^{0}$ | 23.2 | 23.1 |
| m1A | 360.0709 | 1 | $9.29 \times 10^{-17}$ | $3.5 \times 10^{10}$, $3.0 \times 10^{1}$ | 1.1 | 0.9 |
| G | 362.0501 | 18 | $1.55 \times 10^{-17}$ | $1.7 \times 10^{11}$, $3.7 \times 10^{1}$ | 30.4 | 30.5 |
| m2G, Gm | 376.0658 | 3 | $5.29 \times 10^{-18}$ | $1.2 \times 10^{11}$, $5.8 \times 10^{1}$ | 3.6 | 3.4 |
| m22G | 390.0813 | 1 | $2.44 \times 10^{-17}$ | $1.7 \times 10^{11}$, $2.0 \times 10^{1}$ | 1.7 | 1.6 |
| yW | 587.1501 | 1 | $4.14 \times 10^{-17}$ | $1.1 \times 10^{11}$, $1.7 \times 10^{1}$ | 1.1 | 1.0 |

*Recovery of tRNA phe monitored by UV absorption was ~25%
*LOD obtained by calculating moles of each NMP which provided at least a 3:1 S/N at a consumption of ~0.093 µL.
*Response was calculated by plotting signal average against concentration to obtain curves with m in counts/M and q in counts
*AvP was calculated by dividing intensity by the sum of the intensities of the canonical NMPs
*Experimental AvP calculated directly from the ESI-MS data
*Theoretical AvP obtained from the intensity of exactly 1M of tRNA Phe and calculated by substituting equivalents per mole into the response curve.

TABLE C

Absolute Quantification.

| Name | Monoisotopic mass (Da) | Concentration (M) | Amount (mol/g) | Experimental AvP (%) |
|---|---|---|---|---|
| C | 323.05185 | $2.12 \times 10^{-7}$ | $1.33 \times 10^{-9}$ | 26.88 |
| Y, U | 324.03587 | $1.66 \times 10^{-7}$ | $1.04 \times 10^{-9}$ | 19.45 |
| D | 326.05152 | $1.16 \times 10^{-8}$ | $7.28 \times 10^{-11}$ | 1.68 |
| m3Y, Um, m5U, m1Y, Ym, m3U | 338.05152 | — | — | 1.05 |
| A | 347.06308 | $2.14 \times 10^{-7}$ | $1.34 \times 10^{-9}$ | 21.69 |
| I | 348.04710 | — | — | 0.04 |
| m5Cm, m4Cm, m44C | 351.08315 | — | — | 0.03 |
| G | 363.05800 | $2.27 \times 10^{-7}$ | $1.42 \times 10^{-9}$ | 31.98 |
| ac4C, f5Cm | 365.06242 | — | — | 0.52 |
| mnm5U | 367.07807 | — | — | 0.28 |
| m6Am, m1Am, m62A | 375.09438 | — | — | 0.02 |
| m1G, m2G, m7G, Gm | 377.07365 | $1.06 \times 10^{-8}$ | $6.64 \times 10^{-11}$ | 0.95 |
| ac4Cm | 379.07807 | — | — | 0.04 |
| cmo5U, chm5U | 398.03626 | — | — | 0.16 |
| cmnm5U | 411.06789 | — | — | 0.01 |
| acp3U, cmnm5Um | 425.08354 | — | — | 0.16 |
| Q | 489.12608 | — | — | 0.66 |
| t6A | 492.10059 | — | — | 0.59 |
| m6t6A, hn6A | 506.11624 | — | — | 0.09 |

*Determination of NMPs present in total RNA extract from *E. coli*.
*The addition of accurately known amounts of *S. cerevisiae* tRNA Phe enabled an absolute quantitative determination by following the method of the standard additions

TABLE D

Reproducibility.

Canonical Bases (% RSD)

| | *E. Coli* | | | *S. cerevisiae* | |
|---|---|---|---|---|---|
| | LB | SC | GMM | YPD | SC |
| Tech | ±2.65 | ±2.59 | ±2.37 | ±3.38 | ±2.64 |
| Bio | ±3.29 | ±6.28 | ±3.40 | ±3.26 | ±2.83 |

Total Modifications (% RSD)

| | *E. coli* | | | *S. cerevisiae* | |
|---|---|---|---|---|---|
| | LB | SC | GMM | YPD | SC |
| Tech | ±9.44 | ±3.58 | ±8.47 | ±4.99 | ±9.82 |
| Bio | ±22.2 | ±22.46 | ±16.8 | ±5.53 | ±13.08 |

*Technical reproducibility: five repeat analysis of the same biological sample.
* Biological reproducibility: five separate biological samples (i.e., different growths).
*Reproducibility was monitored across varying microorganisms and media to fully assess the capabilities of the platform.

TABLE E

Computational tools such as sFold produce tens of thousands of hits. Filtering possible targets by GC content, sequence length, and binding energy provided >1,000 viable probes for the 5'-UTR of poliovirus.

| | Sequence position | Target sequence | Antisense probe | GC content | binding energy (kcal/mol) |
|---|---|---|---|---|---|
| | . . . | . . . | . . . | . . . | . . . |
| | . . . | . . . | . . . | . . . | . . . |
| SEQ ID NOS: 2, 3 | 108-132 | AGACGCACAAAACCAAGUUCAAUAG | CTATTGAACTTGGTTTTGTGCGTCT | 40.00% | -16.2 |
| SEQ ID NOS: 4, 5 | 109-133 | GACGCACAAAACCAAGUUCAAUAGA | TCTATTGAACTTGGTTTTGTGCGTC | 40.00% | -15.5 |
| SEQ ID NOS: 6, 7 | 105-129 | CUUAGACGCACAAAACCAAGUUCAA | TTGAACTTGGTTTTGTGCGTCTAAG | 40.00% | -14.9 |
| SEQ ID NOS: 8, 9 | 101-125 | GUAACUUAGACGCACAAAACCAAGU | ACTTGGTTTTGTGCGTCTAAGTTAC | 40.00% | -14.2 |
| SEQ ID NOS: 10, 11 | 104-128 | ACUUAGACGCACAAAACCAAGUUCA | TGAACTTGGTTTTGTGCGTCTAAGT | 40.00% | -14.2 |
| SEQ ID NOS: 12, 13 | 103-127 | AACUUAGACGCACAAAACCAAGUUC | GAACTTGGTTTTGTGCGTCTAAGTT | 40.00% | -13.7 |
| SEQ ID NOS: 14, 15 | 102-121 | UAACUUAGACGCACAAAACC | GGTTTTGTGCGTCTAAGTTA | 40.00% | -13.6 |
| | . . . | . . . | . . . | . . . | . . . |
| | . . . | . . . | . . . | . . . | . . . |

TABLE F

W303 strain of *S. cerevisiae* with LA virus.

| Mono-isotopic mass (Da) | Modification | BY4741 | Total RNA (w303) | Captured RNA |
|---|---|---|---|---|
| 323.0518509 | C | 28.6897 | 17.10844703 | 14.3068139 |
| 324.0358664 | Y, U | 22.0071 | 22.68117951 | 16.4082196 |
| 326.0515165 | D | 2.95185 | 0.242827734 | 0.03969875 |
| 337.0675009 | m3C, m5c, Cm m4C | 0.24501 | 0.04172404 | 0.02371869 |
| 338.0515165 | Um, m5U, m1Y, Ym, m3U, m3Y | 1.03044 | 0.70030307 | 0.14116665 |
| 340.0307811 | hoSU | | 1.861016805 | |
| 340.0671666 | m5D | | 0.199075464 | |
| 347.0630843 | A | 21.6258 | 26.98758691 | 42.3932503 |
| 348.0470998 | I | 0.14405 | 0.074473048 | |
| 351.0467655 | f5C | | 0.025845435 | |
| 351.083151 | m5Cm, m4Cm, m44C | | 0.017545894 | 0.01631697 |
| 352.0307811 | f5U | | 1.52901622 | |
| 353.0624155 | hm5C, nm5U, s2Um | | 0.07431334 | 0.0278083 |
| 354.0464311 | mo5U | | 0.465418505 | |
| 361.0787343 | m1A, m2A, A, Am, m8Am | 0.10186 | 0.086536289 | |
| 362.0627499 | m1I, Im | | 0.009356357 | |
| 363.0579989 | G | 27.6773 | 33.22278654 | 26.8917161 |
| 364.0420145 | X | | 0.079187778 | |
| 365.0624155 | ac4C, f5Cm | 0.47447 | 0.563964615 | 0.37881489 |
| 366.0464311 | f5Um | | 0.040026878 | |
| 367.0780656 | mnm5U | | 0.064362474 | |
| 369.0395716 | nm5s2U | | 0.011154386 | |
| 375.0943844 | m5Am, m1Am, m62A | 0.00501 | 0.049270419 | |
| 376.0784 | m1Im | | 0.014828818 | |
| 377.0736489 | m1G, m2G, Gm | 1.02117 | 0.333555441 | |
| 379.0780656 | ac4Cm | 0.00685 | 0.005040526 | |
| 381.0573302 | ncm5U | 0.03373 | 0.24798213 | |
| 382.0413458 | cm5U | | 0.150752208 | |
| 383.0552217 | mnm5s2U | | 0.007783258 | |
| 389.0736489 | ac6A | | 0.13312548 | |
| 391.089299 | m1Gm, m22G, m2Gm, preQ1, “m2, 7G” | 0.62563 | 0.184991373 | 0.17409085 |
| 395.0729802 | ncm5Um | | 0.012101901 | |
| 396.0569958 | mcm5U | | 0.050911349 | |
| 398.0362604 | cmo5U, chm5U | | 0.26312128 | |
| 404.084548 | G+ | | 0.005922319 | |
| 405.1049491 | m22Gm, “m2, 2, 7G”, “m2, 7Gm” | | 0.002464382 | |
| 411.0678949 | cmnm5U | | 0.038101975 | |
| 412.0519104 | mcmo5U, mchm5U | | 0.068860358 | |
| 427.0450509 | cmnm$^5$s$^2$U | 0.01016 | | |

TABLE F-continued

W303 strain of *S. cerevisiae* with LA virus.

| Mono-isotopic mass (Da) | Modification | BY4741 | Total RNA (w303) | Captured RNA |
|---|---|---|---|---|
| 492.100592 | t6A | 0.13385 | | |
| 495.868906 | f5se2U | | 0.001166759 | |
| 559.0716734 | Ar(p) | | 0.06270116 | |
| 575.066588 | Gr(p) | | 0.217770255 | |
| 588.1581068 | yW | 0.1837 | | |

TABLE G

Exemplary names and structures of RNA having modifications identified in yeast having knockdown genes associated with prostate cancer see FIG. K for percentage difference as up regulated (+ or no sign in front of number) and down regulated (– in front of number) or (—) as no change. Structures from world wide web://mods.rna.albany.edu/ Hosted by The RNA Institute, College of Arts and Sciences, State University of New York at Albany and world wide web://modomics.genesilico.pl/.

| Structure name | Names (common) | Structure(s), respectively | TRM1 (% difference) | LHP1P (% difference) |
|---|---|---|---|---|
| C | cytidine | 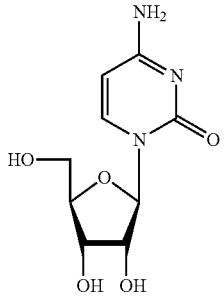 | −2.93 | −13.27 |
| Y, U | Pseudouridine, uridine | 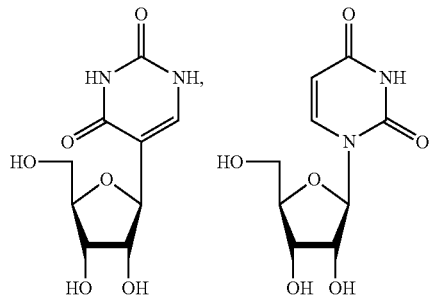 | 7.13 | −0.79 |
| D | dihydrouridine | 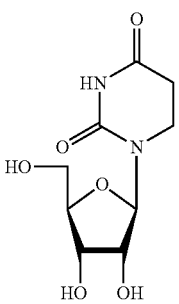 | 0.07 | 0.07 |

TABLE G-continued

*Exemplary names and structures of RNA having modifications identified in yeast having knockdown genes associated with prostate cancer see FIG. K for percentage difference as up regulated (+ or no sign in front of number) and down regulated (− in front of number) or (—) as no change. Structures from world wide web://mods.rna.albany.edu/ Hosted by The RNA Institute, College of Arts and Sciences, State University of New York at Albany and world wide web://modomics.genesilico.pl/.*

| Structure name | Names (common) | Structure(s), respectively | TRM1 (% difference) | LHP1P (% difference) |
|---|---|---|---|---|
| $m^3C$, $m^5C$, $Cm$, $m^4C$ | 3-methylcytidine, 5-methylcytidine, 2'-O-methylcytidine, $N^4$-methylcytidine | 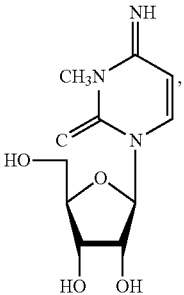 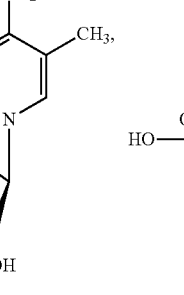 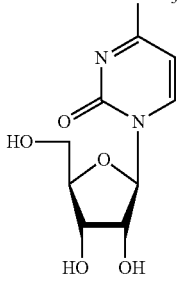 | 52.79 | 52.79 |
| $m^3Y$, $Um$, $m^5U$, $m^1Y$, $Ym$, $m^3U$ | 3-methylpseudouridine, 2'-O-methyluridine, 5-methyluridine, 1-methylpseudouridine, 2'-O-methylpseudouridine, 3-methyluridine | 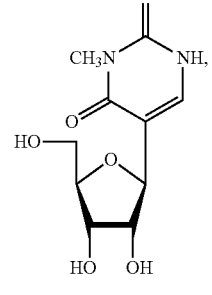 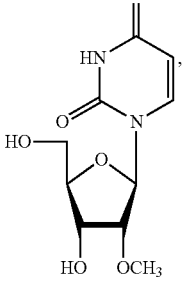 | 72.64 | 50.02 |

TABLE G-continued

Exemplary names and structures of RNA having modifications identified in yeast having knockdown genes associated with prostate cancer see FIG. K for percentage difference as up regulated (+ or no sign in front of number) and down regulated (– in front of number) or (—) as no change. Structures from world wide web://mods.rna.albany.edu/ Hosted by The RNA Institute, College of Arts and Sciences, State University of New York at Albany and world wide web://modomics.genesilico.pl/.

| Structure name | Names (common) | Structure(s), respectively | TRM1 (% difference) | LHP1P (% difference) |
| --- | --- | --- | --- | --- |

TABLE G-continued

*Exemplary names and structures of RNA having modifications identified in yeast having knockdown genes associated with prostate cancer see FIG. K for percentage difference as up regulated (+ or no sign in front of number) and down regulated (− in front of number) or (—) as no change. Structures from world wide web://mods.rna.albany.edu/ Hosted by The RNA Institute, College of Arts and Sciences, State University of New York at Albany and world wide web://modomics.genesilico.pl/.*

| Structure name | Names (common) | Structure(s), respectively | TRM1 (% difference) | LHP1P (% difference) |
|---|---|---|---|---|
| A | adenosine | 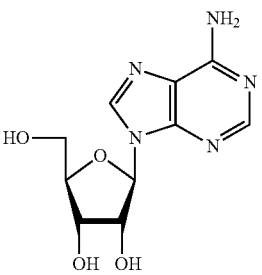 | 6.11 | 6.27 |
| I | inosine | 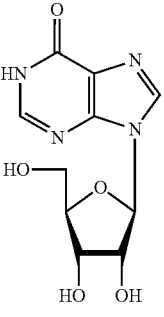 | 1.00 | 1.03 |
| $m^3C$, Cm, $m^4C$ | 5-methylcytidine, 2'-O-methylcytidine, $N^4$-methylcytidine | 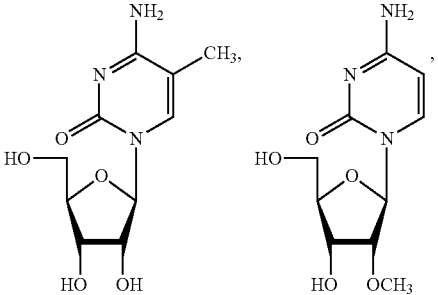 | 79.85 | 79.85 |

TABLE G-continued

*Exemplary names and structures of RNA having modifications identified in yeast having knockdown genes associated with prostate cancer see FIG. K for percentage difference as up regulated (+ or no sign in front of number) and down regulated (− in front of number) or (—) as no change. Structures from world wide web://mods.rna.albany.edu/ Hosted by The RNA Institute, College of Arts and Sciences, State University of New York at Albany and world wide web://modomics.genesilico.pl/.*

| Structure name | Names (common) | Structure(s), respectively | TRM1 (% difference) | LHP1P (% difference) |
|---|---|---|---|---|
| G | guanosine | | −2.12 | −2.12 |
| $ac^4C$, $f^5Cm$ | $N^4$-acetylcytidine, 5-formyl-2'-O-methylcytidine | | 0.19 | 0.19 |
| $m^6_2A$¥ | $N^6,N^6$-dimethyladenosine | | — | — |

TABLE G-continued

*Exemplary names and structures of RNA having modifications identified in yeast having knockdown genes associated with prostate cancer see FIG. K for percentage difference as up regulated (+ or no sign in front of number) and down regulated (− in front of number) or (—) as no change. Structures from world wide web://mods.rna.albany.edu/ Hosted by The RNA Institute, College of Arts and Sciences, State University of New York at Albany and world wide web://modomics.genesilico.pl/.*

| Structure name | Names (common) | Structure(s), respectively | TRM1 (% difference) | LHP1P (% difference) |
|---|---|---|---|---|
| m¹G, m²G, Gm | 1-methylguanosine, N²-methylguanosine, 2'-O-methylguanosine | 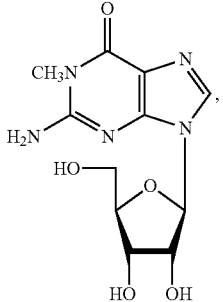 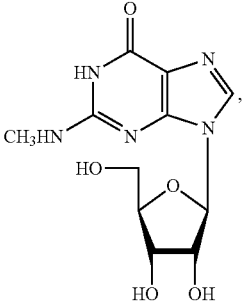 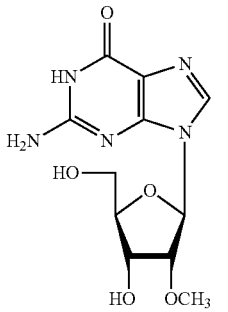 | 71.94 | 45.22 |
| ac⁴Cm | N⁴-acetyl-2'-O-methylcytidine | 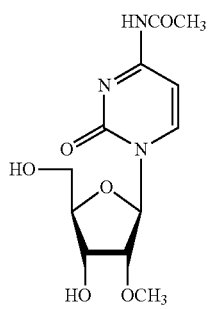 | −0.74 | −14.89 |
| ncm⁵U | 5-carbamoylmethyluridine | 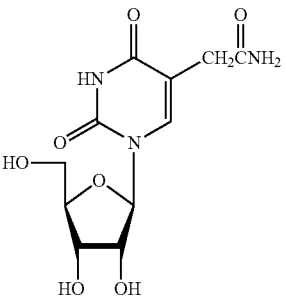 | 0.29 | 0.29 |

TABLE G-continued

*Exemplary names and structures of RNA having modifications identified in yeast having knockdown genes associated with prostate cancer see FIG. K for percentage difference as up regulated (+ or no sign in front of number) and down regulated (– in front of number) or (—) as no change. Structures from world wide web://mods.rna.albany.edu/ Hosted by The RNA Institute, College of Arts and Sciences, State University of New York at Albany and world wide web://modomics.genesilico.pl/.*

| Structure name | Names (common) | Structure(s), respectively | TRM1 (% difference) | LHP1P (% difference) |
|---|---|---|---|---|
| $m^1Gm$, $m2_2G$, $m^2Gm$, preQ1, $m2_7G$ | 1,2'-O-dimethylguanosine, $N^2,N^2$-dimethylguanosine, $N^2,2'$-O-dimethylguanosine, 7-aminomethyl-7-deazaguanosine, $N^2,7$-dimethylguanosine | 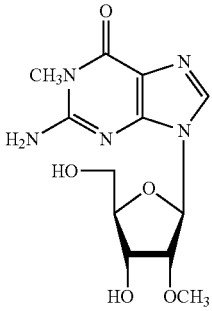 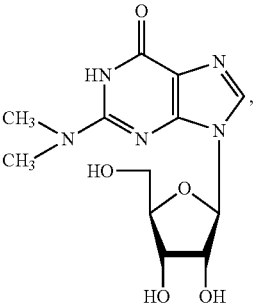 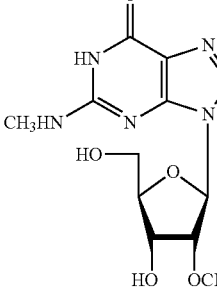 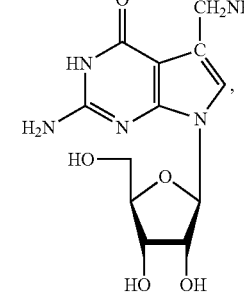 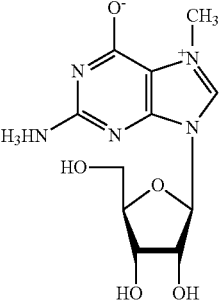 | — | — |
| $ncm^5Um$ | 5-carbamoylmethyl-2'-O-methyluridine | 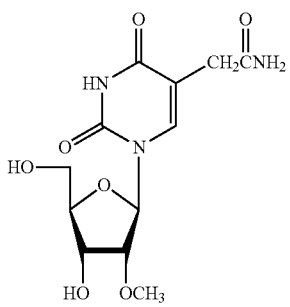 | −0.17 | −0.17 |

TABLE G-continued

Exemplary names and structures of RNA having modifications identified in yeast having knockdown genes associated with prostate cancer see FIG. K for percentage difference as up regulated (+ or no sign in front of number) and down regulated (− in front of number) or (—) as no change. Structures from world wide web://mods.rna.albany.edu/ Hosted by The RNA Institute, College of Arts and Sciences, State University of New York at Albany and world wide web://modomics.genesilico.pl/.

| Structure name | Names (common) | Structure(s), respectively | TRM1 (% difference) | LHP1P (% difference) |
|---|---|---|---|---|
| $nm^5s^2U^\frown$ | 5-aminomethyl-2-thiouridine | | — | — |
| imG2 | isowyosine | | −2.55 | −0.25 |
| $t^6A$ | $N^6$-threonylcarbamoyladenosine | | −7.40 | −0.74 |

TABLE H

Global Profiling. Hits observed by searching data obtained from S. cerevisiae against a non-redundant database generated by combining data from the RNA Modifications and Modomics Databases.

| Experimental mass (Da) | Monoisotopic mass (Da) | Hit |
|---|---|---|
| 323.052 | 323.052 | $C^\ddagger$ |
| 324.036 | 324.036 | $Y^\ddagger$, $U^\ddagger$ |
| 326.052 | 326.052 | $D^\ddagger$ |
| 337.068 | 337.068 | $m^3C$, $m^5C$, $Cm^\ddagger$, $m^4C*$ |
| 338.052 | 338.052 | $m^3Y*$, $Um^\ddagger$, $m^5U$, $m^1Y$, $Ym^\ddagger*$, $m^3U$ |
| 347.063 | 347.063 | $A^\ddagger$ |
| 348.047 | 348.047 | $I^\ddagger$ |
| 361.079 | 361.079 | $m^1A$, $m^2A*$, $m^6A$, $m^8A*$, $Am^\ddagger$ |
| 363.058 | 363.058 | $G^\ddagger$ |
| 365.062 | 365.062 | $ac^4C^\ddagger*$, $f^5Cm^\ddagger*$ |
| 375.094 | 375.094 | $m^6Am*$, $m^1Am*$, $m^6_2A^\ddagger*$ |
| 377.076 | 377.074 | $m^1G^\ddagger$, $m^2G^\ddagger$, $m^7G^\ddagger$, $Gm^\ddagger$ |
| 379.076 | 379.078 | $ac^4Cm^\ddagger*$ |
| 381.057 | 381.057 | $ncm^5U*$ |

TABLE H-continued

Global Profiling. Hits observed by searching data obtained from
S. cerevisiae against a non-redundant database generated by combining
data from the RNA Modifications and Modomics Databases.

| Experimental mass (Da) | Monoisotopic mass (Da) | Hit |
|---|---|---|
| 391.089 | 391.089 | $m^1Gm^*$, $m^2_2G$, $m^3Gm$, $preQ1^*$, $m^2_7G$ |
| 427.043 | 427.045 | $cmnm^5s^2U$ |
| 492.101 | 492.101 | $t^6A$‡ |
| 588.158 | 588.158 | $yW$‡ |

‡Assignments corroborated by tandem mass spectrometry determinations.
*Modifications that were not previously detected in S. cerevisiae.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in biochemistry, chemistry, microbiology, molecular biology, and medicine, or related fields are intended to be within the scope of the following claims.

The invention claimed is:

1. A method for identifying a whole cell with a modified nucleic acid structure profile, comprising:
   (a) providing,
      (i) a biological sample comprising a whole-cell, said whole-cell comprising nucleic acids; and
      (ii) a mass spectrometer;
   (b) disrupting said whole-cell in a mixture comprising a denaturation solution and an affinity capture media under conditions that form an affinity-captured individual nucleic acid;
   (c) eluting said individual nucleic acid from said affinity-captured individual nucleic acid to create a mononucleotide mixture;
   (d) infusing said mononucleotide mixture into said mass spectrometer to measure a molecular mass of said individual nucleic acid;
   (e) identifying the presence of a modified nucleic acid structure of said nucleic acid based upon said measured molecular weight;
   (f) repeating steps c-e so as to identify a genome-wide modified nucleotide structure profile for said whole-cell; and
   (g) identifying said whole-cell with said genome-wide modified nucleotide structure profile.

2. The method of claim 1, wherein said mononucleotide is a ribonucleotide (RNA).

3. The method of claim 1, wherein said mononucleotide is a deoxyribonucleotide (DNA).

4. The method of claim 1, wherein said whole-cell is a mammalian cell.

5. The method of claim 1, wherein said whole-cell is any type of cell or microorganism.

6. The method of claim 1, wherein said identified whole-cell is selected from the group consisting of a single cell microorganism, a control cell, a healthy cell, a cancer cell, an infected cell and a stressed cell.

7. The method of claim 1, wherein said mass spectrometer comprises ion mobility spectrometry-mass spectrometry (IMS-MS) and/or high-resolution mass spectrometry.

8. The method of claim 7, wherein a heat-map plot is derived from said mass spectrometry then used to identify an isobaric modified nucleic acid for including in said profile.

9. The method of claim 1, wherein said affinity capture media is selected from the group consisting of biotin-streptavidin coupling, iminothiolane coupling, disulfide coupling, poly-A coupling and antisense coupling.

10. The method of claim 1, wherein said affinity capture media comprises a plurality of beads.

11. The method of claim 10, wherein said plurality of beads is selected from the group consisting of glass beads, magnetic beads and paramagnetic beads.

12. The method of claim 1, further comprising contacting said mononucleotide mixture with an immunoassay to identify said modified nucleic acid structure profile.

13. The method of claim 1, wherein said modified nucleic acid structure comprises a post-transcriptional modification.

14. A method for identifying a whole cell with a modified nucleic acid structure profile, comprising:
   (a) disrupting a whole-cell comprising nucleic acids in a mixture comprising a denaturation solution and an affinity capture media under conditions that form an affinity-captured individual nucleic acid;
   (b) forming a mononucleotide mixture by eluting an individual nucleic acid from said affinity-captured individual nucleic acid;
   (c) infusing said mononucleotide mixture into a mass spectrometer to measure a molecular mass of said individual nucleic acid;
   (d) identifying the presence of a modified nucleic acid structure of said nucleic acid based upon said measured molecular weight;
   (e) repeating steps b-d so as to identify a genome-wide modified nucleotide structure profile for said whole-cell; and
   (f) identifying said whole-cell with said genome-wide modified nucleotide structure profile.

15. The method of claim 14, wherein said mononucleotide mixture comprises nucleotides comprising ribose sugar.

16. The method of claim 14, wherein said mononucleotide mixture comprises nucleotides comprising a sugar moiety consisting of ribose sugar.

17. The method of claim 14, wherein said mononucleotide mixture comprises nucleotides comprising deoxyribose sugar.

18. The method of claim 14, wherein said mononucleotide mixture comprises nucleotides comprising a sugar moiety consisting of deoxyribose sugar.

19. The method of claim 14, wherein said whole-cell is a mammalian cell.

20. A method for identifying a whole cell with a modified nucleic acid structure profile, comprising:
   (a) disrupting a whole-cell comprising nucleic acids in a mixture comprising a denaturation solution and an affinity capture media comprising a plurality of beads under conditions that form an affinity-captured individual nucleic acid;
   (b) forming a mononucleotide mixture by eluting an individual nucleic acid from said affinity-captured individual nucleic acid;
   (c) infusing said mononucleotide mixture into a mass spectrometer to measure a molecular mass of said individual nucleic acid, wherein said mass spectrometer comprises ion mobility spectrometry-mass spectrometry (IMS-MS) and/or high-resolution mass spectrometry;
   (d) identifying the presence of a modified nucleic acid structure of said nucleic acid based upon said measured molecular weight;
   (e) repeating steps b-d so as to identify a genome-wide modified nucleotide structure profile for said whole-cell; and
   (f) identifying said whole-cell with said genome-wide modified nucleotide structure profile, wherein said identified whole-cell is selected from the group consisting of a single cell microorganism, a control cell, a healthy cell, a cancer cell, an infected cell, and a stressed cell.

* * * * *

SEQUENCE LISTING

```
<160> NUMBER OF SEQ ID NOS: 15

<210> SEQ ID NO 1
<211> LENGTH: 57
<212> TYPE: DNA
<213> ORGANISM: Artificial Sequence
<220> FEATURE:
<223> OTHER INFORMATION: Synthetic

<400> SEQUENCE: 1
gcugggaugu uggcuuagaa gcagccauca uuuaaagagu gcguaacacg ucacagc        57

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
agacgcacaa aaccaaguuc aauag                                           25

<210> SEQ ID NO 3
<211> LENGTH: 25
<212> TYPE: DNA
<213> ORGANISM: Artificial Sequence
<220> FEATURE:
<223> OTHER INFORMATION: Synthetic

<400> SEQUENCE: 3
ctattgaact tggttttgtg cgtct                                           25

<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
gacgcacaaa accaaguuca auaga                                           25

<210> SEQ ID NO 5
<211> LENGTH: 25
<212> TYPE: DNA
<213> ORGANISM: Artificial Sequence
<220> FEATURE:
<223> OTHER INFORMATION: Synthetic
```

```
<400> SEQUENCE: 5
tctattgaac ttggttttgt gcgtc                                    25

<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
cuuagacgca caaaaccaag uucaa                                    25

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
ttgaacttgg ttttgtgcgt ctaag                                    25

<210> SEQ ID NO 8
<211> LENGTH: 25
<212> TYPE: DNA
<213> ORGANISM: Artificial Sequence
<220> FEATURE:
<223> OTHER INFORMATION: Synthetic

<400> SEQUENCE: 8
guaacuuaga cgcacaaaac caagu                                    25

<210> SEQ ID NO 9
<211> LENGTH: 25
<212> TYPE: DNA
<213> ORGANISM: Artificial Sequence
<220> FEATURE:
<223> OTHER INFORMATION: Synthetic

<400> SEQUENCE: 9
acttggtttt gtgcgtctaa gttac                                    25

<210> SEQ ID NO 10
<211> LENGTH: 25
<212> TYPE: DNA
<213> ORGANISM: Artificial Sequence
<220> FEATURE:
<223> OTHER INFORMATION: Synthetic

<400> SEQUENCE: 10
acuuagacgc acaaaaccaa guuca                                    25

<210> SEQ ID NO 11
<211> LENGTH: 25
<212> TYPE: DNA
<213> ORGANISM: Artificial Sequence
<220> FEATURE:
<223> OTHER INFORMATION: Synthetic

<400> SEQUENCE: 11
tgaacttggt tttgtgcgtc taagt                                    25

<210> SEQ ID NO 12
<211> LENGTH: 25
```

```
<212> TYPE: DNA
<213> ORGANISM: Artificial Sequence
<220> FEATURE:
<223> OTHER INFORMATION: Synthetic

<400> SEQUENCE: 12
aacuuagacg cacaaaacca aguuc                                          25

<210> SEQ ID NO 13
<211> LENGTH: 25
<212> TYPE: DNA
<213> ORGANISM: Artificial Sequence
<220> FEATURE:
<223> OTHER INFORMATION: Synthetic

<400> SEQUENCE: 13
gaacttggtt ttgtgcgtct aagtt                                          25

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
uaacuuagac gcacaaaacc                                                20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
ggttttgtgc gtctaagtta                                                20
```